US011300576B2

(12) United States Patent
Sierks et al.

(10) Patent No.: US 11,300,576 B2
(45) Date of Patent: Apr. 12, 2022

(54) DARPIN REAGENTS THAT DISTINGUISH ALZHEIMER'S DISEASE AND PARKINSON'S DISEASE SAMPLES

(71) Applicant: ARIZONA BOARD OF REGENTS ON BEHALF OF ARIZONA STATE UNIVERSITY, Scottsdale, AZ (US)

(72) Inventors: Michael Sierks, Fort McDowell, AZ (US); Stephanie Williams, Phoenix, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 71 days.

(21) Appl. No.: 16/776,218

(22) Filed: Jan. 29, 2020

(65) Prior Publication Data
US 2020/0241014 A1 Jul. 30, 2020

Related U.S. Application Data

(60) Provisional application No. 62/798,381, filed on Jan. 29, 2019.

(51) Int. Cl.
*G01N 33/68* (2006.01)
*C07K 14/47* (2006.01)

(52) U.S. Cl.
CPC ...... *G01N 33/6896* (2013.01); *C07K 14/4711* (2013.01); *C07K 2318/00* (2013.01); *G01N 2800/2821* (2013.01); *G01N 2800/2835* (2013.01)

(58) Field of Classification Search
CPC ....... G01N 33/6896; G01N 2800/2821; G01N 2800/2835; G01N 2800/52; G01N 2333/4709; C07K 14/4711; C07K 2318/00
See application file for complete search history.

(56) References Cited

U.S. PATENT DOCUMENTS

| | | | |
|---|---|---|---|
| 4,168,146 A | 9/1979 | Grubb et al. | |
| 4,246,339 A | 1/1981 | Cole et al. | |
| 4,277,560 A | 7/1981 | Gray et al. | |
| 4,313,734 A | 2/1982 | Leuvering | |
| 4,366,241 A | 12/1982 | Tom et al. | |
| 4,435,504 A | 3/1984 | Zuk et al. | |
| 4,496,654 A | 1/1985 | Katz et al. | |
| 4,632,901 A | 12/1986 | Valkirs et al. | |
| 4,703,017 A | 10/1987 | Campbell et al. | |
| 4,740,468 A | 4/1988 | Weng et al. | |
| 4,743,560 A | 5/1988 | Campbell et al. | |
| 4,770,853 A | 9/1988 | Bernstein | |
| 4,775,636 A | 10/1988 | Moeremans et al. | |
| 4,806,311 A | 2/1989 | Greenquist | |
| 4,806,312 A | 2/1989 | Greenquist | |
| 4,812,293 A | 3/1989 | McLaurin et al. | |
| 4,855,240 A | 8/1989 | Rosenstein et al. | |
| 4,857,453 A | 8/1989 | Ullman et al. | |
| 4,861,711 A | 8/1989 | Friesen et al. | |
| 4,920,046 A | 4/1990 | McFarland et al. | |
| 4,943,522 A | 7/1990 | Eisinger et al. | |
| 4,945,042 A | 7/1990 | Geiger et al. | |
| 5,001,049 A | 3/1991 | Klein et al. | |
| 5,073,484 A | 12/1991 | Swanson et al. | |
| 5,075,078 A | 12/1991 | Osikowicz et al. | |
| 5,120,643 A | 6/1992 | Ching et al. | |
| 5,126,241 A | 6/1992 | Schenk | |
| 5,229,073 A | 7/1993 | Luo et al. | |
| 5,279,935 A | 1/1994 | Nycz | |
| 5,424,193 A | 6/1995 | Pronovost et al. | |
| 5,451,504 A | 9/1995 | Fitzpatrick et al. | |
| 5,451,507 A | 9/1995 | Skold et al. | |
| 5,591,645 A | 1/1997 | Rosenstein | |
| 5,665,539 A | 9/1997 | Sano et al. | |
| 5,712,172 A | 1/1998 | Huang et al. | |
| 5,798,273 A | 8/1998 | Shuler et al. | |
| 6,258,548 B1 | 7/2001 | Buck | |
| 6,283,761 B1 | 9/2001 | Joao | |
| 6,368,876 B1 | 4/2002 | Huang et al. | |
| 6,555,390 B2 | 4/2003 | Chandler | |
| 6,656,744 B2 | 12/2003 | Pronovost et al. | |
| 6,699,722 B2 | 3/2004 | Bauer et al. | |
| 7,517,699 B2 | 4/2009 | Bauer et al. | |

(Continued)

FOREIGN PATENT DOCUMENTS

EP 0296724 B1 1/1995
EP 0299428 B1 1/1996

(Continued)

OTHER PUBLICATIONS

Boersma YL. Advances in the application of designed ankyrin repeat proteins (DARPins) as research tools and protein therapeutics. Methods Mol. Biol. 1798, 307-327. (Year: 2018).*

(Continued)

*Primary Examiner* — Kimberly Ballard
(74) *Attorney, Agent, or Firm* — Rodney J. Fuller; Booth Udall Fuller, PLC

(57) ABSTRACT

Disclosed are diagnostics for neurodegenerative diseases, and in particular to design ankyrin repeat protein (DARPins) reagents that distinguish Alzheimer's disease (AD) from Parkinson's disease (PD). Methods of diagnosing, monitoring treatment efficacy and developing treatments for neurodegenerative diseases, such as AD and PD are disclosed based upon the use of the AD or PD specific DARPins.

15 Claims, 39 Drawing Sheets

Specification includes a Sequence Listing.

(56) References Cited

U.S. PATENT DOCUMENTS

| | | | |
|---|---|---|---|
| 8,617,549 | B2 | 12/2013 | Sierks et al. |
| 9,340,606 | B2 | 5/2016 | Sierks et al. |
| 9,512,212 | B2 | 12/2016 | Sierks et al. |
| 9,567,393 | B2 | 2/2017 | Sierks et al. |
| 9,650,436 | B2 | 5/2017 | Sierks et al. |
| 9,915,668 | B2 | 3/2018 | Sierks et al. |
| 9,938,330 | B2 | 4/2018 | Sierks et al. |
| 10,191,068 | B2 | 1/2019 | Sierks et al. |
| 10,407,495 | B2 | 9/2019 | Sierks et al. |
| 2003/0049857 | A1 | 3/2003 | Chan |
| 2004/0241876 | A1 | 12/2004 | Fannes |
| 2005/0239108 | A1 | 10/2005 | Barletta et al. |
| 2014/0011691 | A1 | 1/2014 | Sierks et al. |
| 2016/0102140 | A1 | 4/2016 | Sierks |
| 2016/0291037 | A1 | 10/2016 | Sierks et al. |
| 2016/0320412 | A1 | 11/2016 | Sierks et al. |
| 2017/0204170 | A1 | 7/2017 | Sierks et al. |
| 2017/0226158 | A1 | 8/2017 | Minter et al. |
| 2018/0298086 | A1 | 10/2018 | Sierks et al. |
| 2018/0364577 | A1 | 12/2018 | Sierks et al. |
| 2019/0010504 | A1 | 1/2019 | Sierks et al. |
| 2019/0185553 | A1 | 6/2019 | Sierks et al. |
| 2019/0195892 | A1 | 6/2019 | Sierks et al. |
| 2019/0250171 | A1 | 8/2019 | Sierks et al. |
| 2020/0278358 | A1 | 9/2020 | Sierks et al. |
| 2020/0299367 | A1 | 9/2020 | Sierks et al. |
| 2021/0032634 | A1 | 2/2021 | Sierks et al. |

FOREIGN PATENT DOCUMENTS

| | | |
|---|---|---|
| EP | 0810436 A1 | 12/1997 |
| WO | 8808534 A1 | 11/1988 |
| WO | 9212428 A1 | 7/1992 |
| WO | 9401775 A1 | 1/1994 |
| WO | 9516207 A1 | 6/1995 |
| WO | 9706439 A1 | 2/1997 |
| WO | 9836278 A1 | 8/1998 |
| WO | 2008030546 A2 | 3/2008 |
| WO | 2020252394 A2 | 12/2020 |

OTHER PUBLICATIONS

Edwards et al. J. Mol. Biol. 334:103-118. (Year: 2003).*
Lloyd et al. Protein Eng. Design & Select, 22(3):159-168. (Year: 2009).*
Pluckthun A. Designed ankyrin repeat proteins (DARPins): Binding proteins for research, diagnostics, and therapy. Annu. Rev. Pharmacol. Toxicol. 55: 489-511. (Year: 2015).*
Stumpp MT et al. DARPins: A new generation of protein therapeutics. Drug Discovery Today, 13 (15/16), 695-701. (Year: 2008).*
Altschul, Stephen F. et al., "Basic Local Alignment Search Tool", J. Mol. Biol. 215, 1990, pp. 403-410.
Altschul, Stephen F. et al., "Issues in searching molecular sequence databases", Nature Genetics vol. 6, Feb. 1994, pp. 119-129.
Binz, H. Kaspar et al., "Designing Repeat Proteins: Well-expressed, Soluble and Stable Proteins from Combinatorial Libraries of Consensus Ankyrin Repeat Proteins", J. Mol. Biol. 332, 2003, pp. 489-503.
Bitter, Grant A. et al., "Expression and Secretion Vectors for Yeast", Methods of Enzymology, vol. 153, 1987, pp. 516-544.
Corpet, Florence, "Multiple sequence alignment with hierarchical clustering", Nucleic Acids Research, vol. 16, No. 22, 1988, pp. 10881-10890.
Cory, Michael, "Computer-Assisted Drug Design", Principles of Pharmacology, Ch. 102, 1995, pp. 1517-1525.
Higgins, Desmond G. et al., "CLUSTAL: a package for performing multiple sequence alignment on a microcomputer", Gene, 73, 1988, pp. 237-244.
Higgins, Desmond G. et al., "Fast and sensitive multiple sequence alignments on a microcomputer", Cabios Communications, vol. 5, No. 2, 1989, pp. 151-153.
Needleman, Saul B. et al., "A General Method Applicable to the Search for Similarities in the Amino Acid Sequence of Two Proteins", J. Mol. Biol. 48, 1970, pp. 443-453.
Pearson, William R. et al., "Improved tools for biological sequence comparison", Proc. Natl. Acad. Sci., vol. 85, Apr. 1988, pp. 2444-2448.
Sano, Takeshi et al., "Immuno-PCR: Very Sensitive Antigen Detection by Means of Specific Antibody-DNA Conjugates", Science, vol. 258, Oct. 2, 199122.2, pp. 120-122.
Smith, Temple F. et al., "Comparison of Biosequences", Advances in Applied Mathematics 2, 1981, pp. 482-489.
Walters, D. Eric, "Computer-Assisted Modeling of Drugs," in Klegerman & Groves, eds., Chapter 10, 1993, pp. 165-174.
Sierks et al., U.S. Appl. No. 16/845,761, filed Apr. 10, 2020.

* cited by examiner

*Specifics of DARPin Protein Sequences*

Protein Template:
5' -
MKKIWLALAGLVLAFSASADYKEAQPAMDLGKKLLEAARAGQDDEVRILMANGADVNAXDXXGXTPLHLAAXXGHLEIVEVLLK
XGADVNAQDKFGKTAFDISIDNGNEDLAEILQAAAHHHHHHGAAEQKLISEEDLNGAA – 3' (SEQ ID NO: 1)

N-Cap:
5' – DLGKKLLEAARAGQDDEVRILMANGADV – 3' (SEQ ID NO: 2)

C-Cap:
5' – VNAQDKFGKTAFDISIDNGNEDLAEILQ – 3' (SEQ ID NO: 3)

Figure 1

*Table 1. Demographics and Medical History of AD and Control Cases*

| Mean SD (or %) | AD (N = 25) | Controls (N = 25) | P-Value |
| --- | --- | --- | --- |
| Average No. of Timepoints | 4.76 (0.52) | 4.88 (0.33) | 0.337 |
| Age (Years) | | | |
|    First Timepoint | 76.6 (5.48) | 77.9 (7.36) | 0.505 |
|    Last Timepoint | 83.9 (5.43) | 85.6 (7.55) | 0.371 |
| Length of Time (Years) | 7.22 (2.42) | 7.75 (2.84) | 0.483 |
| Male | 56% | 48% | 0.580 |
| Non-White Race | 0% | 0% | - |
| APOE Genotype | | | 0.065 |
|    22 | 0% | 4% | - |
|    23 | 0% | 12% | - |
|    24 | 0% | 4% | - |
|    33 | 44% | 64% | - |
|    34 | 52% | 12% | - |
|    44 | 0% | 4% | - |
| MMSE Score | 26.1 | 27.9 | 0.000 |

MMSE = Mini Mental Status Examination

Figure 4

SEQUENCE LISTING

```
<160> NUMBER OF SEQ ID NOS: 19

<210> SEQ ID NO 1
<211> LENGTH: 142
<212> TYPE: PRT
<213> ORGANISM: Artificial Sequence
<220> FEATURE:
<223> OTHER INFORMATION: AR module fragment
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (61)..(62)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (72)..(73)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid

<400> SEQUENCE: 1

Met Lys Lys Ile Trp Leu Ala Leu Ala Gly Leu Val Leu Ala Phe Ser
1               5                   10                  15

Ala Ser Ala Asp Tyr Lys Glu Ala Gln Pro Ala Met Asp Leu Gly Lys
            20                  25                  30

Lys Leu Leu Glu Ala Ala Arg Ala Gly Gln Asp Asp Glu Val Arg Ile
        35                  40                  45

Leu Met Ala Asn Gly Ala Asp Val Asn Ala Xaa Asp Xaa Xaa Gly Xaa
    50                  55                  60

Thr Pro Leu His Leu Ala Ala Xaa Xaa Gly His Leu Glu Ile Val Glu
65                  70                  75                  80

Val Leu Leu Lys Xaa Gly Ala Asp Val Asn Ala Gln Asp Lys Phe Gly
                85                  90                  95

Lys Thr Ala Phe Asp Ile Ser Ile Asp Asn Gly Asn Glu Asp Leu Ala
            100                 105                 110

Glu Ile Leu Gln Ala Ala Ala His His His His His His Gly Ala Ala
        115                 120                 125

Glu Gln Lys Leu Ile Ser Glu Glu Asp Leu Asn Gly Ala Ala
            130                 135                 140

<210> SEQ ID NO 2
<211> LENGTH: 28
<212> TYPE: PRT
```

```
<213> ORGANISM: Artificial Sequence
<220> FEATURE:
<223> OTHER INFORMATION: N-cap protein sequence

<400> SEQUENCE: 2

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val
            20                  25

<210> SEQ ID NO 3
<211> LENGTH: 28
<212> TYPE: PRT
<213> ORGANISM: Artificial Sequence
<220> FEATURE:
<223> OTHER INFORMATION: C-cap protein sequence

<400> SEQUENCE: 3

Val Asn Ala Gln Asp Lys Phe Gly Lys Thr Ala Phe Asp Ile Ser Ile
1               5                   10                  15

Asp Asn Gly Asn Glu Asp Leu Ala Glu Ile Leu Gln
            20                  25

<210> SEQ ID NO 4
<211> LENGTH: 664
<212> TYPE: DNA
<213> ORGANISM: Artificial Sequence
<220> FEATURE:
<223> OTHER INFORMATION: ADC1 DNA Sequence
<220> FEATURE:
<221> NAME/KEY: misc_feature
<222> LOCATION: (24)..(24)
<223> OTHER INFORMATION: n is a, c, g, or t

<400> SEQUENCE: 4
aagatttggc tggcgctggc tggnttagtt ttagcgttta gcgcatcggc ggactacaaa      60
gaggcccagc cggccatgga cctgggtaag aaactgctgg aagctgctcg tgctggtcag     120
gacgacgaag ttcgtatcct gatggctaac ggtgctgacg ttaacgctga cgaccgtaac     180
ggtatgactc cgctgcacct ggctgctcat cagggtcacc tggaaatcgt tgaagttctg     240
ctgaagtacg gtgctgacgt taacgctcag acaaattcg gtaagaccgc tttcgacatc      300
tccatcgaca acggtaacga ggacctggct gaaatcctgc aagcggccgc acatcatcat     360
caccatcacg gggccgcaga acaaaaactc atctcagaag aggatctgaa tggggccgca     420
tagactgttg aaagttgttt agcaaaacct catacagaaa attcatttac taacgtctgg     480
aaagacgaca aactttaga tcgttacgct aactatgagg gctgtctgtg aatgctaca      540 ggcgttgtgg tttgtactgg tgacgaaact cagtgttacg gtacatgggt tcctattggg     600
cttgctatcc ctgaaaatga gggtggtggc tctgagggtg gcggttctga gggtggcggt     660
tctg                                                                   664

<210> SEQ ID NO 5
<211> LENGTH: 140
<212> TYPE: PRT
<213> ORGANISM: Artificial Sequence
<220> FEATURE:
<223> OTHER INFORMATION: SEQ ID NO: 5
<220> FEATURE:
<221> NAME/KEY: misc_feature
<222> LOCATION: (8)..(8)
<223> OTHER INFORMATION: Xaa can be any naturally occurring amino acid

<400> SEQUENCE: 5
```

```
Lys Ile Trp Leu Ala Leu Ala Xaa Leu Val Leu Ala Phe Ser Ala Ser
1               5                   10                  15

Ala Asp Tyr Lys Glu Ala Gln Pro Ala Met Asp Leu Gly Lys Lys Leu
            20                  25                  30

Leu Glu Ala Ala Arg Ala Gly Gln Asp Asp Glu Val Arg Ile Leu Met
        35                  40                  45

Ala Asn Gly Ala Asp Val Asn Ala Asp Arg Asn Gly Met Thr Pro
    50                  55                  60

Leu His Leu Ala Ala His Gln Gly His Leu Glu Ile Val Glu Val Leu
65              70                  75                  80

Leu Lys Tyr Gly Ala Asp Val Asn Ala Gln Asp Lys Phe Gly Lys Thr
            85                  90                  95

Ala Phe Asp Ile Ser Ile Asp Asn Gly Asn Glu Asp Leu Ala Glu Ile
            100                 105                 110

Leu Gln Ala Ala Ala His His His His His His Gly Ala Ala Glu Gln
        115                 120                 125

Lys Leu Ile Ser Glu Glu Asp Leu Asn Gly Ala Ala
        130                 135                 140

<210> SEQ ID NO 6
<211> LENGTH: 640
<212> TYPE: DNA
<213> ORGANISM: Artificial Sequence
<220> FEATURE:
<223> OTHER INFORMATION: ADC3 DNA Sequence
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (446)..(446)
<223> OTHER INFORMATION: n is a, c, g, or t
<220> FEATURE:
<221> NAME/KEY: misc_feature
<222> LOCATION: (448)..(449)
<223> OTHER INFORMATION: n is a, c, g, or t
<220> FEATURE:
<221> NAME/KEY: misc_feature
<222> LOCATION: (616)..(616)
<223> OTHER INFORMATION: n is a, c, g, or t

<400> SEQUENCE: 6
tggnttagtt ttagcgttta gcgcatcggc ggactacaaa gaggcccagc cggccatgga      60
cctgggtaag aaactgctgg aagctgctcg tgctggtctg gacgacgaag ttcgtatcct     120
gatggctaac ggtgctgacg ttaacgctac tgacactgac ggttctagtc cgctgcacct     180
ggctgctcag gaaggtcacc tggaaatcgt tgaagttctg ctgaagtacg gtgctgacgt     240
taacgctcag gacaaattcg gtaagaccgc tttcgacatc tccatcgaca acggtaacga     300
ggacctggct gaaatcctgc aagcggccgc acatcatcat caccatcacg ggccgcaga     360 acaaaaactc atctcagaag aggatctgaa tggggccgca tagactgttg aaagttgttt     420
agcaaaacct catacagaaa attcantnnc taacgtctgg aaagacgaca aaactttaga     480
tcgttacgct aactatgagg gctgtctgtg gaatgctaca ggcgttgtgg tttgtactgg     540
tgacgaaact cagtgttacg gtacatgggt tcctattggg cttgctatcc ctgaaaatga     600
gggtggtggc tctganggtg gcggttctga gggtggcggt                          640

<210> SEQ ID NO 7
<211> LENGTH: 136
```

```
<212> TYPE: PRT
<213> ORGANISM: Artificial Sequence
<220> FEATURE:
<223> OTHER INFORMATION: ADC3 protein sequence
<220> FEATURE:
<221> NAME/KEY: misc_feature
<222> LOCATION: (4)..(4)
<223> OTHER INFORMATION: Xaa can be any naturally occurring amino acid

<400> SEQUENCE: 7

Gly Ala Gly Xaa Leu Val Leu Ala Phe Ser Ala Ser Ala Asp Tyr Lys
1               5                   10                  15

Glu Ala Gln Pro Ala Met Asp Leu Gly Lys Lys Leu Leu Glu Ala Ala
            20                  25                  30

Arg Ala Gly Leu Asp Asp Glu Val Arg Ile Leu Met Ala Asn Gly Ala
        35                  40                  45

Asp Val Asn Ala Thr Asp Thr Asp Gly Ser Ser Pro Leu His Leu Ala
    50                  55                  60

Ala Gln Glu Gly His Leu Glu Ile Val Glu Val Leu Leu Lys Tyr Gly
65                  70                  75                  80

Ala Asp Val Asn Ala Gln Asp Lys Phe Gly Lys Thr Ala Phe Asp Ile
                85                  90                  95

Ser Ile Asp Asn Gly Asn Glu Asp Leu Ala Glu Ile Leu Gln Ala Ala
            100                 105                 110

Ala His His His His His His Gly Ala Ala Glu Gln Lys Leu Ile Ser
        115                 120                 125

Glu Glu Asp Leu Asn Gly Ala Ala
    130                 135

<210> SEQ ID NO 8
<211> LENGTH: 660
<212> TYPE: DNA
<213> ORGANISM: Artificial Sequence
<220> FEATURE:
<223> OTHER INFORMATION: ADC6 DNA Sequence
<220> FEATURE:
<221> NAME/KEY: misc_feature
<222> LOCATION: (456)..(459)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t

<400> SEQUENCE: 8
ctggcgctgg ctggtttagt tttagcgttt agcgcatcgg cggactacaa agaggcccag      60
ccggccatgg acctgggtaa gaaactgctg gaagctgctc gtgctggtca ggacgacgaa     120
gttcgtatcc tgatggctaa cggtgctgac gttaacgctg ctgacttcaa cggtcaaact     180
ccgctgcacc tggctgctgt tgggggtcac ctggaaatcg ttgaagttct gctgaagaac     240
ggtgctgacg ttaacgctca ggacaaattc ggtaagaccg cttctcgacat ctccatcgac     300 aacggtaacg aggacctggc tgaaatcctg caagcggccg cacatcatca tcaccatcac     360
ggggccgcag aacaaaaact catctcagaa gaggatctga atggggccgc atagactgtt     420
gaaagttgtt tagcaaaacc tcatacagaa aattcnnnna ctaacgtctg aaagacgac     480 aaaactttag atcgttacgc taactatgag ggctgtctgt ggaatgctac aggcgttgtg     540
gtttgtactg gtgacgaaac tcagtgttac ggtacatggg ttcctattgg gcttgctatc     600
cctgaaaatg agggtggtgg ctctganggt ggcggttctg agggtggcgg ttctgagggt     660
```

<210> SEQ ID NO 9
<211> LENGTH: 137
<212> TYPE: PRT
<213> ORGANISM: Artificial Sequence
<220> FEATURE:
<223> OTHER INFORMATION: ADC6 protein sequence

<400> SEQUENCE: 9

```
Leu Ala Leu Ala Gly Leu Val Leu Ala Phe Ser Ala Ser Ala Asp Tyr
1               5                   10                  15

Lys Glu Ala Gln Pro Ala Met Asp Leu Gly Lys Lys Leu Leu Glu Ala
            20                  25                  30

Ala Arg Ala Gly Gln Asp Asp Glu Val Arg Ile Leu Met Ala Asn Gly
        35                  40                  45

Ala Asp Val Asn Ala Ala Asp Phe Asn Gly Gln Thr Pro Leu His Leu
    50                  55                  60

Ala Ala Val Trp Gly His Leu Glu Ile Val Glu Val Leu Leu Lys Asn
65                  70                  75                  80

Gly Ala Asp Val Asn Ala Gln Asp Lys Phe Gly Lys Thr Ala Phe Asp
                85                  90                  95

Ile Ser Ile Asp Asn Gly Asn Glu Asp Leu Ala Glu Ile Leu Gln Ala
            100                 105                 110

Ala Ala His His His His His His Gly Ala Ala Glu Gln Lys Leu Ile
        115                 120                 125

Ser Glu Glu Asp Leu Asn Gly Ala Ala
    130                 135
```

<210> SEQ ID NO 10
<211> LENGTH: 600
<212> TYPE: DNA
<213> ORGANISM: Artificial Sequence
<220> FEATURE:
<223> OTHER INFORMATION: ADC7 DNA sequence
<220> FEATURE:
<221> NAME/KEY: misc_feature
<222> LOCATION: (441)..(441)
<223> OTHER INFORMATION: n is a, c, g, or t
<220> FEATURE:
<221> NAME/KEY: misc_feature
<222> LOCATION: (443)..(445)
<223> OTHER INFORMATION: n is a, c, g, or t

<400> SEQUENCE: 10

```
tttagtttta gcgtttagcg catcggcgga ctacaaagag gcccagccgg ccatggacct    60
gggtaagaaa ctgctggaag ctgctcgtgc tggtcaggac gacgaagttc gtatcctgat   120
ggctaacggt gctgacgtta acgctcgtga cgtttctggt gctactccac tgcacctggc   180
tgctacttgg ggtcacctgg aaatcgttga agttctgctg aagtacggtg ctgacgttaa   240
cgctcaggac aaattcggta agaccgcttt cgacatctcc atcgacaacg gtaacgagga   300
cctggctgaa atcctgcaag cggccgcaca tcatcatcac catcacgggg ccgcagaaca   360
aaaactcatc tcagaagagg atctgaatgg ggccgcatag actgttgaaa gttgtttagc   420
aaaacctcat acagaaaatt nannnactaa cgtctggaaa gacgacaaaa ctttagatcg   480
ttacgctaac tatgagggct gtctgtggaa tgctacaggc gttgtggttt gtactggtga   540
cgaaactcag tgttacggta catgggttcc tattgggctt gctatccctg aaaatgaggg   600
```

<210> SEQ ID NO 11
<211> LENGTH: 138
<212> TYPE: PRT
<213> ORGANISM: Artificial Sequence
<220> FEATURE:
<223> OTHER INFORMATION: ADC7
<220> FEATURE:
<221> NAME/KEY: misc_feature
<222> LOCATION: (5)..(6)
<223> OTHER INFORMATION: Xaa can be any naturally occurring amino acid

<400> SEQUENCE: 11

```
Trp Leu Ala Leu Xaa Xaa Leu Val Leu Ala Phe Ser Ala Ser Ala Asp
1               5                   10                  15

Tyr Lys Glu Ala Gln Pro Ala Met Asp Leu Gly Lys Lys Leu Leu Glu
            20                  25                  30

Ala Ala Arg Ala Gly Gln Asp Asp Glu Val Arg Ile Leu Met Ala Asn
        35                  40                  45

Gly Ala Asp Val Asn Ala Arg Asp Val Ser Gly Ala Thr Pro Leu His
    50                  55                  60

Leu Ala Ala Thr Trp Gly His Leu Glu Ile Val Glu Val Leu Leu Lys
65                  70                  75                  80

Tyr Gly Ala Asp Val Asn Ala Gln Asp Lys Phe Gly Lys Thr Ala Phe
                85                  90                  95

Asp Ile Ser Ile Asp Asn Gly Asn Glu Asp Leu Ala Glu Ile Leu Gln
            100                 105                 110

Ala Ala Ala His His His His His His Gly Ala Ala Glu Gln Lys Leu
        115                 120                 125

Ile Ser Glu Glu Asp Leu Asn Gly Ala Ala
    130                 135
```

<210> SEQ ID NO 12
<211> LENGTH: 720
<212> TYPE: DNA
<213> ORGANISM: Artificial Sequence
<220> FEATURE:
<223> OTHER INFORMATION: PDA6 DNA sequence
<220> FEATURE:
<221> NAME/KEY: misc_feature
<222> LOCATION: (1)..(11)
<223> OTHER INFORMATION: n is a, c, g, or t
<220> FEATURE:
<221> NAME/KEY: misc_feature
<222> LOCATION: (14)..(16)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t

<400> SEQUENCE: 12

```
nnnnnnnnnn ntgnnnttct anttcnggag anagtcatag ctagcatgaa aaagatttgn      60
ctggcgctgg ctggtttagt tttagcgttt agcgcatcgg cggactacaa agaggcccag     120
ccggccatgg acctgggtaa gaaactgctg gaagctgctc gtgctggtca ggacgacgaa     180
gttcgtatcc tgatggctaa cggtgctgac gttaacgctc aggacactaa aggttacact     240
ccgctgcacc tggctgctaa ctctggtcac ctggaaatcg ttgaagttct gctgaagaac     300
```

```
ggtgctgacg ttaacgctca ggacaaattc ggtaagaccg ctttcgacat ctccatcgac    360
aacggtaacg aggacctggc tgaaatcctg caagcggccg cacatcatca tcaccatcac    420
ggggccgcag aacaaaaact catctcagaa gaggatctga atggggccgc atagactgtt    480
gaaagttgtt tagcaaaacc tcatacagaa aattcattta ctaacgtctg gaaagacgac    540
aaaactttag atcgttacgc taactatgag ggctgtctgt ggaatgctac aggcgttgtg    600
gtttgtactg gtgacgaaac tcagtgttac ggtacatggg ttcctattgg gcttgctatc    660
cctgaaaatg agggtggtgg ctctgagggt ggcggttctg agggtggcgg ttctgagggt    720
```

<210> SEQ ID NO 13
<211> LENGTH: 146
<212> TYPE: PRT
<213> ORGANISM: Artificial Sequence
<220> FEATURE:
<223> OTHER INFORMATION: PDA6 protein sequence
<220> FEATURE:
<221> NAME/KEY: misc_feature
<222> LOCATION: (9)..(9)
<223> OTHER INFORMATION: Xaa can be any naturally occurring amino acid

<400> SEQUENCE: 13

Val Ile Ala Ser Met Lys Lys Ile Xaa Leu Ala Leu Ala Gly Leu Val
1               5                   10                  15

Leu Ala Phe Ser Ala Ser Ala Asp Tyr Lys Glu Ala Gln Pro Ala Met
            20                  25                  30

Asp Leu Gly Lys Lys Leu Leu Glu Ala Ala Arg Ala Gly Gln Asp Asp
        35                  40                  45

Glu Val Arg Ile Leu Met Ala Asn Gly Ala Asp Val Asn Ala Gln Asp
    50                  55                  60

Thr Lys Gly Tyr Thr Pro Leu His Leu Ala Ala Asn Ser Gly His Leu
65                  70                  75                  80

Glu Ile Val Glu Val Leu Leu Lys Asn Gly Ala Asp Val Asn Ala Gln
                85                  90                  95

Asp Lys Phe Gly Lys Thr Ala Phe Asp Ile Ser Ile Asp Asn Gly Asn
            100                 105                 110

Glu Asp Leu Ala Glu Ile Leu Gln Ala Ala His His His His His His
        115                 120                 125

His Gly Ala Ala Glu Gln Lys Leu Ile Ser Glu Glu Asp Leu Asn Gly
    130                 135                 140

Ala Ala
145

<210> SEQ ID NO 14
<211> LENGTH: 671
<212> TYPE: DNA
<213> ORGANISM: Artificial Sequence
<220> FEATURE:
<223> OTHER INFORMATION: PDA8 DNA sequence

<400> SEQUENCE: 14

```
atttggctgg cgctggctgg tttagttta gcgtttagcg catcggcgga ctacaaagag    60
gcccagccgg ccatggacct gggtaagaaa ctgctggaag ctgctcgtgc tggtcaggac    120
gacgaagttc gtatcctgat ggctaacggt gctgacgtta acgctcagga cgaagctggt    180
ctgactccgc tgcacctggc tgctaaaaac ggtcacctgg aaatcgttga agttctgctg    240
aagaacggtg ctgacgttaa cgctcaggac aaattcggta agaccgcttt cgacatctcc    300
```

```
atcgacaacg gtaacgagga cctggctgaa atcctgcaag cggccgcaca tcatcatcac    360
catcacgggg ccgcagaaca aaaactcatc tcagaagagg atctgaatgg ggccgcatag    420
actgttgaaa gttgtttagc aaaacctcat acagaaaatt catttactaa cgtctggaaa    480
gacgacaaaa ctttagatcg ttacgctaac tatgagggct gtctgtggaa tgctacaggc    540
gttgtggttt gtactggtga cgaaactcag tgttacggta catgggttcc tattgggctt    600
gctatccctg aaaatgaggg tggtggctct gagggtggcg ttctgaggg tggcggttct    660 gagggtggcg g                                                         671
```

<210> SEQ ID NO 15
<211> LENGTH: 139
<212> TYPE: PRT
<213> ORGANISM: Artificial Sequence
<220> FEATURE:
<223> OTHER INFORMATION: PDA8 protein sequence

<400> SEQUENCE: 15

```
Ile Trp Leu Ala Leu Ala Gly Leu Val Leu Ala Phe Ser Ala Ser Ala
  1               5                  10                  15

Asp Tyr Lys Glu Ala Gln Pro Ala Met Asp Leu Gly Lys Lys Leu Leu
             20                  25                  30

Glu Ala Ala Arg Ala Gly Gln Asp Asp Glu Val Arg Ile Leu Met Ala
         35                  40                  45

Asn Gly Ala Asp Val Asn Ala Gln Asp Glu Ala Gly Leu Thr Pro Leu
     50                  55                  60

His Leu Ala Ala Lys Asn Gly His Leu Glu Ile Val Glu Val Leu Leu
 65                  70                  75                  80

Lys Asn Gly Ala Asp Val Asn Ala Gln Asp Lys Phe Gly Lys Thr Ala
                 85                  90                  95

Phe Asp Ile Ser Ile Asp Asn Gly Asn Glu Asp Leu Ala Glu Ile Leu
            100                 105                 110

Gln Ala Ala Ala His His His His His His Gly Ala Ala Glu Gln Lys
        115                 120                 125

Leu Ile Ser Glu Glu Asp Leu Asn Gly Ala Ala
    130                 135
```

<210> SEQ ID NO 16
<211> LENGTH: 667
<212> TYPE: DNA
<213> ORGANISM: Artificial Sequence
<220> FEATURE:
<223> OTHER INFORMATION: PDA9 DNA Sequence

<400> SEQUENCE: 16

```
ttggctggcg ctggctggtt tagttttagc gtttagcgca tcggcggact acaaagaggc     60
ccagccggcc atggacctgg gtaagaaact gctggaagct gctcgtgctg gtcaggacga    120
cgaagttcgt atcctgatgg ctaacggtgc tgacgttaac gctgacgacc agttcgtga    180 cactccgctg cacctggctg ctatgactgg tcacctggaa atcgttgaag ttctgctgaa    240
gaacggtgct gacgttaacg ctcaggacaa attcggtaag accgctttcg acatctccat    300
cgacaacggt aacgaggacc tggctgaaat cctgcaagcg gccgcacatc atcatcacca    360
tcacggggcc gcagaacaaa aactcatctc agaagaggat ctgaatgggg ccgcatagac    420
tgttgaaagt gtttagcaa aacctcatac agaaaattca tttactaacg tctggaaaga    480
cgacaaaact ttagatcgtt acgctaacta tgagggctgt ctgtggaatg ctacaggcgt    540
```

```
tgtggtttgt actggtgacg aaactcagtg ttacggtaca tgggttccta ttgggcttgc    600
tatccctgaa aatgagggtg gtggctctga gggtggcggt tctgagggtg gcggttctga    660
gggtggc                                                              667
```

<210> SEQ ID NO 17
<211> LENGTH: 138
<212> TYPE: PRT
<213> ORGANISM: Artificial Sequence
<220> FEATURE:
<223> OTHER INFORMATION: PDA9 protein

<400> SEQUENCE: 17

```
Trp Leu Ala Leu Ala Gly Leu Val Leu Ala Phe Ser Ala Ser Ala Asp
 1               5                  10                  15
Tyr Lys Glu Ala Gln Pro Ala Met Asp Leu Gly Lys Lys Leu Leu Glu
             20                  25                  30
Ala Ala Arg Ala Gly Gln Asp Asp Glu Val Arg Ile Leu Met Ala Asn
         35                  40                  45
Gly Ala Asp Val Asn Ala Asp Asp Gln Phe Gly Asp Thr Pro Leu His
     50                  55                  60
Leu Ala Ala Met Thr Gly His Leu Glu Ile Val Glu Val Leu Leu Lys
 65                  70                  75                  80
Asn Gly Ala Asp Val Asn Ala Gln Asp Lys Phe Gly Lys Thr Ala Phe
                 85                  90                  95
Asp Ile Ser Ile Asp Asn Gly Asn Glu Asp Leu Ala Glu Ile Leu Gln
            100                 105                 110
Ala Ala Ala His His His His His His Gly Ala Ala Glu Gln Lys Leu
        115                 120                 125
Ile Ser Glu Glu Asp Leu Asn Gly Ala Ala
    130                 135
```

<210> SEQ ID NO 18
<211> LENGTH: 600
<212> TYPE: DNA
<213> ORGANISM: Artificial Sequence
<220> FEATURE:
<223> OTHER INFORMATION: PDC1 DNA sequence

<400> SEQUENCE: 18

```
ggctggcgct ggctggttta gttttagcgt ttagcgcatc ggcggactac aaagaggccc    60
agccggccat ggacctgggt aagaaactgc tggaagctgc tcgtgctggt caggacgacg    120
aagttcgtat cctgatggct aacggtgctg acgttaacgc tgctgacgtt aaaggtgaaa    180
ctccgctgca cctggctgct tgggacggtc acctggaaat cgttgaagtt ctgctgaaga    240
acggtgctga cgttaacgct caggacaaat tcggtaagac cgctttcgac atctccatcg    300
acaacggtaa cgaggacctg gctgaaatcc tgcaagcggc cgcacatcat catcaccatc    360
acggggccgc agaacaaaaa ctcatctcag aagaggatct gaatgggccg catagactg    420 ttgaaagttg tttagcaaaa cctcatacag aaaattcatt tactaacgtc tggaaagacg    480
acaaaacttt agatcgttac gctaactatg agggctgtct gtggaatgct acaggcgttg    540
tggtttgtac tggtgacgaa actcagtgtt acggtacatg ggttcctatt gggcttgcta    600
```

<210> SEQ ID NO 19
<211> LENGTH: 140
<212> TYPE: PRT
<213> ORGANISM: Artificial Sequence
<220> FEATURE:

```
<223> OTHER INFORMATION: PDC1 protein sequence

<400> SEQUENCE: 19

Lys Ile Trp Leu Ala Leu Ala Gly Leu Val Leu Ala Phe Ser Ala Ser
1               5                   10                  15

Ala Asp Tyr Lys Glu Ala Gln Pro Ala Met Asp Leu Gly Lys Lys Leu
            20                  25                  30

Leu Glu Ala Ala Arg Ala Gly Gln Asp Asp Glu Val Arg Ile Leu Met
        35                  40                  45

Ala Asn Gly Ala Asp Val Asn Ala Ala Asp Val Lys Gly Glu Thr Pro
    50                  55                  60

Leu His Leu Ala Ala Trp Asp Gly His Leu Glu Ile Val Glu Val Leu
65                  70                  75                  80

Leu Lys Asn Gly Ala Asp Val Asn Ala Gln Asp Lys Phe Gly Lys Thr
                85                  90                  95

Ala Phe Asp Ile Ser Ile Asp Asn Gly Asn Glu Asp Leu Ala Glu Ile
            100                 105                 110

Leu Gln Ala Ala Ala His His His His His His Gly Ala Ala Glu Gln
        115                 120                 125

Lys Leu Ile Ser Glu Glu Asp Leu Asn Gly Ala Ala
    130                 135                 140
```

DARPIN REAGENTS THAT DISTINGUISH ALZHEIMER'S DISEASE AND PARKINSON'S DISEASE SAMPLES

CROSS REFERENCE TO RELATED APPLICATION

This disclosure claims the benefit of the earlier filing date of U.S. Provisional Application No. 62/798,381, filed Jan. 29, 2019, which is hereby incorporated by reference in its entirety.

STATEMENT OF GOVERNMENT SUPPORT

This invention was made with government support under R21 NS061257 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jan. 12, 2020, is named 131849-252127_ST25.txt and is 22,000 bytes in size.

FIELD OF THE DISCLOSURE

The present disclosure relates to diagnostics for neurodegenerative diseases, and in particular to design ankyrin repeat protein (DARPins) reagents that distinguish Alzheimer's disease (AD) from Parkinson's disease (PD).

BACKGROUND

There is an urgent need for reagents that can recognize biomarkers that are unique to different neurodegenerative diseases. Reagents that can distinguish AD from PD as well as from other neurodegenerative diseases are crucial. This is particularly important since recent studies have indicated that AD and PD may require a personalized diagnostic approach. As such, a more personalized diagnostic test is needed for any treatment plan to be effective.

SUMMARY

Disclosed herein are compositions, methods and assays for diagnosing, monitoring and developing a therapeutic treatment plan for a subject with a neurodegenerative disease, including, but not limited to AD, PD or AML. In particular, disclosed herein are diagnostic DARPin reagents for identifying subjects who have or are at risk of acquiring a neurodegenerative disease, such as AD or PD, monitoring the effectiveness of treatments for a neurodegenerative disease, such as AD or PD, and treating specific neurodegenerative diseases, including AD or PD. Also disclosed are diagnostic assays that can be used to diagnose or monitor the efficacy of a neurodegenerative disease treatment.

In some embodiments, a method, comprises detecting an increase in at least one neurodegenerative disease-associated DARPin in a biological sample as compared to a control sample, thereby identifying the neurodegenerative disease in the biological sample or determining the efficacy of therapy for the neurodegenerative disease.

In some embodiments, the neurodegenerative disease is AD and the method is for identifying AD in the biological sample or determining the efficacy of therapy for the AD and wherein the at least one neurodegenerative disease-associated DARPin is an AD-associated DARPin.

In some embodiments, the at least one AD-associated DARPin is ADC1, ADC3, ADC6, and/or ADC7.

In some embodiments, detecting of ADC1, ADC3, ADC6, and/or ADC7 comprises usage of at least one antibody specific for at least one of ADC1, ADC3, ADC6, and/or ADC7.

In some embodiments, detecting ADC1, ADC3, ADC6, and/or ADC7 with at least one antibody specific for at least one of ADC1, ADC3, ADC6, and/or ADC7 comprises using an ELISA.

In some embodiments, the neurodegenerative disease is Parkinson's Disease (PD) and the method is for identifying PD in the biological sample or determining the efficacy of therapy for the PD and the at least one neurodegenerative disease-associated DARPin is a PD-associated DARPin.

In some embodiments, the at least one PD-associated DARPin is PDA6, PDA8, PDA9, and/or PDC1.

In some embodiments, detecting of PDA6, PDA8, PDA9, and/or PDC1 comprises usage of at least one antibody specific for at least one of PDA6, PDA8, PDA9, and/or PDC1.

In some embodiments, detecting PDA6, PDA8, PDA9, and/or PDC1 with at least one antibody specific for at least one of PDA6, PDA8, PDA9, and/or PDC1 comprises using an ELISA.

In some embodiments, a kit for detecting a neurodegenerative disease or monitoring the efficacy of a neurodegenerative treatment, comprising at least one molecule capable of detecting at least one neurodegenerative-associated DARPin and directions for using the kit.

In some embodiments, the kit includes at least one positive and negative control and at least one antibody capable of binding at least one DARPin specific for detecting AD and/or one DARPin specific for detecting PD.

In some embodiments, the kit includes an ELISA.

In some embodiments of the kit, the at least one DARPin specific for AD is ADC1, ADC3, ADC6, and/or ADC7.

In some embodiments of the kit, the at least one DARPin specific for PD is PDA6, PDA8, PDA9, and/or PDC1.

The foregoing and other features of the disclosure will become more apparent from the following detailed description, which proceeds with reference to the accompanying figures.

BRIEF DESCRIPTION OF THE DRAWINGS

FIG. 1 illustrates the generic protein sequences and other details of the DARPins library disclosed herein;

FIG. 4 provides Table 1.

DETAILED DESCRIPTION

Figure 2:
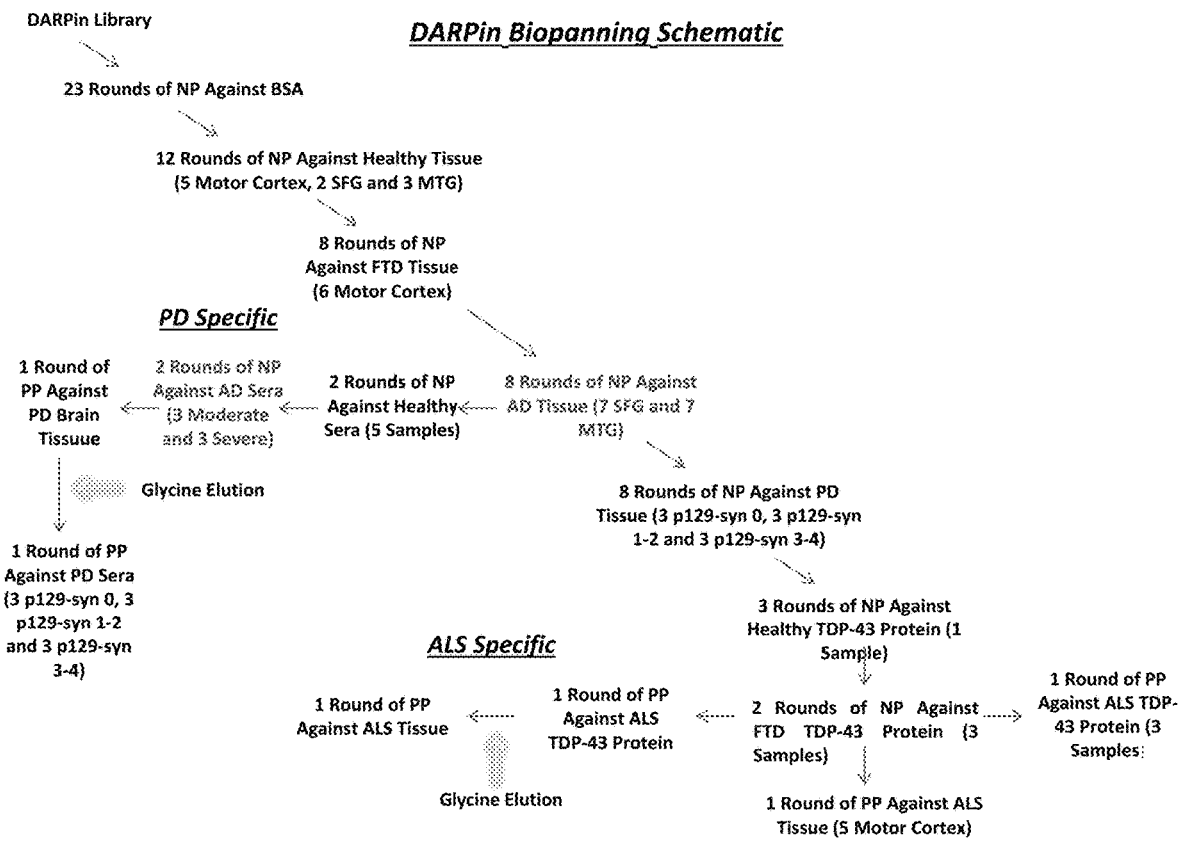
FIGS. 2 and 3 provide DARPin Biopanning schematics in accordance with the exemplary methods disclosed herein (NP: negative panning; PP: positive panning).

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Unless otherwise noted, technical terms are used according to conventional usage. Definitions of common terms in molecular biology can be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710); and other similar references. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Terms. To facilitate review of the various embodiments of this disclosure, the following explanations of specific terms are provided, along with particular examples:

Alzheimer's disease (AD): A progressive brain disorder that occurs gradually and results in memory loss, behavioral and personality changes, and a decline in mental abilities. These losses are related to the death of brain cells and the breakdown of the connections between them. The course of this disease varies from person to person, as does the rate of decline. On average, AD patients live for 8 to 10 years after they are diagnosed, though the disease can last up to 20 years. AD advances by stages, from early, mild forgetfulness to a severe loss of mental function. At first, AD destroys neurons in parts of the brain that control memory, especially in the hippocampus and related structures. As nerve cells in the hippocampus stop functioning properly, short-term memory fails. AD also attacks the cerebral cortex, particularly the areas responsible for language and reasoning.

Amyotrophic lateral sclerosis (ALS): A progressive, usually fatal, neurodegenerative disease caused by the degeneration of motor neurons. As a motor neuron disease, the disorder causes muscle weakness and atrophy throughout the body as both the upper and lower motor neurons degenerate, ceasing to send messages to muscles. Unable to function, the muscles gradually weaken, develop fasciculations (twitches) because of denervation, and eventually atrophy because of that denervation. The patient may ultimately lose the ability to initiate and control all voluntary movement except for the eyes. ALS is also known as Lou Gehrig's disease.

Animal: Living multi-cellular vertebrate organisms, a category that includes, for example, mammals and birds. The term mammal includes both human and non-human mammals. Similarly, the term "subject" includes both human and veterinary subjects.

Axonal disorder: A disorder associated with axon damage. Axon damage includes axon degeneration and a reduction in axon density, for example in the white matter of the caudal spinal cord. White matter tissue damage includes axons undergoing Wallerian-like degeneration, reduced nerve fiber density, and demyelination. White matter tissue damage can be determined by histological examination of white matter, for example from the ventrolateral or dorsal thoracic spinal cord. White matter tissue damage may also be determined by MRI. Evidence of axonal damage can be inferred from presence of abnormal MRI signals, such as permanently decreased T signals ("black holes"), decreased n-acetyl aspartate (NAA) and whole brain atrophy.

In one example, the axonal disorder is a disorder associated with proximal giant axonopathy. In some examples, an axonal disorder is a neuropathy associated with exposure to a neurotoxic solvent that form a gamma-diketone compound (such as n-hexane), solvent (1,2-diethylbenzene and/or n-hexane, or gamma-diketone) neuropathy, or neuropathies associated with production of protein adducts molecules (such as gamma-keto-aldehydes, oxidative metabolities of arachidonic acid), ALS (Lou Gehrig's), Alzheimer's, Corticobasal degeneration, Creutzfeldt-Jakob disease, familial fatal insomnia, frontotemporal lobar degeneration, Huntington's disease, HIV-associated dementia, Kennedy's disease, Krabbe's disease, Lewy body dementia disease, diabetic neuropathy, uremic neuropathy (kidney failure), dementia, multiple sclerosis, konzo, tropical ataxic neuropathy, Parkinson's disease (PD), ALS/PD, Lathyrsism, primary lateral sclerosis, or spinal muscular atrophy or a combination thereof.

Contacting: "Contacting" includes in solution and solid phase, for example contacting a salivary protein with a test agent. The test agent may also be a combinatorial library for screening a plurality of compounds. In another example, contacting includes contacting a sample with an antibody, for example contacting a sample that contains a protein of interest such as a protein associated with a neurodegenerative disease, such as AD, PD or AML.

Control: A "control" refers to a sample or standard used for comparison with an experimental sample, such as a biological sample obtained from a healthy subject or a non-AD or PD sample. A control can also be a historical control or standard reference value or range of values (i.e. a previously tested control sample or group of samples that represent baseline or normal values).

Design ankyrin repeat proteins (DARPins): Genetically engineered antibody mimetic proteins typically exhibiting highly specific and high-affinity target protein binding. They are derived from natural ankyrin proteins which are responsible for diverse functions such as cell signaling, regulation and structural integrity of the cell. DARPins consist of at least three, repeat motifs proteins, and usually consist of four or five. Their molecular mass is about 14 or 18 kDa (kilodaltons) for four- or five-repeat DARPins, respectively. DARPins constitute a new class of potent, specific and versatile small-protein therapies, and are used as investigational tools in various research, diagnostic and therapeutic applications as disclosed herein.

Diagnostic: Identifying the presence or nature of a pathologic condition, such as, but not limited to, an infection with a pathogen. Diagnostic methods differ in their sensitivity and specificity. The "sensitivity" of a diagnostic assay is the percentage of diseased individuals who test positive (percent of true positives). The "specificity" of a diagnostic assay is 1 minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" means predicting the probability of development (for example, severity) of a pathologic condition.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see e.g., Bitter et al., Methods in Enzymology 153:516-544, 1987). For example, when cloning in bacterial systems, inducible promoters such as pL of bacteriophage lambda, plac, ptrp, ptac (ptrp-lac hybrid promoter) and the like can be used. In one embodiment, when cloning in mammalian cell systems, promoters derived from the genome of mammalian cells (such as the metallothionein promoter) or from mammalian viruses (such as the retrovirus long terminal repeat; the adenovirus late promoter; the vaccinia virus 7.5K promoter) can be used. Promoters produced by recombinant DNA or synthetic techniques can also be used to provide for transcription of the nucleic acid sequences.

Host cells: Cells in which a vector can be propagated and its DNA expressed. The cell may be prokaryotic or eukaryotic. The cell can be mammalian, such as a human cell. The term also includes any progeny of the subject host cell. It is understood that all progeny may not be identical to the parental cell since there may be mutations that occur during replication. However, such progeny are included when the term "host cell" is used.

Increase: To increase the quality, amount, or strength of something. In some examples, an increase in the level of a particular DARPin is associated with a particular condition or disease. In certain examples, production of a DARPin increases by at least 2-fold, for example at least 3-fold or at least 4-fold, as compared to a control (such an amount of the DARPin in a subject without a neurodegenerative disease, such as without AD or PD). Such increases can be measured using the methods disclosed herein. For example, "detecting or measuring a DARPin" includes quantifying the amount of the DARPin present in a sample. Quantification can be either numerical or relative. Detecting can be achieved using any method known in the art or described herein, such as by ELISA. Controls or standards for comparison to a sample include samples believed to be normal (in that they are not altered for the desired characteristic, for example a sample from a subject who does not have a neurodegenerative disease, such as AD or PD) as well as laboratory values (e.g., range of values), even though possibly arbitrarily set, keeping in mind that such values can vary from laboratory to laboratory.

Laboratory standards and values can be set based on a known or determined population value and can be supplied in the format of a graph or table that permits comparison of measured, experimentally determined values. In some embodiments of the methods, the increase is of a diagnostically significant amount, which refers to a change of a sufficient magnitude to provide a statistical probability of the diagnosis.

Isolated: An "isolated" biological component (such as a nucleic acid or protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule to facilitate detection of that molecule. Specific, non-limiting examples of labels include fluorescent tags, enzymatic linkages, and radioactive isotopes. In some examples a disclosed DARPin that specifically binds to AD or PD associated molecules is labeled. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998), Harlow & Lane (Antibodies, *A Laboratory Manual*, Cold Spring Harbor Publications, New York, 1988).

Lewy body dementia (LBD): A disease associated with abnormal deposits of a protein called alpha-synuclein in the brain. These deposits, called Lewy bodies, affect chemicals in the brain whose changes, in turn, can lead to problems with thinking, movement, behavior, and mood.

Neurodegenerative disease: Refers to any type of disease that is characterized by the progressive deterioration of the nervous system.

Parkinson's disease (PD): An idiopathic, slowly progressive, degenerative CNS disorder characterized by slow and decreased movement, muscular rigidity, resting tremor, and postural instability. The loss of substantia nigra neurons, which project to the caudate nucleus and putamen, results in the depletion of the neurotransmitter dopamine in these areas.

Polypeptide: Any chain of amino acids, regardless of length or post-translational modification (e.g., glycosylation or phosphorylation). A polypeptide can be between 3 and 30 amino acids in length. In one embodiment, a polypeptide is from about 5 to about 25 amino acids in length. In yet another embodiment, a polypeptide is from about 8 to about 12 amino acids in length. In yet another embodiment, a peptide is about 5 amino acids in length. With regard to polypeptides, the word "about" indicates integer amounts.

Peptide Modifications: A term that includes synthetic embodiments of peptides described herein. In addition, analogs (non-peptide organic molecules), derivatives (chemically functionalized peptide molecules obtained starting with the disclosed peptide sequences) and variants (homologs) of these proteins can be utilized in the methods described herein. Each polypeptide of this disclosure is comprised of a sequence of amino acids, which may be either L and/or D-amino acids, naturally occurring and otherwise.

Peptides can be modified by a variety of chemical techniques to produce derivatives having essentially the same activity as the unmodified peptides, and optionally having other desirable properties. For example, carboxylic acid groups of the protein, whether carboxyl-terminal or side chain, can be provided in the form of a salt of a pharmaceutically-acceptable cation or esterified to form a C1-C16 ester, or converted to an amide of formula NR1R2 wherein R1 and R2 are each independently H or C1-C16 alkyl, or combined to form a heterocyclic ring, such as a 5- or 6-membered ring. Amino groups of the peptide, whether amino-terminal or side chain, can be in the form of a pharmaceutically-acceptable acid addition salt, such as the HCl, HBr, acetic, benzoic, toluene sulfonic, maleic, tartaric and other organic salts, or can be modified to C1-C16 alkyl or dialkyl amino or further converted to an amide.

Hydroxyl groups of the peptide side chains may be converted to C1-C16 alkoxy or to a C1-C16 ester using well-recognized techniques. Phenyl and phenolic rings of the peptide side chains may be substituted with one or more halogen atoms, such as fluorine, chlorine, bromine or iodine, or with C1-C16 alkyl, C1-C16 alkoxy, carboxylic acids and esters thereof, or amides of such carboxylic acids. Methylene groups of the peptide side chains can be extended to homologous C2-C4 alkylenes. Thiols can be protected with any one of a number of well-recognized protecting groups, such as acetamide groups. Those skilled in the art will also recognize methods for introducing cyclic structures into the peptides of this disclosure to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the peptide backbone and component amino acid side chains, resulting in such peptido- and organomimetics. For computer modeling applications, a pharmacophore is an idealized three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs," in Klegerman & Groves, eds., 1993, Pharmaceutical Biotechnology, Interpharm Press: Buffalo Grove, Ill., pp. 165 174 and Principles of Pharmacology, Munson (ed.) 1995, Ch. 102, for descriptions of techniques used in CADD. Also included are mimetics prepared using such techniques.

Sample (or biological sample): A biological specimen containing genomic DNA, RNA (including mRNA), protein, or combinations thereof, obtained from a subject. Examples include, but are not limited to, peripheral blood, urine, saliva, tissue biopsy, fine needle aspirate, punch biopsy surgical specimen, and autopsy material.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Within the context of a peptide, a "conserved residue" is one which appears in a significantly higher frequency than would be expected by random distribution at a particular position in a peptide.

Methods of alignment of sequences for comparison are well known in the art. Various programs and alignment algorithms are described in: Smith and Waterman, Adv. Appl. Math. 2:482, 1981; Needleman and Wunsch, J. Mol. Biol. 48:443, 1970; Higgins and Sharp, Gene 73:237, 1988; Higgins and Sharp, CABIOS 5:151, 1989; Corpet et al., Nucleic Acids Research 16:10881, 1988; and Pearson and Lipman, Proc. Natl. Acad. Sci. USA 85:2444, 1988. Altschul et al., Nature Genet. 6:119, 1994, presents a detailed consideration of sequence alignment methods and homology calculations.

The NCBI Basic Local Alignment Search Tool (BLAST) (Altschul et al., J. Mol. Biol. 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a polypeptide are typically characterized by possession of at least 75%, for example at least 80%, sequence identity counted over the full length alignment with the amino acid sequence using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Treating a disease: "Treatment" refers to a therapeutic intervention that ameliorates a sign or symptom of a disease or pathological condition related to the disease, such as the infection.

Suitable methods and materials for the practice or testing of this disclosure are described below. Such methods and materials are illustrative only and are not intended to be limiting. Other methods and materials similar or equivalent to those described herein can be used. For example, conventional methods well known in the art to which this disclosure pertains are described in various general and more specific references, including, for example, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999. In addition, the materials, methods, and examples are illustrative only and not intended to be limiting.

Compositions, Methods and Assays

Design ankyrin repeat proteins (DARPins) are stable structures for protein-protein interactions. Their stability is maintained even following connection of multiple repeats making them an attractive replacement for antibodies and single-chain variable fragments (scFvs). Herein, the inventors demonstrate that DARPins are excellent reagents for identifying biomarkers in different neurodegenerative diseases. Following creation of a new DARPins library, the inventors utilized a complex set of atomic forced microscopy based biopanning procedures. In particular, the biopanning procedures involved a complex set of negative biopanning steps to remove DARPins reactive with undesired targets and serial positive biopanning steps where the isolated DARPins were reactive with both human brain tissue and sera samples from AD or PD cases. Subsequent characterization experiments using ELISA and western blotting revealed AD and PD DARPins reactive with beta-amyloid, TAR-DNA binding protein 43, alpha-synuclein and tau. Moreover, further tests for cross-reactivity revealed that AD DARPins were highly selective for AD and PD DARPins were highly selective for PD. This type of selectivity is critical for more accurate distinction amongst neurodegenerative diseases and can be used in the development of an effective therapeutic treatment plan.

Based upon these findings, compositions, methods and assays of using such for diagnosing, monitoring and developing a therapeutic treatment plan for a subject with a axonal disorder such as a neurodegenerative disease, including, but not limited to AD, PD or AML, are disclosed. In particular, disclosed herein are diagnostic DARPin reagents for identifying subjects who have or at risk of acquiring a neurodegenerative disease, such as AD or PD, monitoring the effectiveness of treatments for a neurodegenerative disease, such as AD or PD, and treating specific neurodegenerative diseases, including AD or PD. Also disclosed are diagnostic assays that can be used to diagnose or monitor the efficacy of a neurodegenerative disease treatment.

A. Methods

The methods disclosed herein utilize a biological fluid, such as, but not limited to urine or serum, for the detection of a molecule associated with a neurodegenerative disease, including, but not limited to, molecules detected by AD or PD specific DARPins disclosed herein. These methods can be performed over time, to monitor the progression or regression of the neurodegenerative disease in a subject, or to assess for the development of the neurodegenerative disease, such as AD or PD, from a pre-symptomatic condition.

In particular, methods are disclosed herein that are of use to determine if a subject has an AD-associated or PD-associated condition or to monitor the efficacy of therapy. These methods utilize a sample, such as a biological fluid, including, but not limited to urine or serum, for the detection of a molecule associated with an AD-associated or PD-associated condition, including, but not limited to, ADC1, ADC3, ADC6, and/or ADC7 or any combination thereof for an AD-associated condition and PDA6, PDA8, PDA9, and/or PDC1 or any combination thereof for a PD-associated condition, respectively. It is contemplated that fragments of ADC1, ADC3, ADC6, and/or ADC7, PDA6, PDA8, PDA9, and/or PDC1 can be used in addition to the specific sequences provided for each herein. For examples, molecules with at least 85%, such as between 85%-99%, 95%-99%, including 85%, 86%, 87%, 88%, 89%, 90%, 91%, 92%, 93%, 94%, 95%, 96%, 97%, 98%, 99%, or 100% sequence identity to sequences of ADC1, ADC3, ADC6, ADC7, PDA6, PDA8, PDA9, and/or PDC1 disclosed herein.

In some embodiments, the methods disclosed herein are used to identify a subject as having a neurodegenerative disorder and/or disease. In some embodiments, the methods are used to identify and/or diagnose a subject with AD. In some embodiments, the methods are used to identify and/or diagnose a subject with PD. These methods can be performed over time, to monitor the progression or regression of an AD-associated or PD-associated condition or disease in a subject, or to assess for the development of an AD-associated or PD-associated condition. In some examples, the disclosed methods are used for self-monitoring.

Methods are disclosed herein that include testing a biological sample, such as a serum or urine sample, obtained from the subject. In one example, the biological sample is serum. However, other biological samples are also of use, such as blood (such as whole blood obtained from a finger prick), GCF, amniotic fluid, BALF, saliva, tissue biopsy or tears. The methods include detecting, or determining the abundance (amount) of one or more molecules associated with an AD or PD condition, including but not limited to, ADC1, ADC3, ADC6, and/or ADC7 or any combination thereof for an AD-associated condition and PDA6, PDA8, PDA9, and/or PDC1 or any combination thereof for a PD-associated condition, respectively. In one example, the method includes detecting at least one DARPin selected from, but not limited to, ADC1, ADC3, ADC6, or ADC7 for an AD-associated condition. In one example, the method includes detecting at least one DARPin selected from, but not limited to, PDA6, PDA8, PDA9, or PDC1 for a PD-associated condition, respectively.

In some examples, the methods include detecting at least one, such as at least two, at least three, or at least four molecules associated with an AD-associated condition or disease. In one example, the method includes detecting at least one, such as at least two, at least three, or at least four, such as one, two, three, four or more AD-associated molecules disclosed herein, including ADC1, ADC3, ADC6, or ADC7. In some examples, the methods include detecting at least one, such as at least two, at least three, or at least four molecules associated with a PD-associated condition or disease. In one example, the method includes detecting at least one, such as at least two, at least three, or at least four, such as one, two, three, four or more PD-associated molecules disclosed herein, including PDA6, PDA8, PDA9, and PDC1.

In some embodiments, the method includes detecting an increase, such as a statistically significant increase, such as at least a 1.5, 2, 3, 4, or 5 fold increase in the amount of one or more molecules associated with an AD-associated or PD-associated condition or disease, including at least a 1.5, at least a 2, at least a 3, at least a 4, or at least a 5, such as a 1.5, 2, 2.5, 3, 3.5, 4, 5 fold increase in one or more AD-associated or PD-associated molecules, such as one or more AD molecules (ADC1, ADC3, ADC6, and/or ADC7) or PD molecules (PDA6, PDA8, PDA9, or PDC1) disclosed herein as compared to a control/reference value.

In one embodiment, the method includes comparing a test sample of serum from a subject of interest possibly comprising at least one of protein associated with AD or PD, such as an AD or PD protein disclosed herein, such as ADC1, ADC3, ADC6, or ADC7 for AD or PDA6, PDA8, PDA9, or PDC1 for PD or all of these molecules with a reference sample.

In one embodiment, the method determines if the subject has AD. If the reference sample is a control sample without AD and the profile of the test sample is essentially the same as the profile of the control sample, the subject is determined not to have an AD-associated condition or disease. However, if the profile of the test sample has an increase in AD-associated molecules relative to the control sample the subject is determined to have an AD-associated condition or disease.

In one embodiment, the method determines if the subject has PD. If the reference sample is a control sample without PD and the profile of the test sample is essentially the same as the profile of the control sample, the subject is determined not to have a PD-associated condition or disease. However, if the profile of the test sample has an increase in PD-associated molecules relative to the control sample the subject is determined to have a PD-associated condition or disease.

In one example, detecting at least one AD or PD-associated molecule comprises using a lateral flow device or test/dip strip.

In one embodiment, the method is a method to determine if a therapy is effective for the treatment of the subject by detecting the presence of at least one molecule associated with the particular neurodegenerative disease, such as AD or PD. The method can be performed multiple times over a specified time period, such as days, weeks, months or years. In several examples, the therapy includes treatment with a therapeutic agent for AD or PD. If the reference sample is a sample from a non-AD or PD subject, and the test sample is essentially the same as the normal sample the subject is determined to have an effective therapy, while if the test sample has an increase in AD or PD-associated molecules relative to the control sample, the subject is determined to have an ineffective therapy. Changes in the profile can also represent the progression (or regression) of the disease process.

The diagnostic methods of the present disclosure are valuable tools for practicing physicians to make quick treatment decisions for neurodegenerative conditions, including both AD and PD. These treatment decisions can include the administration of AD or PD specific modulatory agents and decisions to monitor a subject for onset and/or advancement of the specific condition/disease. The methods disclosed herein can also be used to monitor the effectiveness of a therapy.

Following the measurement of the expression levels of one or more of the molecules identified herein, the assay results, findings, diagnoses, predictions and/or treatment recommendations are typically recorded and communicated to technicians, physicians and/or patients, for example. In certain embodiments, computers will be used to communicate such information to interested parties, such as, patients and/or the attending physicians. Based on the measurement, the therapy administered to a subject can be modified.

In one embodiment, a diagnosis, prediction and/or treatment recommendation based on the expression level in a test subject of one or more of the AD or PD associated molecules is communicated to the subject as soon as possible after the assay is completed and the diagnosis and/or prediction is generated. The results and/or related information may be communicated to the subject by the subject's treating physician. Alternatively, the results may be communicated directly to a test subject by any means of communication, including writing, such as by providing a written report, electronic forms of communication, such as email, or telephone. Communication may be facilitated by use of a computer, such as in case of email communications. In certain embodiments, the communication containing results of a diagnostic test and/or conclusions drawn from and/or treatment recommendations based on the test, may be generated and delivered automatically to the subject using a combination of computer hardware and software which will be familiar to artisans skilled in telecommunications. One example of a healthcare-oriented communications system is described in U.S. Pat. No. 6,283,761; however, the present disclosure is not limited to methods which utilize this particular communications system. In certain embodiments of the methods of the disclosure, all or some of the method steps, including the assaying of samples, diagnosing of diseases, and communicating of assay results or diagnoses, may be carried out in diverse (e.g., foreign) jurisdictions.

In several embodiments, identification of a subject as having a neurodegenerative disease, such as AD or PD, results in the physician treating the subject, such as prescribing one or more therapeutic agents for inhibiting or delaying one or more signs and symptoms associated with said disease. In additional embodiments, the dose or dosing regimen is modified based on the information obtained using the methods disclosed herein. The subject can be monitored while undergoing treatment using the methods described herein in order to assess the efficacy of the treatment protocol. In this manner, the length of time or the amount of therapeutic given to the subject can be modified based on the results obtained using the methods disclosed herein.

An advantage with the disclosed invention is that the AD DARPins were selective for AD cases and the PD DARPins were selective for PD cases using both human brain tissue and sera samples. Such distinction, especially using sera, provides a less invasive and more disease specific diagnostic test than currently available. Moreover, the disclosed invention revealed distinct variants of beta-amyloid, alpha-synuclein, TAR-DNA binding protein 43 and tau that were specific to AD compared to PD and vice versa. This discovery allows for more disease specific diagnostic tests to be developed.

B. Assays for Diagnosing and Monitoring Neurodegenerative-Associated Conditions

The methods disclosed herein can be performed in the form of various assays, including immunoassay formats, which are well known in the art. There are two main types of immunoassays, homogeneous and heterogeneous. In homogeneous immunoassays, both the immunological reaction between an antigen and an antibody and the detection are carried out in a homogeneous reaction. Heterogeneous immunoassays include at least one separation step, which allows the differentiation of reaction products from unreacted reagents. A variety of immunoassays can be used to detect one or more of the molecules capable of detecting a neurodegenerative disease, such as AD, PD and/or ALS. In one example, one or more antigens associated with AD are measured to diagnose an AD-associated disorder. For example, one or more AD protein antigens are detected with a disclosed immunoassay. In one example, at least one or more of the following antigens are detected: ADC1, ADC3, ADC6, or ADC7. In one example, one or more antigens associated with PD are measured to diagnose a PD-associated disorder. For example, one or more PD protein antigens are detected with a disclosed immunoassay. In one example, at least one or more of the following antigens are detected: PDA6, PDA8, PDA9, or PDC1. In some examples, the disclosed immunoassay includes at least one, such as two, three, four, or more molecules associated with AD and/or at least one, such as two, three, four, or more molecules associated with PD. In one example, the assay includes at least ADC1, ADC3, ADC6, and ADC7. In one example, the assay includes at least PDA6, PDA8, PDA9, and PDC1. In one example, the assay includes at least PDA6, PDA8, PDA9, PDC1, ADC1, ADC3, ADC6, or ADC7.

ELISA is a heterogeneous immunoassay, which has been widely used in laboratory practice since the early 1970s, and can be used in the methods disclosed herein. The assay can be used to detect protein antigens in various formats. In the "sandwich" format the antigen being assayed is held between two different antibodies. In this method, a solid surface is first coated with a solid phase antibody. The test sample, containing the antigen (e.g., a diagnostic protein), or a composition containing the antigen, such as a urine sample from a subject of interest, is then added and the antigen is allowed to react with the bound antibody. Any unbound antigen is washed away. A known amount of enzyme-labeled antibody is then allowed to react with the bound antigen. Any excess unbound enzyme-linked antibody is washed away after the reaction. The substrate for the enzyme used in the assay is then added and the reaction between the substrate and the enzyme produces a color change. The amount of visual color change is a direct measurement of specific enzyme-conjugated bound antibody, and consequently the antigen present in the sample tested.

ELISA can also be used as a competitive assay. In the competitive assay format, the test specimen containing the antigen to be determined is mixed with a precise amount of enzyme-labeled antigen and both compete for binding to an anti-antigen antibody attached to a solid surface. Excess free enzyme-labeled antigen is washed off before the substrate for the enzyme is added. The amount of color intensity resulting from the enzyme-substrate interaction is a measure of the amount of antigen in the sample tested. A heterogeneous immunoassay, such as an ELISA, can be used to detect any molecules associated with a neurodegenerative disease such as AD, PD or ALS. In some examples, commercially available antibodies against TDP-43, Tau, Beta-amyloid and alpha synuclein are used for detecting neurodegenerative-associated antigens.

In another example, immuno-PCR can be used to detect any of the molecules associated with a neurodegenerative disease, such as AD, PD and/or ALS. Immuno-PCR is a modification of the conventional ELISA format in which the detecting antibody is labeled with a DNA label, and is applicable to the analysis of biological samples (see, e.g., U.S. Pat. No. 5,665,539 and U.S. Patent Application Publication No. 2005/0239108; all herein incorporated by reference). The amplification ability of PCR provides large amounts of the DNA label which can be detected by various methods, typically gel electrophoresis with conventional staining (e.g., Sano et al., Science, 258:120-122, 1992). This method can also include the direct conjugation of the DNA label to the antibody and replacement of gel electrophoresis by using labeled primers to generate a PCR product that can be assayed by ELISA or using real time quantitative PCR. In an example of the real-time PCR method, PCR is used to amplify DNA in a sample in the presence of a nonextendable dual labeled fluorogenic hybridization probe. One fluorescent dye serves as a reporter and its emission spectra is quenched by the second fluorescent dye. The method uses the 5' nuclease activity of Taq polymerase to cleave a hybridization probe during the extension phase of PCR. The nuclease degradation of the hybridization probe releases the quenching of the reporter dye resulting in an increase in peak emission from the reporter. The reactions are monitored in real time.

Homogeneous immunoassays include, for example, the Enzyme Multiplied Immunoassay Technique (EMIT), which typically includes a biological sample comprising the biomarkers to be measured, enzyme-labeled molecules of the biomarkers to be measured, specific antibody or antibodies binding the biomarkers to be measured, and a specific enzyme chromogenic substrate. In a typical EMIT, excess of specific antibodies is added to a biological sample. If the biological sample contains the molecules to be detected, such molecules bind to the antibodies. A measured amount of the corresponding enzyme-labeled molecules is then added to the mixture. Antibody binding sites not occupied by molecules of the protein in the sample are occupied with molecules of the added enzyme-labeled protein. As a result, enzyme activity is reduced because only free enzyme-labeled protein can act on the substrate. The amount of substrate converted from a colorless to a colored form determines the amount of free enzyme left in the mixture. A high concentration of the protein to be detected in the sample causes higher absorbance readings. Less protein in the sample results in less enzyme activity and consequently lower absorbance readings. Inactivation of the enzyme label when the antigen-enzyme complex is antibody-bound makes the EMIT a useful system, enabling the test to be performed without a separation of bound from unbound compounds as is necessary with other immunoassay methods. A homogenous immunoassay, such as an EMIT, can be used to detect any of the molecules associated with neurodegenerative disease, such as AD, PD, or ALS, including, but not limited to those disclosed herein, such as PDA6, PDA8, PDA9, PDC1, ADC1, ADC3, ADC6, and/or ADC7.

Immunoassay kits are also disclosed herein. These kits include, in separate containers (a) monoclonal antibodies having binding specificity for the DARPins used in the diagnosis of AD or PD; and (b) and anti-antibody immunoglobulins. This immunoassay kit may be utilized for the practice of the various methods provided herein. The monoclonal antibodies and the anti-antibody immunoglobulins can be provided in an amount of about 0.001 mg to 100 grams, and more preferably about 0.01 mg to 1 gram. The anti-antibody immunoglobulin may also be a polyclonal immunoglobulin, protein A or protein G or functional fragments thereof, which may be labeled prior to use by methods known in the art. In several embodiments, the immunoassay kit includes one, two, three or four or more antibodies that specifically bind to molecules associated with AD or PD. The immunoassay kit can also include one or more antibodies that specifically bind to one or more of these molecules. Thus, the kits can be used to detect one or more different molecules (DARPins) associated a neurodegenerative disease/condition, including AD, PD and/or ALS.

Immunoassays for polysaccharides and proteins differ in that a single antibody is used for both the capture and indicator roles for polysaccharides due to the presence of repeating epitopes. In contrast, two antibodies specific for distinct epitopes are required for immunoassay of proteins. Exemplary samples include biological samples obtained from subjects including, but not limited to, serum, blood and urine samples. In some examples, an exemplary sample includes bronchoalveolar lavage fluid.

In one particular example, a quantitative ELISA is constructed for detection of at least one of the AD or PD DARPins disclosed herein. These immunoassays utilize antibodies, such as mAbs commercially available. Since a polysaccharide is a polyvalent repeating structure, a single mAb may be used for both the capture and indicator phases of an immunoassay. The only requirement is that the mAb have a sufficient affinity. A mAb with an affinity of about 0.5 µM has sufficient affinity.

C. Capture Device Methods

The disclosed methods can be carried out using a sample capture device, such as a lateral flow device (for example a lateral flow test strip) that allows detection of one or more molecules, such as those described herein. Point-of-use analytical tests have been developed for the routine identification or monitoring of health-related conditions (such as pregnancy, cancer, endocrine disorders, infectious diseases or drug abuse) using a variety of biological samples (such as urine, serum, plasma, blood, saliva). Some of the point-of-use assays are based on highly specific interactions between specific binding pairs, such as antigen/antibody, hapten/antibody, lectin/carbohydrate, apoprotein/cofactor and biotin/(strept)avidin. The assays are often performed with test strips in which a specific binding pair member is attached to a mobilizable material (such as a metal sol or beads made of latex or glass) or an immobile substrate (such as glass fibers, cellulose strips or nitrocellulose membranes). Particular examples of some of these assays are shown in U.S. Pat. Nos. 4,703,017; 4,743,560; and U.S. Pat. No. 5,073,484 (incorporated herein by reference). The test strips include a flow path from an upstream sample application area to a test site. For example, the flow path can be from a sample application area through a mobilization zone to a capture zone. The mobilization zone may contain a mobilizable marker that interacts with an analyte or analyte analog, and the capture zone contains a reagent that binds the analyte or analyte analog to detect the presence of an analyte in the sample.

Examples of migration assay devices, which usually incorporate within them reagents that have been attached to colored labels, thereby permitting visible detection of the assay results without addition of further substances are found, for example, in U.S. Pat. No. 4,770,853; WO 88/08534; and EP-A 0 299 428 (incorporated herein by reference). There are a number of commercially available lateral-flow type tests and patents disclosing methods for the detection of large analytes (MW greater than 1,000 Daltons) as the analyte flows through multiple zones on a test strip. Examples are found in U.S. Pat. No. 5,229,073 (measuring plasma lipoprotein levels), and U.S. Pat. Nos. 5,591,645;

4,168,146; 4,366,241; 4,855,240; 4,861,711; 5,120,643; European Patent No. 0296724; WO 97/06439; WO 98/36278; and WO 08/030546 (each of which are herein incorporated by reference). Multiple zone lateral flow test strips are disclosed in U.S. Pat. Nos. 5,451,504, 5,451,507, and U.S. Pat. No. 5,798,273 (incorporated by reference herein). U.S. Pat. No. 6,656,744 (incorporated by reference) discloses a lateral flow test strip in which a label binds to an antibody through a streptavidin-biotin interaction.

In particular examples, the methods disclosed herein include application of a biological sample (such as serum, whole blood or urine) from a test subject to a lateral flow test device for the detection of one or more molecules (such as one or more molecules associated with a neurodegenerative disease, such as combinations of molecules as described above) in the sample. The lateral flow test device includes one or more antibodies (such as antibodies that bind one or more of the molecules associated with AD or PD) at an addressable location. In a particular example, the lateral flow test device includes antibodies that bind at least one AD-associated molecule or PD-associated molecule disclosed herein. The addressable locations can be, for example, a linear array or other geometric pattern that provides diagnostic information to the user. The binding of one or more molecules in the sample to the antibodies present in the test device is detected and the presence or amount of one or more molecules in the sample of the test subject is compared to a control, wherein a change in the presence or amount of one or more molecules in the sample from the test subject as compared to the control indicates that the subject has an AD or PD.

Devices described herein generally include a strip of absorbent material (such as a microporous membrane), which, in some instances, can be made of different substances each joined to the other in zones, which may be abutted and/or overlapped. In some examples, the absorbent strip can be fixed on a supporting non-interactive material (such as nonwoven polyester), for example, to provide increased rigidity to the strip. Zones within each strip may differentially contain the specific binding partner(s) and/or other reagents required for the detection and/or quantification of the particular analyte being tested for, for example, one or more molecules disclosed herein. Thus these zones can be viewed as functional sectors or functional regions within the test device.

In general, a fluid sample is introduced to the strip at the proximal end of the strip, for instance by dipping or spotting. A sample is collected or obtained using methods well known to those skilled in the art. The sample containing the particular molecules to be detected may be obtained from any biological source. Examples of biological sources include blood serum, blood plasma, urine, BALF, spinal fluid, saliva, fermentation fluid, lymph fluid, tissue culture fluid and ascites fluid of a human or animal. In a particular example, the biological source is saliva. In one particular example, the biological source is whole blood, such as a sample obtained from a finger prick. The sample may be diluted, purified, concentrated, filtered, dissolved, suspended or otherwise manipulated prior to assay to optimize the immunoassay results. The fluid migrates distally through all the functional regions of the strip. The final distribution of the fluid in the individual functional regions depends on the adsorptive capacity and the dimensions of the materials used.

Another common feature to be considered in the use of assay devices is a means to detect the formation of a complex between an analyte (such as one or more molecules described herein) and a capture reagent (such as one or more antibodies). A detector (also referred to as detector reagent) serves this purpose. A detector may be integrated into an assay device (for example included in a conjugate pad, as described below), or may be applied to the device from an external source.

A detector may be a single reagent or a series of reagents that collectively serve the detection purpose. In some instances, a detector reagent is a labeled binding partner specific for the analyte (such as a gold-conjugated antibody for a particular protein of interest, for example those described herein).

In other instances, a detector reagent collectively includes an unlabeled first binding partner specific for the analyte and a labeled second binding partner specific for the first binding partner and so forth. Thus, the detector can be a labeled antibody specific for a protein described herein. The detector can also be an unlabeled first antibody specific for the protein of interest and a labeled second antibody that specifically binds the unlabeled first antibody. In each instance, a detector reagent specifically detects bound analyte of an analyte-capture reagent complex and, therefore, a detector reagent preferably does not substantially bind to or react with the capture reagent or other components localized in the analyte capture area. Such non-specific binding or reaction of a detector may provide a false positive result. Optionally, a detector reagent can specifically recognize a positive control molecule (such as a non specific human IgG for a labeled Protein A detector, or a labeled Protein G detector, or a labeled anti human Ab(Fc)) that is present in a secondary capture area.

Flow-Through Device Construction and Design

Representative flow-through assay devices are described in U.S. Pat. Nos. 4,246,339; 4,277,560; 4,632,901; 4,812,293; 4,920,046; and 5,279,935; U.S. Patent Application Publication Nos. 20030049857 and 20040241876; and WO 08/030546. A flow-through device involves a capture reagent (such as one or more antibodies) immobilized on a solid support, typically, a membrane (such as, nitrocellulose, nylon, or PVDF). Characteristics of useful membranes have been previously described; however, it is useful to note that in a flow-through assay capillary rise is not a particularly important feature of a membrane as the sample moves vertically through the membrane rather than across it as in a lateral flow assay. In a simple representative format, the membrane of a flow-through device is placed in functional or physical contact with an absorbent layer (see, e.g., description of "absorbent pad" below), which acts as a reservoir to draw a fluid sample through the membrane. Optionally, following immobilization of a capture reagent, any remaining protein-binding sites on the membrane can be blocked (either before or concurrent with sample administration) to minimize nonspecific interactions.

In operation of a flow-through device, a fluid sample (such as a bodily fluid sample) is placed in contact with the membrane. Typically, a flow-through device also includes a sample application area (or reservoir) to receive and temporarily retain a fluid sample of a desired volume. The sample passes through the membrane matrix. In this process, an analyte in the sample (such as one or more protein, for example, one or more molecules described herein) can specifically bind to the immobilized capture reagent (such as one or more antibodies). Where detection of an analyte-capture reagent complex is desired, a detector reagent (such as labeled antibodies that specifically bind one or more molecules) can be added with the sample or a solution containing a detector reagent can be added subsequent to application of the sample. If an analyte is specifically bound by capture reagent, a visual representative attributable to the particular detector reagent can be observed on the surface of the membrane. Optional wash steps can be added at any time in the process, for instance, following application of the sample, and/or following application of a detector reagent.

Lateral Flow Device Construction and Design

Lateral flow devices are commonly known in the art. Briefly, a lateral flow device is an analytical device having as its essence a test strip, through which flows a test sample fluid that is suspected of containing an analyte of interest. The test fluid and any suspended analyte can flow along the strip to a detection zone in which the analyte (if present) interacts with a capture agent and a detection agent to indicate a presence, absence and/or quantity of the analyte.

Numerous lateral flow analytical devices have been disclosed, and include those shown in U.S. Pat. Nos. 4,168,146; 4,313,734; 4,366,241; 4,435,504; 4,775,636; 4,703,017; 4,740,468; 4,806,311; 4,806,312; 4,861,711; 4,855,240; 4,857,453; 4,861,711; 4,943,522; 4,945,042; 4,496,654; 5,001,049; 5,075,078; 5,126,241; 5,120,643; 5,451,504; 5,424,193; 5,712,172; 6,555,390; 6,258,548; 6,699,722; 6,368,876 and 7,517,699; EP 0810436; EP 0296724; WO 92/12428; WO 94/01775; WO 95/16207; WO 97/06439; WO 98/36278; and WO 08/030546, each of which is incorporated by reference. Further, there are a number of commercially available lateral flow type tests and patents disclosing methods for the detection of large analytes (MW greater than 1,000 Daltons). U.S. Pat. No. 5,229,073 describes a semiquantitative competitive immunoassay lateral flow method for measuring plasma lipoprotein levels. This method utilizes a plurality of capture zones or lines containing immobilized antibodies to bind both the labeled and free lipoprotein to give a semi-quantitative result. In addition, U.S. Pat. No. 5,591,645 provides a chromatographic test strip with at least two portions. The first portion includes a movable tracer and the second portion includes an immobilized binder capable of binding to the analyte.

Many lateral flow devices are one-step lateral flow assays in which a biological fluid is placed in a sample area on a bibulous strip (though non-bibulous materials can be used, and rendered bibulous, e.g., by applying a surfactant to the material), and allowed to migrate along the strip until the liquid comes into contact with a specific binding partner (such as an antibody) that interacts with an analyte (such as one or more molecules) in the liquid. Once the analyte interacts with the binding partner, a signal (such as a fluorescent or otherwise visible dye) indicates that the interaction has occurred. Multiple discrete binding partners (such as antibodies) can be placed on the strip (for example in parallel lines) to detect multiple analytes (such as two or more molecules) in the liquid. The test strips can also incorporate control indicators, which provide a signal that the test has adequately been performed, even if a positive signal indicating the presence (or absence) of an analyte is not seen on the strip.

The construction and design of lateral flow devices is known in the art, as described, for example, in Millipore Corporation, A Short Guide Developing Immunochromatographic Test Strips, 2nd Edition, pp. 1-40, 1999, available by request at (800) 645 5476; and Schleicher & Schuell, Easy to Work with BioScience, Products and Protocols 2003, pp. 73-98, 2003, available by request at Schleicher & Schuell BioScience, Inc., 10 Optical Avenue, Keene, N.H. 03431, (603) 352 3810; both of which are incorporated herein by reference.

Lateral flow devices have a wide variety of physical formats that are known in the art. Any physical format that supports and/or houses the basic components of a lateral flow device in the proper function relationship is contemplated by this disclosure.

In some embodiments, the lateral flow strip is divided into a proximal sample application pad, an intermediate test result zone, and a distal absorbent pad. The flow strip is interrupted by a conjugate pad that contains labeled conjugate (such as gold- or latex-conjugated antibody specific for the target analyte or an analyte analog). A flow path along strip passes from proximal pad, through conjugate pad, into test result zone, for eventual collection in absorbent pad. Selective binding agents are positioned on a proximal test line in the test result membrane. A control line is provided in test result zone, slightly distal to the test line. For example, in a competitive assay, the binding agent in the test line specifically binds the target analyte, while the control line less specifically binds the target analyte.

In operation of the particular embodiment of a lateral flow device, a fluid sample containing an analyte of interest, such as one or more molecules described herein (for example, AD or PD-associated molecules, as discussed above), is applied to the sample pad. In some examples, the sample may be applied to the sample pad by dipping the end of the device containing the sample pad into the sample (such as serum or urine) or by applying the sample directly onto the sample pad (for example by placing the sample pad in the mouth of the subject). In other examples where a sample is whole blood, an optional developer fluid is added to the blood sample to cause hemolysis of the red blood cells and, in some cases, to make an appropriate dilution of the whole blood sample.

From the sample pad, the sample passes, for instance by capillary action, to the conjugate pad. In the conjugate pad, the analyte of interest, such as a protein of interest, may bind (or be bound by) a mobilized or mobilizable detector reagent, such as an antibody (such as antibody that recognizes one or more of the molecules described herein). For example, a protein analyte may bind to a labeled (e.g., gold-conjugated or colored latex particle-conjugated) antibody contained in the conjugate pad. The analyte complexed with the detector reagent may subsequently flow to the test result zone where the complex may further interact with an analyte-specific binding partner (such as an antibody that binds a particular protein, an anti-hapten antibody, or streptavidin), which is immobilized at the proximal test line. In some examples, a protein complexed with a detector reagent (such as gold-conjugated antibody) may further bind to unlabeled, oxidized antibodies immobilized at the proximal test line. The formation of a complex, which results from the accumulation of the label (e.g., gold or colored latex) in the localized region of the proximal test line is detected. The control line may contain an immobilized, detector-reagent-specific binding partner, which can bind the detector reagent in the presence or absence of the analyte. Such binding at the control line indicates proper performance of the test, even in the absence of the analyte of interest. The test results may be visualized directly, or may be measured using a reader (such as a scanner). The reader device may detect color or fluorescence from the readout area (for example, the test line and/or control line).

In another embodiment of a lateral flow device, there may be a second (or third, fourth, or more) test line located parallel or perpendicular (or in any other spatial relationship) to test line in test result zone. The operation of this particular embodiment is similar to that described in the immediately preceding paragraph with the additional considerations that (i) a second detector reagent specific for a second analyte, such as another antibody, may also be contained in the conjugate pad, and (ii) the second test line will contain a second specific binding partner having affinity for a second analyte, such as a second protein in the sample. Similarly, if a third (or more) test line is included, the test line will contain a third (or more) specific binding partner having affinity for a third (or more) analyte.

1. Sample Pad

The sample pad is a component of a lateral flow device that initially receives the sample, and may serve to remove particulates from the sample. Among the various materials that may be used to construct a sample pad (such as glass fiber, woven fibers, screen, non-woven fibers, cellosic fibers or paper), a cellulose sample pad may be beneficial if a large bed volume (e.g., 250 µl/cm2) is a factor in a particular application. Sample pads may be treated with one or more release agents, such as buffers, salts, proteins, detergents, and surfactants. Such release agents may be useful, for example, to promote resolubilization of conjugate-pad constituents, and to block non specific binding sites in other components of a lateral flow device, such as a nitrocellulose membrane. Representative release agents include, for example, trehalose or glucose, PVP or PVA, Tween 20 or Triton X 100, casein, SDS, and PEG.

2. Membrane and Application Solution:

The types of membranes useful in a lateral flow device (such as nitrocellulose (including pure nitrocellulose and modified nitrocellulose), nitrocellulose direct cast on polyester support, polyvinylidene fluoride, or nylon), and considerations for applying a capture reagent to such membranes have been discussed previously.

In some embodiments, membranes comprising nitrocellulose are preferably in the form of sheets or strips. The thickness of such sheets or strips may vary within wide limits, for example, from about 0.01 to 0.5 mm, from about 0.02 to 0.45 mm, from about 0.05 to 0.3 mm, from about 0.075 to 0.25 mm, from about 0.1 to 0.2 mm, or from about 0.11 to 0.15 mm. The pore size of such sheets or strips may similarly vary within wide limits, for example from about 0.025 to 15 microns, or more specifically from about 0.1 to 3 microns; however, pore size is not intended to be a limiting factor in selection of the solid support. The flow rate of a solid support, where applicable, can also vary within wide limits, for example from about 12.5 to 90 sec/cm (i.e., 50 to 300 sec/4 cm), about 22.5 to 62.5 sec/cm (i.e., 90 to 250 sec/4 cm), about 25 to 62.5 sec/cm (i.e., 100 to 250 sec/4 cm), about 37.5 to 62.5 sec/cm (i.e., 150 to 250 sec/4 cm), or about 50 to 62.5 sec/cm (i.e., 200 to 250 sec/4 cm). In specific embodiments of devices described herein, the flow rate is about 62.5 sec/cm (i.e., 250 sec/4 cm). In other specific embodiments of devices described herein, the flow rate is about 37.5 sec/cm (i.e., 150 sec/4 cm).

3. Conjugate Pad

The conjugate pad serves to, among other things, hold a detector reagent. Suitable materials for the conjugate pad include glass fiber, polyester, paper, or surface modified polypropylene. In some embodiments, a detector reagent may be applied externally, for example, from a developer bottle, in which case a lateral flow device need not contain a conjugate pad (see, for example, U.S. Pat. No. 4,740,468).

Detector reagent(s) contained in a conjugate pad is typically released into solution upon application of the test sample. A conjugate pad may be treated with various substances to influence release of the detector reagent into solution. For example, the conjugate pad may be treated with PVA or PVP (0.5% to 2%) and/or Triton X 100 (0.5%). Other release agents include, without limitation, hydroxypropylmethyl cellulose, SDS, Brij and (3-lactose. A mixture of two or more release agents may be used in any given application. In a particular disclosed embodiment, the detector reagent in conjugate pad is a gold-conjugated antibody.

4. Absorbent Pad

The use of an absorbent pad in a lateral flow device is optional. The absorbent pad acts to increase the total volume of sample that enters the device. This increased volume can be useful, for example, to wash away unbound analyte from the membrane. Any of a variety of materials is useful to prepare an absorbent pad, for example, cellulosic filters or paper. In some device embodiments, an absorbent pad can be paper (i.e., cellulosic fibers). One of skill in the art may select a paper absorbent pad on the basis of, for example, its thickness, compressibility, manufacturability, and uniformity of bed volume. The volume uptake of an absorbent made may be adjusted by changing the dimensions (usually the length) of an absorbent pad.

The disclosure is illustrated by the following non-limiting Example.

Example

Generation of DARPins Library and Completion of Disease Selective Biopanning Process Design ankyrin repeat proteins (DARPins) are important stable structures for protein-protein interactions. Their stability is maintained even following connection of multiple repeats making them an attractive replacement for antibodies and single-chain variable fragments (scFvs). The inventors isolated DARPins reactive with biomarkers of Alzheimer's disease (AD), Parkinson's disease (PD) and amyotrophic lateral sclerosis (ALS). To begin, a DARPins library was created. This was created by joining the N-Cap, C-Cap and ankyrin repeat module (AR) module fragments to create a one-repeat DARPin library of $7.2 \times 10^7$ diversity (Binz et al., 2003). The generic protein sequences and other details of the DARPins library are listed in FIG. 1 (Protein Template:

```
                                    (SEQ ID NO: 1)
5'MKKIWLALAGLVLAFSASADYKEAQPAMDLGKKLLEAARAGQDDEVRI
LMANGADVNAXDXXGXTPLHLAAXXGHLEIVEVLLKXGADVNAQDKFGKT
AFDISIDNGNEDLAEILQAAAHHHHHHGAAEQKLISEEDLNGAA-3';

N-Cap:
                                    (SEQ ID NO: 2)
5'-DLGKKLLEAARAGQDDEVRILMANGADV-3';

C-Cap:
                                    (SEQ ID NO: 3)
5'-VNAQDKFGKTAFDISIDNGNEDLAEILQ-3'. Titration of
```
the library indicated that there was $10^{10}$ cells/ml.

Figure 3:
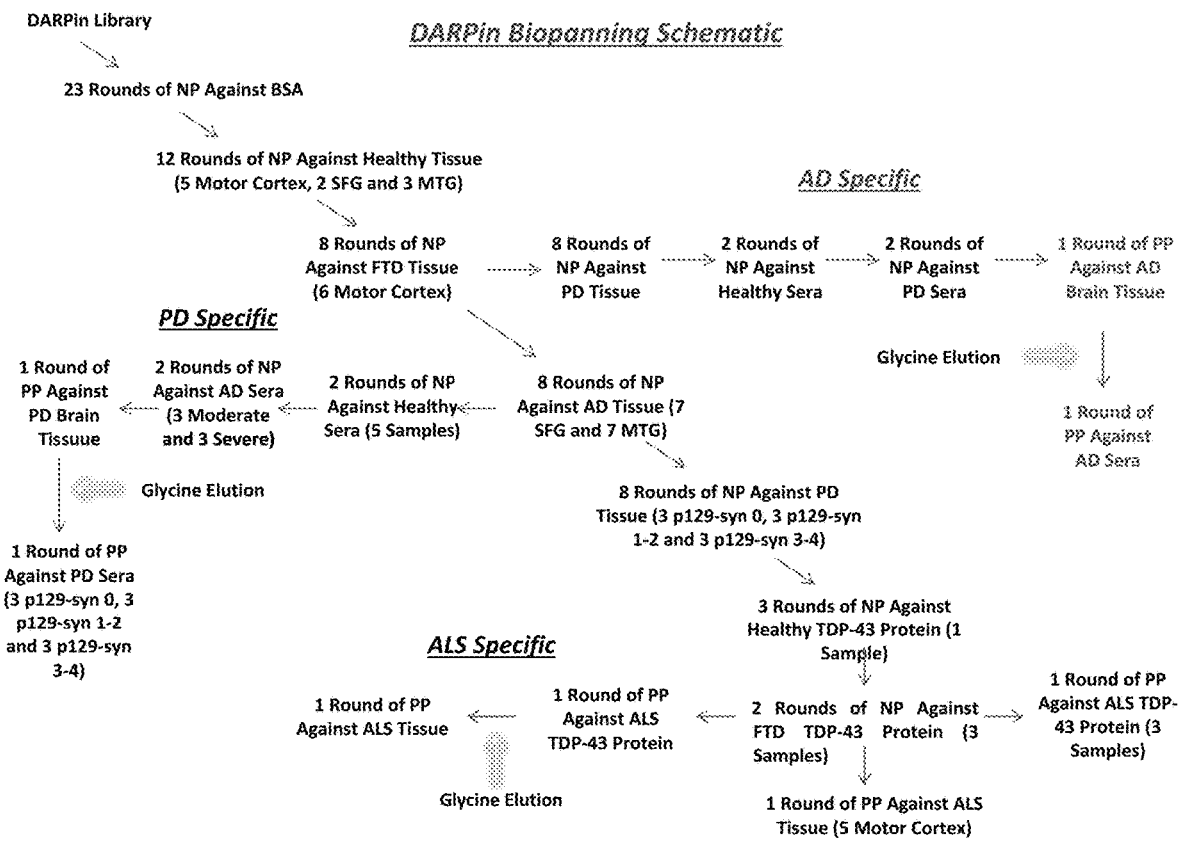

Phage particles were then generated from the DARPins library using phage-display technology and negative and positive atomic forced microscopy (AFM) based biopanning procedures. In AFM-based biopanning technology undesired targets were first removed through multiple rounds of negative panning and complete removal monitored using AFM technology. In the positive biopanning phase, mica containing the targets of interest were then incubated with the remaining phage particles to isolate reagents with selective recognition of those targets. The biopanning process utilized to isolate DARPins that are more selective for PD biomarkers compared to AD biomarkers and vice versa was more complicated. To isolate PD specific biomarkers, DARPins reactive with bovine serum album (BSA), healthy human brain tissue, brain tissue from human frontotemporal dementia (FTD) cases, brain tissue from AD cases, sera samples from healthy human cases and sera samples from AD cases were removed using multiple rounds of negative panning steps with each of the undesired target. An aliquot of the remaining phage particles was then added to mica containing brain tissue from PD cases, the bound phage particles eluted and then re-incubated with mica containing sera samples from PD cases. The DARPins isolated after this second set of positive biopanning procedures recognized biomarkers present in both brain tissue and sera samples from PD cases (FIG. 2). To isolate AD specific biomarkers, DARPins reactive with bovine serum album (BSA), healthy human brain tissue, brain tissue from human frontotemporal dementia (FTD) cases, brain tissue from PD cases, sera samples from healthy human cases and sera samples from PD cases were removed using multiple rounds of negative panning steps with each of the undesired target. An aliquot of the remaining phage particles was then added to mica containing brain tissue from human AD cases, the bound phage particles eluted and then added to mica containing sera samples from human AD cases. The DARPins isolated after this second set of positive biopanning procedures should recognize biomarkers present in both brain tissue and sera samples from AD cases (FIG. 3). The importance of the DARPins recognizing their targets in sera is to ensure an easier diagnostic process for potentially affected individuals. It should be mentioned that the AD and PD brain tissue and sera samples utilized here were from post-mortem pathologically confirmed cases. Following DNA analysis, 4 DARPins reactive with AD (ADC1, ADC3, ADC6, and ADC7) and 4 DARPins reactive with PD (PDA6, PDA8, PDA9, and PDC1) were revealed with the following sequences:

ADC1 (Reactive with Beta-Amyloid) DNA Sequence:
(SEQ ID NO: 4)
5'-aagatttggctggcgctggctggnttagttttagcgtttagcgcatc ggcggactacaaagaggcccagccggccatggacctgggtaagaaactgc tggaagctgctcgtgctggtcaggacgacgaagttcgtatcctgatggct aacggtgctgacgttaacgctgacgaccgtaacggtatgactccgctgca cctggctgctcatcagggtcacctggaaatcgttgaagttctgctgaagt acggtgctgacgttaacgctcaggacaaattcggtaagaccgattcgaca tctccatcgacaacggtaacgaggacctggctgaaatcctgcaagcggcc gcacatcatcatcaccatcacggggccgcagaacaaaaactcatctcaga agaggatctgaatggggccgcatagactgttgaaagttgtttagcaaaac ctcatacagaaaattcatttactaacgtctggaaagacgacaaaactta gatcgttacgctaactatgagggctgtctgtggaatgctacaggcgttgt ggtttgtactggtgacgaaactcagtgttacggtacatgggttcctattg ggcttgctatccctgaaaatgagggtggtggctctgagggtggcggttct gagggtggcggttctg-3';

Protein Sequence:
(SEQ ID NO: 5)
5'-KIWLALAXLVLAFSASADYKEAQPAMDLGKKLLEAARAGQDDEVRIL

MANGADVNADDRNGMTPLHLAAHQGHLEIVEVLLKYGADVNAQDKFGKTA

FDISIDNGNEDLAEILQAAAHHHHHHGAAEQKLISEEDLNGAA-3'.

ADC3 (Reactive with TDP-43), DNA Sequence:
(SEQ ID NO: 6)
5'-tggnttagttttagcgtttagcgcatcggcggactacaaagaggccc agccggccatggacctgggtaagaaactgctggaagctgctcgtgctggt ctggacgacgaagttcgtatcctgatggctaacggtgctgacgttaacgc tactgacactgacggttctagtccgctgcacctggctgctcaggaaggtc acctggaaatcgttgaagttctgctgaagtacggtgctgacgttaacgct caggacaaattcggtaagaccgattcgacatctccatcgacaacggtaac gaggacctggctgaaatcctgcaagcggccgcacatcatcatcaccatca cggggccgcagaacaaaaactcatctcagaagaggatctgaatggggccg catagactgttgaaagttgtttagcaaaacctcatacagaaaattcantn nctaacgtctggaaagacgacaaaactttagatcgttacgctaactatga gggctgtctgtggaatgctacaggcgttgtggtttgtactggtgacgaaa ctcagtgttacggtacatgggttcctattgggcttgctatccctgaaaat gagggtggtggctctganggtggcggttctgagggtggcggt-3';

Protein Sequence:
(SEQ ID NO: 7)
5'-GAGXLVLAFSASADYKEAQPAMDLGKKLLEAARAGLDDEVRILMANG

ADVNATDTDGSSPLHLAAQEGHLEIVEVLLKYGADVNAQDKFGKTAFDIS

IDNGNEDLAEILQAAAHHHHHHGAAEQKLISEEDLNGAA-3'.

ADC6 (Reactive with Alpha-Synuclein), DNA Sequence:
(SEQ ID NO: 8)
5'-ctggcgctggctggtttagttttagcgtttagcgcatcggcggacta caaagaggcccagccggccatggacctgggtaagaaactgctggaagctg ctcgtgctggtcaggacgacgaagttcgtatcctgatggctaacggtgct gacgttaacgctgctgacttcaacggtcaaactccgctgcacctggctgc tgtttggggtcacctggaaatcgttgaagttctgctgaagaacggtgctg acgttaacgctcaggacaaattcggtaagaccgattcgacatctccatcg acaacggtaacgaggacctggctgaaatcctgcaagcggccgcacatcat catcaccatcacggggccgcagaacaaaaactcatctcagaagaggatct gaatggggccgcatagactgttgaaagttgtttagcaaaacctcatacag aaaattcnnnnactaacgtctggaaagacgacaaaactttagatcgttac gctaactatgagggctgtctgtggaatgctacaggcgttgtggtttgtac tggtgacgaaactcagtgttacggtacatgggttcctattgggcttgcta tccctgaaaatgagggtggtggctctganggtggcggttctgagggtggc ggttctgagggt-3';

Protein Sequence:
(SEQ ID NO: 9)
5'-LALAGLVLAFSASADYKEAQPAMDLGKKLLEAARAGQDDEVRILMAN

GADVNAADFNGQTPLHLAAVWGHLEIVEVLLKNGADVNAQDKFGKTAFDI

SIDNGNEDLAEILQAAAHHHHHHGAAEQKLISEEDLNGAA-3'.

ADC7 (Reactive with Tau), DNA Sequence:
(SEQ ID NO: 10)
5'-tttagttttagcgtttagcgcatcggcggactacaaagaggcccagc
cggccatggacctgggtaagaaactgctggaagctgctcgtgctggtcag
gacgacgaagttcgtatcctgatggctaacggtgctgacgttaacgctcg
tgacgtttctggtgctactccactgcacctggctgctacttggggtcacc
tggaaatcgttgaagttctgctgaagtacggtgctgacgttaacgctcag
gacaaattcggtaagaccgctttcgacatctccatcgacaacggtaacga
ggacctggctgaaatcctgcaagcggccgcacatcatcatcaccatcacg
gggccgcagaacaaaaactcatctcagaagaggatctgaatggggccgca
tagactgttgaaagttgtttagcaaaacctcatacagaaaattnannnac
taacgtctggaaagacgacaaaaactttagatcgttacgctaactatgagg
gctgtctgtggaatgctacaggcgttgtggtttgtactggtgacgaaact
cagtgttacggtacatgggttcctattgggcttgctatccctgaaaatga
ggg-3';

Protein Sequence:
(SEQ ID NO: 11)
5'-WLALXXLVLAFSASADYKEAQPAMDLGKKLLEAARAGQDDEVRILMA
NGADVNARDVSGATPLHLAATWGHLEIVEVLLKYGADVNAQDKFGKTAFD
ISIDNGNEDLAEILQAAAHHHHHHGAAEQKLISEEDLNGAA-3'

PDA6 (Reactive with Beta-Amyloid), DNA Sequence:
(SEQ ID NO: 12)
5'-nnnnnnnnnnntgnnnttctanttcnggaganagtcatagctagcat
gaaaagatttgnctggcgctggctggtttagttttagcgtttagcgcat
cggcggactacaaagaggcccagccggccatggacctgggtaagaaactg
ctggaagctgctcgtgctggtcaggacgacgaagttcgtatcctgatggc
taacggtgctgacgttaacgctcaggacactaaaggttacactccgctgc
acctggctgctaactctggtcacctggaaatcgttgaagttctgctgaag
aacggtgctgacgttaacgctcaggacaaattcggtaagaccgctttcga
catctccatcgacaacggtaacgaggacctggctgaaatcctgcaagcgg
ccgcacatcatcatcaccatcacggggccgcagaacaaaaactcatctca
gaagaggatctgaatggggccgcatagactgttgaaagttgtttagcaaa
acctcatacagaaaattcatttactaacgtctggaaagacgacaaaactt
tagatcgttacgctaactatgagggctgtctgtggaatgctacaggcgtt
gtggtttgtactggtgacgaaactcagtgttacggtacatgggttcctat
tgggcttgctatccctgaaaatgagggtggtggctctgagggtggcggtt
ctgagggtggcggttctgagggt-3';

Protein Sequence:
(SEQ ID NO: 13)
5'-VIASMKKIXLALAGLVLAFSASADYKEAQPAMDLGKKLLEAARAGQD
DEVRILMANGADVNAQDTKGYTPLHLAANSGHLEIVEVLLKNGADVNAQD
KFGKTAFDISIDNGNEDLAEILQAAAHHHHHHGAAEQKLISEEDLNGAA-
3'

PDA8 (Reactive with TDP-43), DNA Sequence:
(SEQ ID NO: 14)
5'-atttggctggcgctggctggtttagttttagcgtttagcgcatcggc
ggactacaaagaggcccagccggccatggacctgggtaagaaactgctgg
aagctgctcgtgctggtcaggacgacgaagttcgtatcctgatggctaac
ggtgctgacgttaacgctcaggacgaagctggtctgactccgctgcacct
ggctgctaaaaacggtcacctggaaatcgttgaagttctgctgaagaacg
gtgctgacgttaacgctcaggacaaattcggtaagaccgctttcgacatc
tccatcgacaacggtaacgaggacctggctgaaatcctgcaagcggccgc
acatcatcatcaccatcacggggccgcagaacaaaaactcatctcagaag
aggatctgaatggggccgcatagactgttgaaagttgtttagcaaaacct
catacagaaaattcatttactaacgtctggaaagacgacaaaactttaga
tcgttacgctaactatgagggctgtctgtggaatgctacaggcgttgtgg
tttgtactggtgacgaaactcagtgttacggtacatgggttcctattggg
cttgctatccctgaaaatgagggtggtggctctgagggtggcggttctga
gggtggcggttctgagggtggcgg-3';

Protein Sequence:
(SEQ ID NO: 15)
5'-IWLALAGLVLAFSASADYKEAQPAMDLGKKLLEAARAGQDDEVRILM
ANGADVNAQDEAGLTPLHLAAKNGHLEIVEVLLKNGADVNAQDKFGKTAF
DISIDNGNEDLAEILQAAAHHHHHHGAAEQKLISEEDLNGAA-3'.

PDA9 (Reactive with Alpha-Synuclein), DNA Sequence:
(SEQ ID NO: 16)
5'-ttggctggcgctggctggtttagttttagcgtttagcgcatcggcgg
actacaaagaggcccagccggccatggacctgggtaagaaactgctggaa
gctgctcgtgctggtcaggacgacgaagttcgtatcctgatggctaacgg
tgctgacgttaacgctgacgaccagttcggtgacactccgctgcacctgg
ctgctatgactggtcacctggaaatcgttgaagttctgctgaagaacggt
gctgacgttaacgctcaggacaaattcggtaagaccgctttcgacatctc
catcgacaacggtaacgaggacctggctgaaatcctgcaagcggccgcac
atcatcatcaccatcacggggccgcagaacaaaaactcatctcagaagag
gatctgaatggggccgcatagactgttgaaagttgtttagcaaaacctca
tacagaaaattcatttactaacgtctggaaagacgacaaaactttagatc
gttacgctaactatgagggctgtctgtggaatgctacaggcgttgtggtt
tgtactggtgacgaaactcagtgttacggtacatgggttcctattgggct
tgctatccctgaaaatgagggtggtggctctgagggtggcggttctgagg
gtggcggttctgagggtggc-3';

Protein Sequence:
(SEQ ID NO: 17)
5'-WLALAGLVLAFSASADYKEAQPAMDLGKKLLEAARAGQDDEVRILMA
NGADVNADDQFGDTPLHLAAMTGHLEIVEVLLKNGADVNAQDKFGKTAFD
ISIDNGNEDLAEILQAAAHHHHHHGAAEQKLISEEDLNGAA-3'.

-continued

PDC1 (Reactive with Tau), DNA Sequence:
(SEQ ID NO: 18)
5'-ggctggcgctggctggtttagttttagcgtttagcgcatcggcggac tacaaagaggcccagccggccatggacctgggtaagaaactgctggaagc tgctcgtgctggtcaggacgacgaagttcgtatcctgatggctaacggtg ctgacgttaacgctgctgacgttaaaggtgaaactccgctgcacctggct gcttgggacggtcacctggaaatcgttgaagttctgctgaagaacggtgc tgacgttaacgctcaggacaaattcggtaagaccgctttcgacatctcca tcgacaacggtaacgaggacctggctgaaatcctgcaagcggccgcacat catcatcaccatcacggggccgcagaacaaaaactcatctcagaagagga tctgaatggggccgcatagactgttgaaagttgtttagcaaaacctcata cagaaaattcatttactaacgtctggaaagacgacaaaactttagatcgt tacgctaactatgagggctgtctgtggaatgctacaggcgttgtggtttg tactggtgacgaaactcagtgttacggtacatgggttcctattgggcttg cta-3';

Protein Sequence:
(SEQ ID NO: 19)
5'-KIWLALAGLVLAFSASADYKEAQPAMDLGKKLLEAARAGQDDEVRIL

MANGADVNAADVKGETPLHLAAWDGHLEIVEVLLKNGADVNAQDKFGKTA

FDISIDNGNEDLAEILQAAAHHHHHHGAAEQKLISEEDLNGAA-3'.

Prospective Identification of DARPin Reactive Biomarkers

Figure 5:
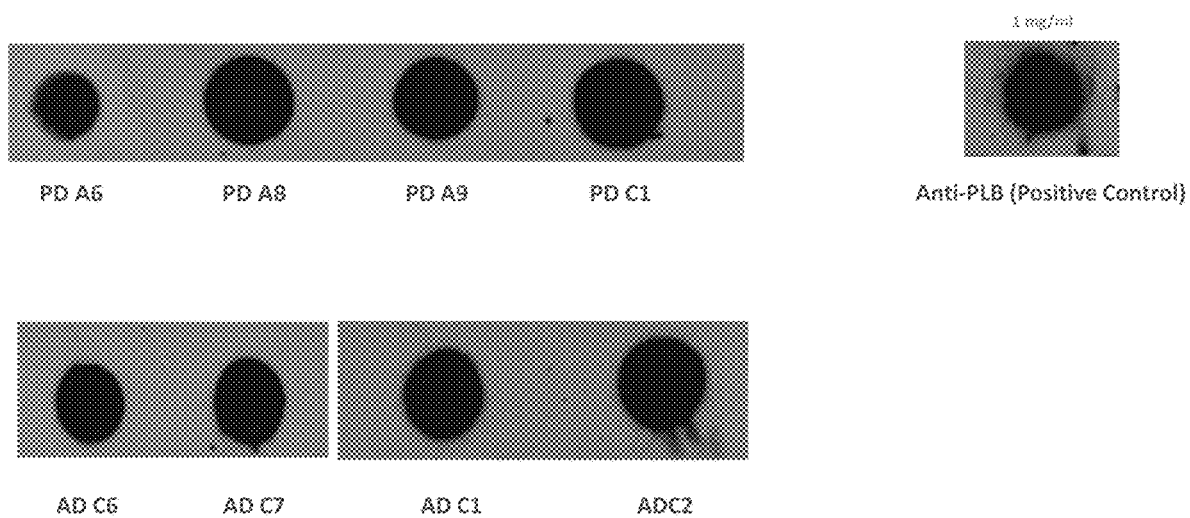
FIG. 5 illustrates protein expression of DARPins in HB2151 cells confirmed by dot blot analysis.

First, the binding specificities of the isolated DARPins for AD or PD was verified using indirect phage ELISA analysis with human brain tissue from their respective targets. Once this was established, protein expression of each DARPin was confirmed using dot blot analysis since this will be important when utilizing these reagents in a phage-capture ELISA system (FIG. 5). In the normal biopanning process, during the positive panning phase, reagents are typically isolated against known targets, for example synthetic or immunoprecipitated variants of beta-amyloid (Aβ), alpha-synulcein (α-syn), tau, etc., are usually added to the mica. Here, the positive biopanning was more general since crude brain tissue or sera was used to identify biomarkers unique to AD or PD. The targets could therefore be variants of Aβ, α-syn, Tar-DNA binding protein 43 (TDP-43), tau, etc. To better ascertain the targets, sandwich ELISAs were completed where DARPins were bound to the wells of 96-well high binding ELISA plates, incubated with either PD or AD brain tissue or sera samples and then detected with commercial antibodies reactive with the most common targets in AD and PD including Aβ, α-syn, TDP-43 and tau. Based on the highest level of reactivity with the different commercial antibodies using the pathologically confirmed human brain tissue and/or sera samples, ADC1 and PDA6 seemed to recognize some variant of Aβ, ADC3 and PDA8 seemed to recognize some variant of TDP-43, ADC6 and PDA9 seemed to recognize some variant of alpha-synuclein and ADC7 and PDC1 seemed to recognize some variant of tau (FIGS. 6-13).

Figure 6:
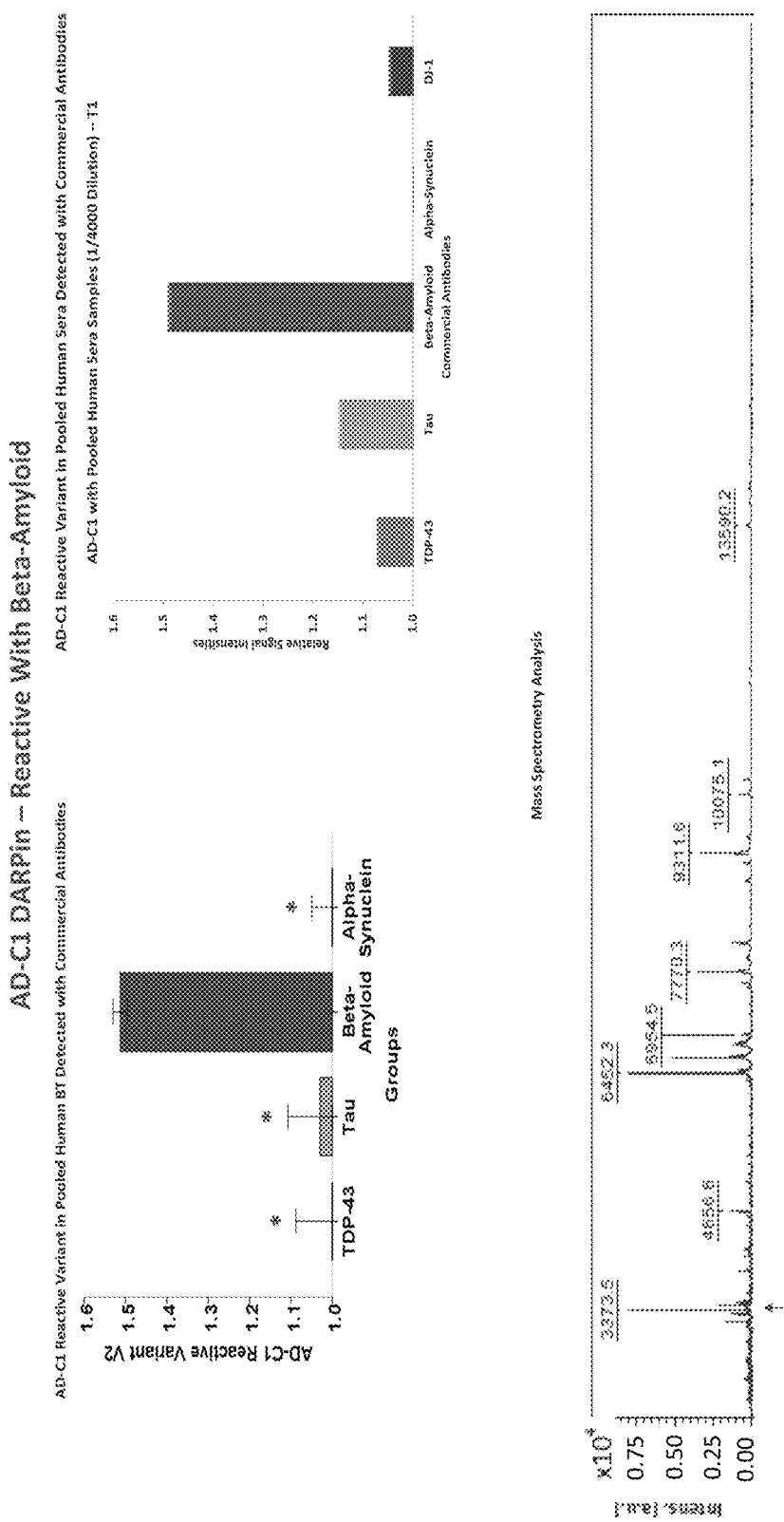
FIGS. 6-13 provide the results based on the highest level of reactivity with different commercial antibodies using the pathologically confirmed human brain tissue and/or sera samples, ADC1 and PDA6 recognized some variant of Aβ; ADC3 and PDA8 recognized some variant of TDP-43; ADC6 and PDA9 recognized some variant of alpha-synuclein; and ADC7 and PDC1 recognized some variant of tau.
Figure 7:
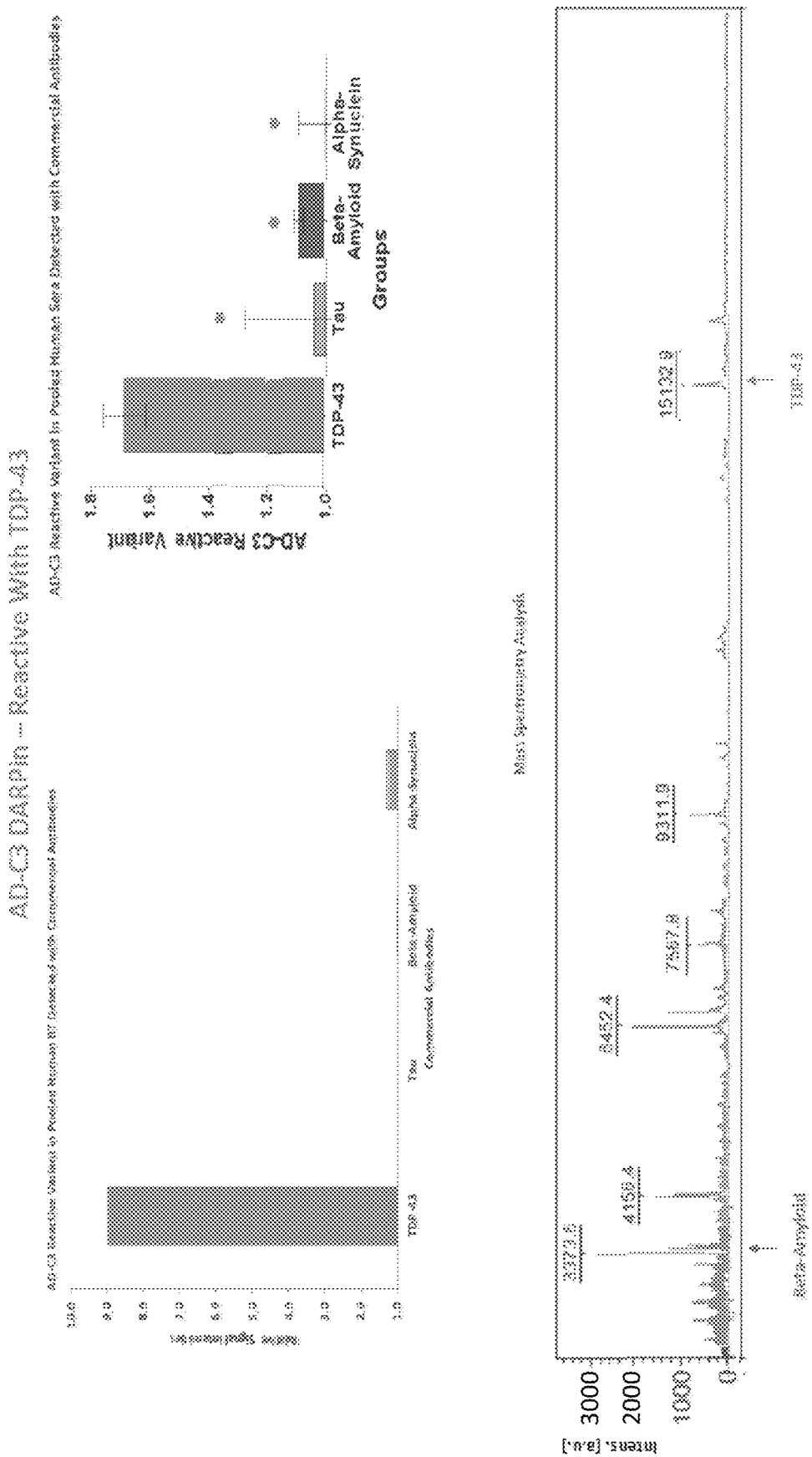
Figure 8:
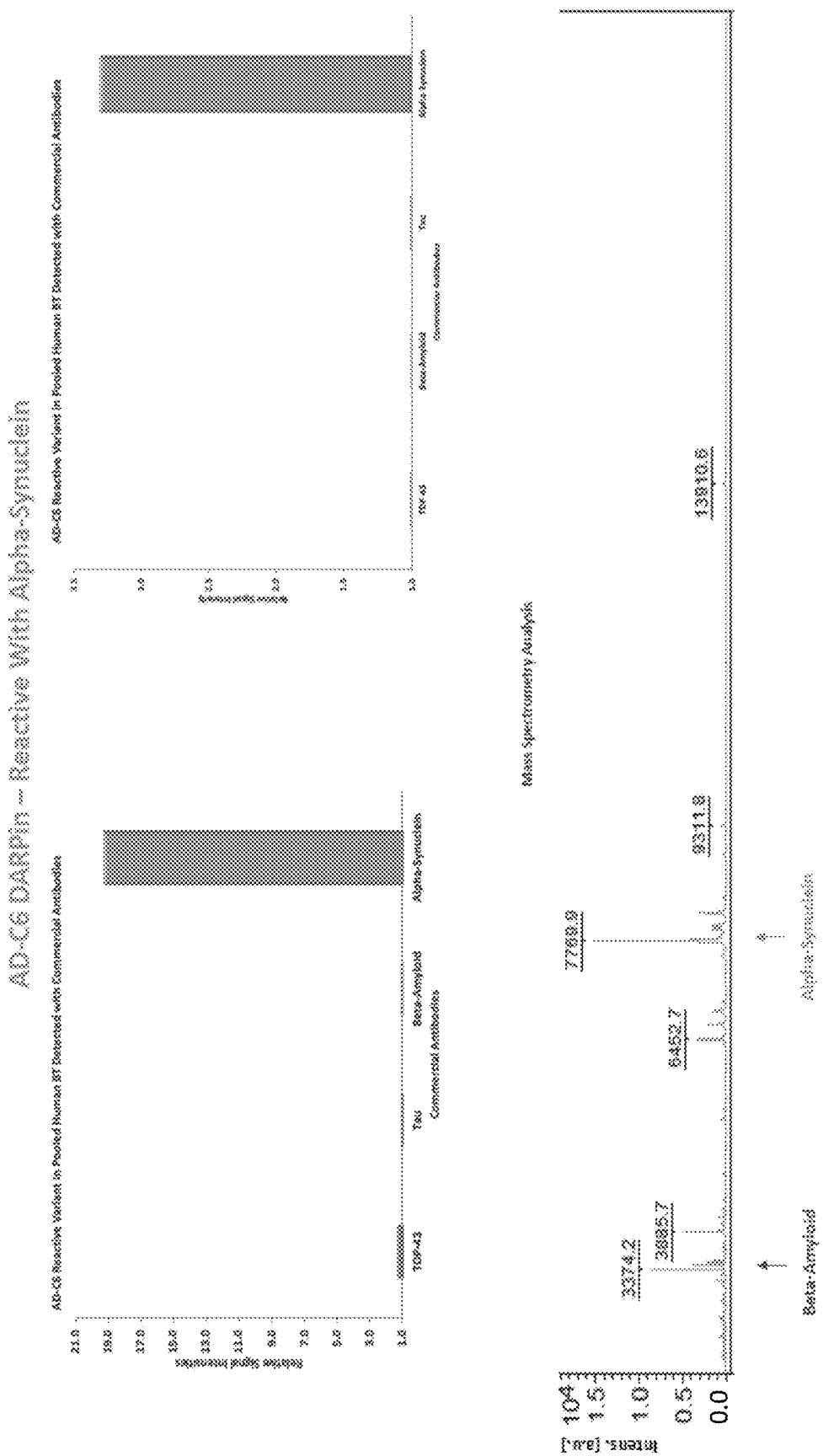
Figure 9:
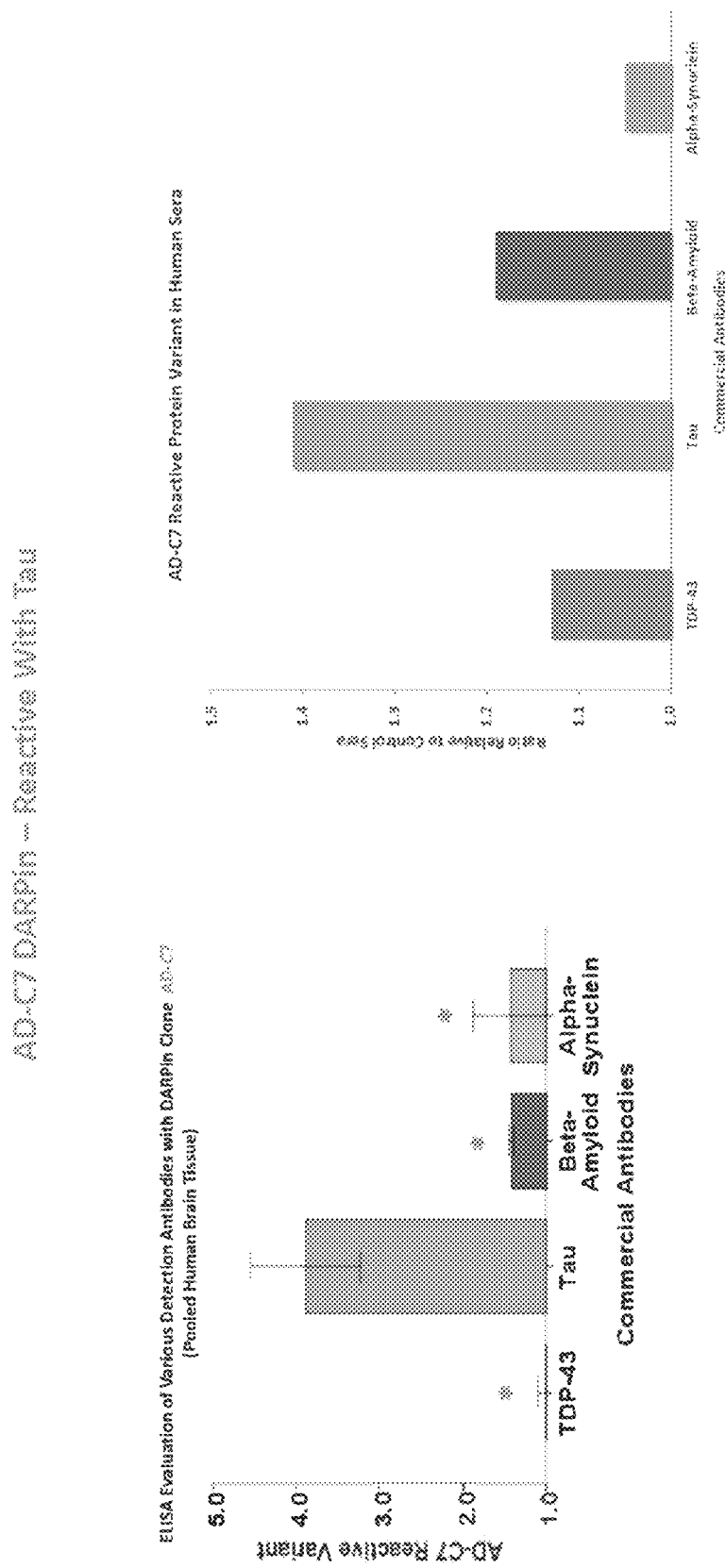
Figure 10:
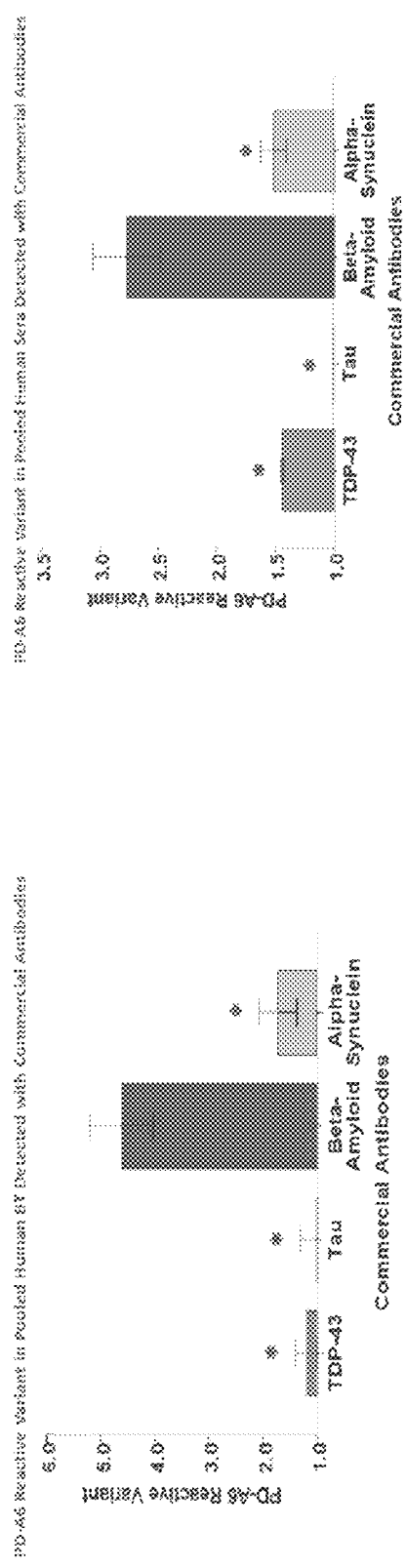
Figure 10:
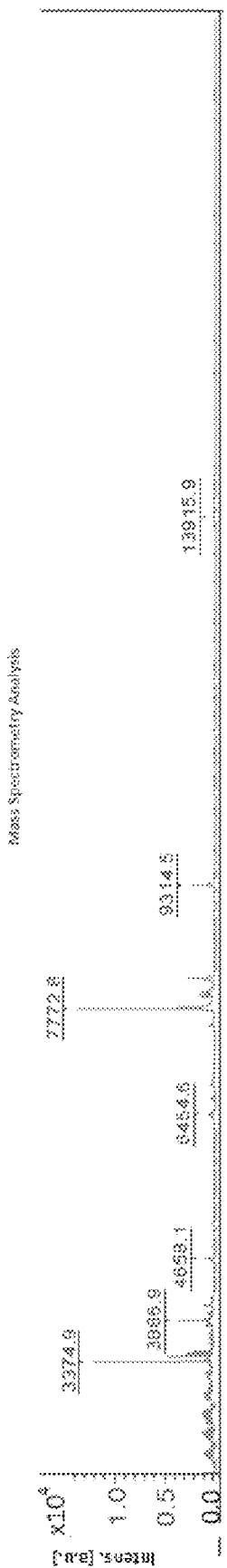
Figure 11:
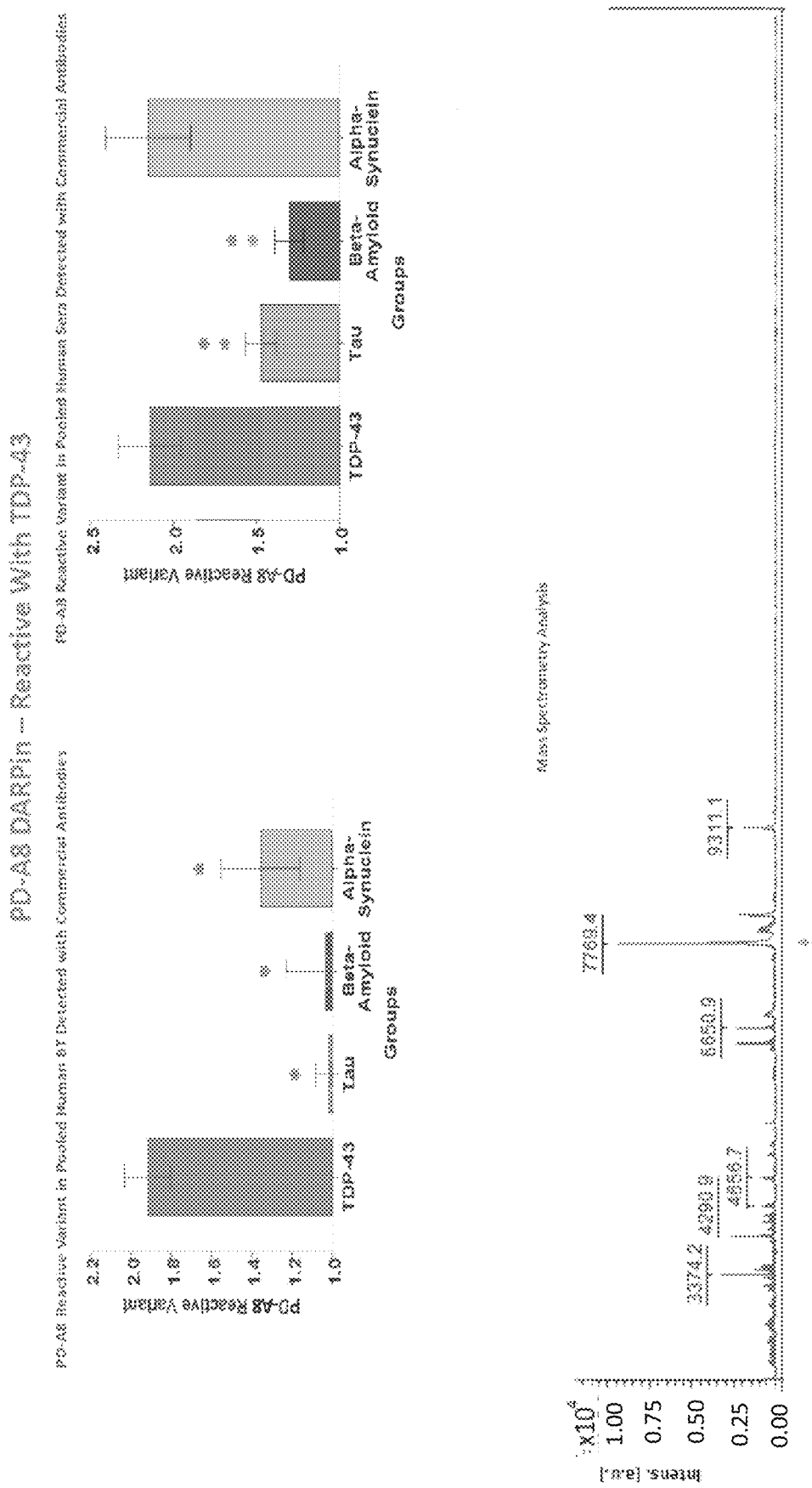
Figure 12:
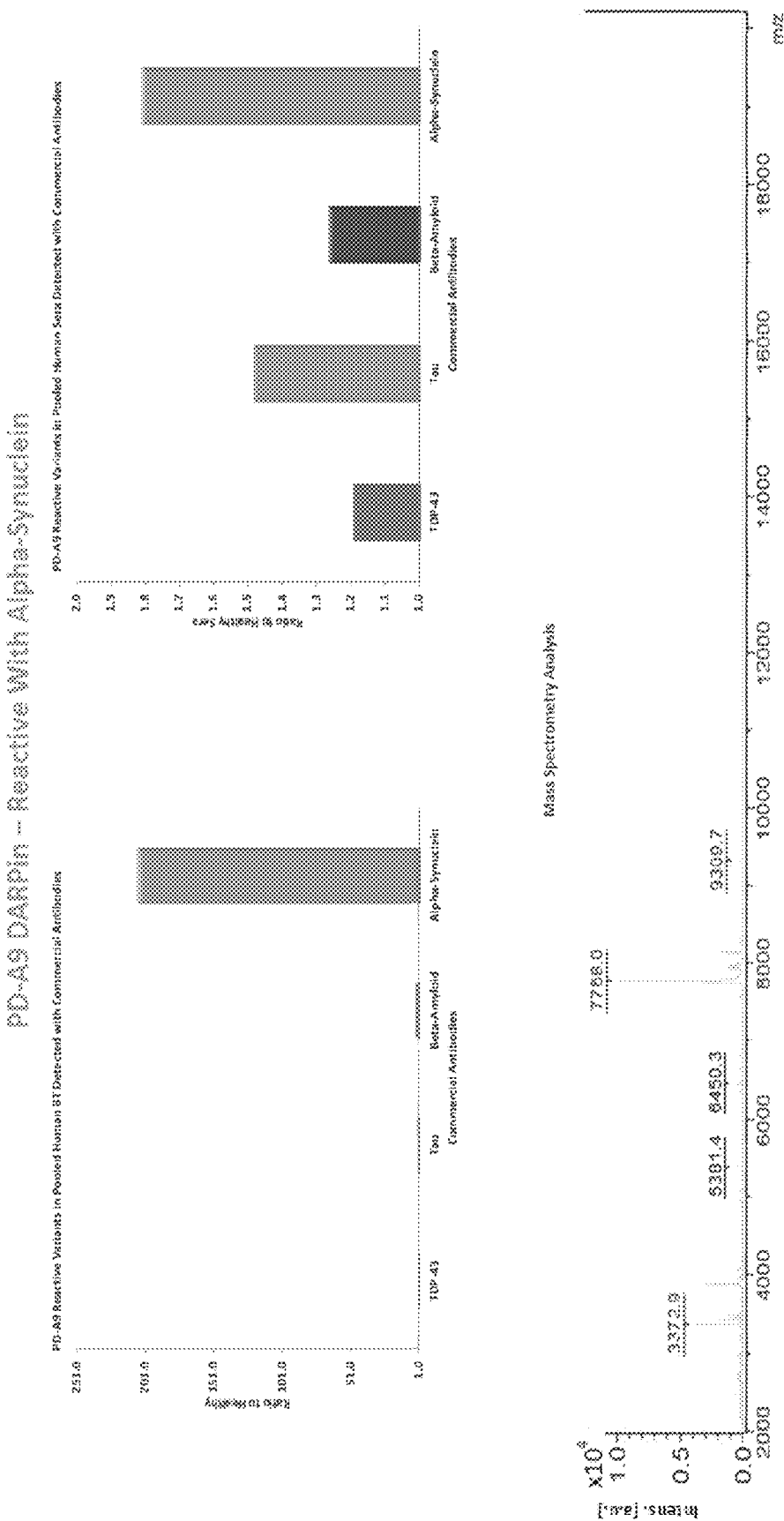
Figure 13:
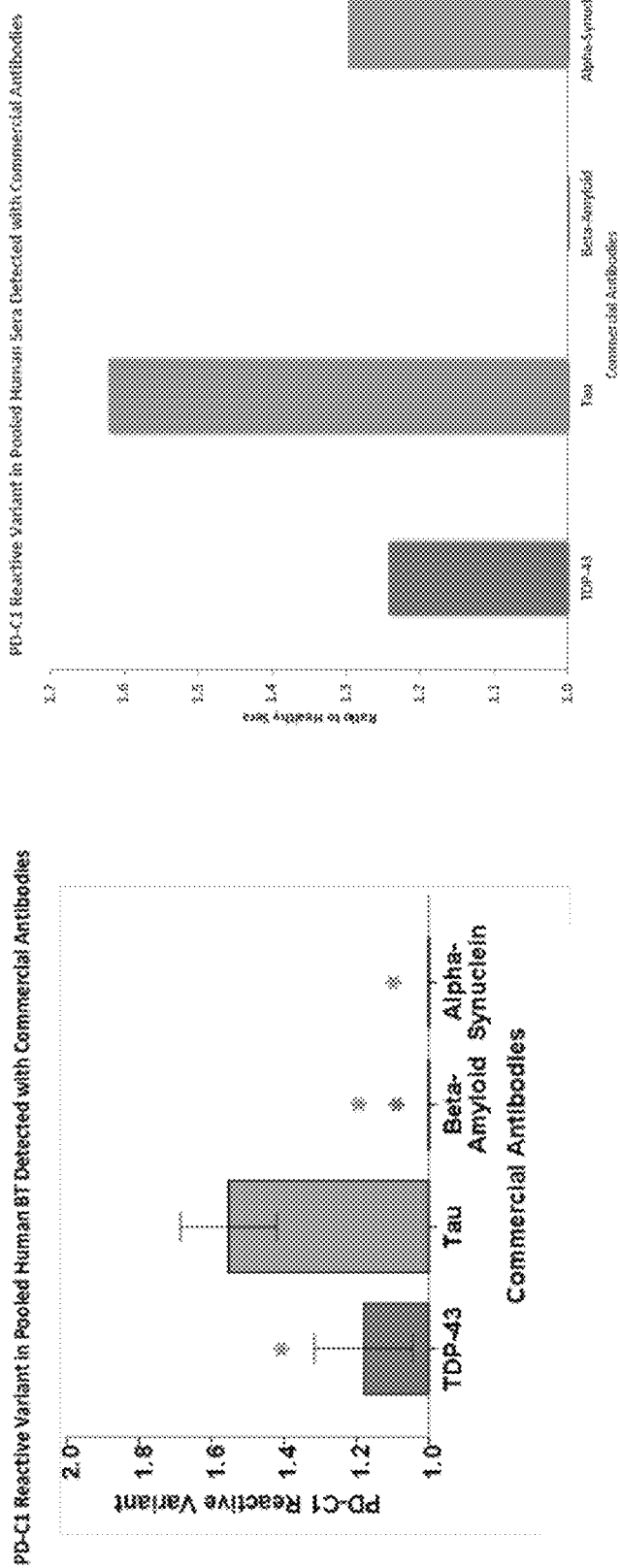

Interestingly, mass spectrometry analysis (using sera) of 3 of the 4 AD reactive DARPins displayed a peak at 3373 Da for all three DARPins which could correspond to a variant of AP (FIGS. 6-8). For ADC3 there was another peak at ~15132 Da, which could be a variant of TDP-43 and with ADC6 there was another peak at 7769 Da, which could correspond to α-syn (FIGS. 7-8). Moving onto the PD reactive DARPins, in 3 of the 4 DARPins that were analyzed, there were peaks at 7772 Da, 7769 Da and 7768 Da, which could correspond to variants of α-syn (FIGS. 10-12). Interestingly, this value is close to the 7769 Da peak with ADC3, which is the AD DARPin also reactive with α-syn. With PDA6, the PD DARPin reactive with Aβ, there was a peak at 3374 Da, which is again close in value to the peaks observed with the 3 AD reactive DARPins (FIG. 10). Interestingly, the potential presence of AP with all 3 AD reactive DARPins and α-syn with all 3 PD reactive DARPins suggests that in AD AP is interacting with the other abnormal variants and in PD α-syn is interacting with the other abnormal variants, which makes sense since AP and α-syn are the major players in AD and PD, respectively. No peaks were detected in the control sera.

To further explore the targets of the different DARPins, immunoprecipitation experiments were completed using human sera samples (FIGS. 14-22). Twenty five longitudinal AD and control sera samples were acquired from Mayo clinic in Florida and analyzed the samples using a panel of scFvs (FIG. 4, Table 1).

Figure 14:
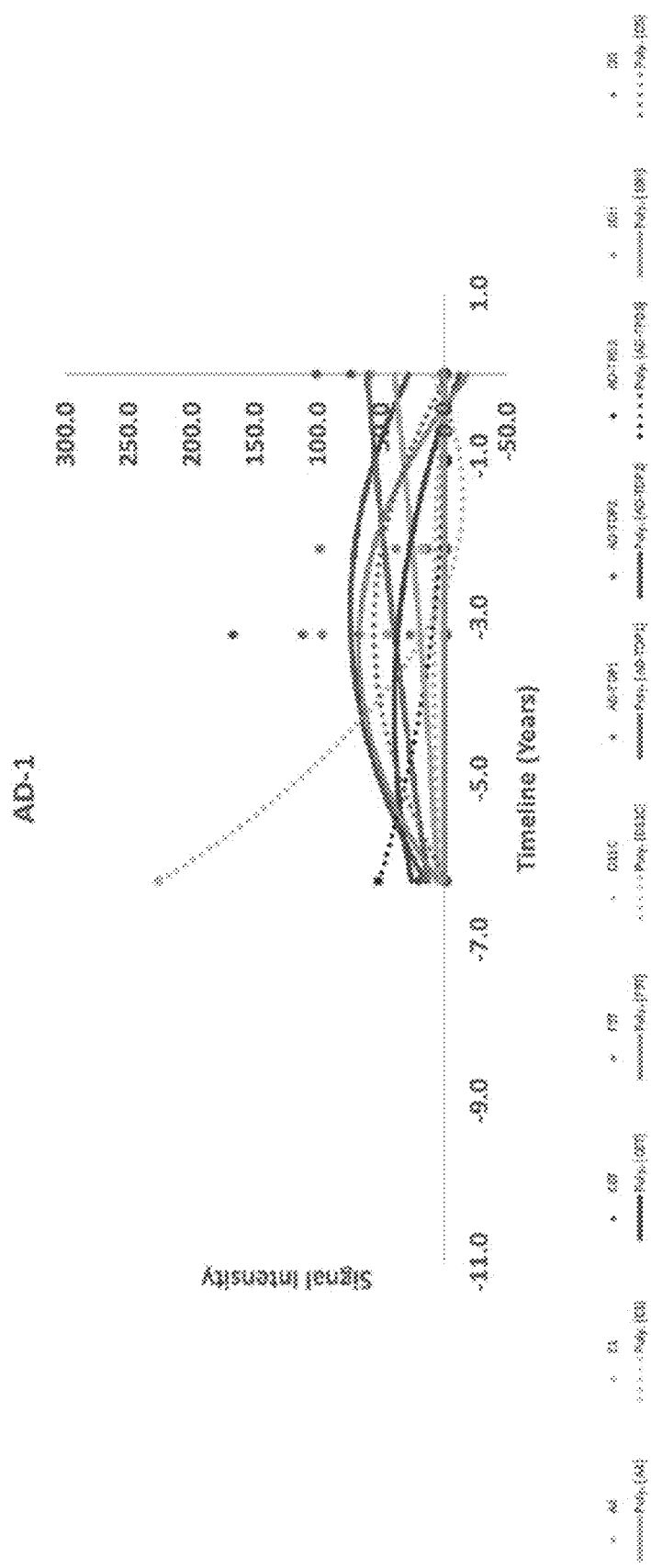
FIGS. 14-22 provide the results of further exploring the targets of the different DARPins, immunoprecipitation experiments completed using human sera samples.
Figure 15:
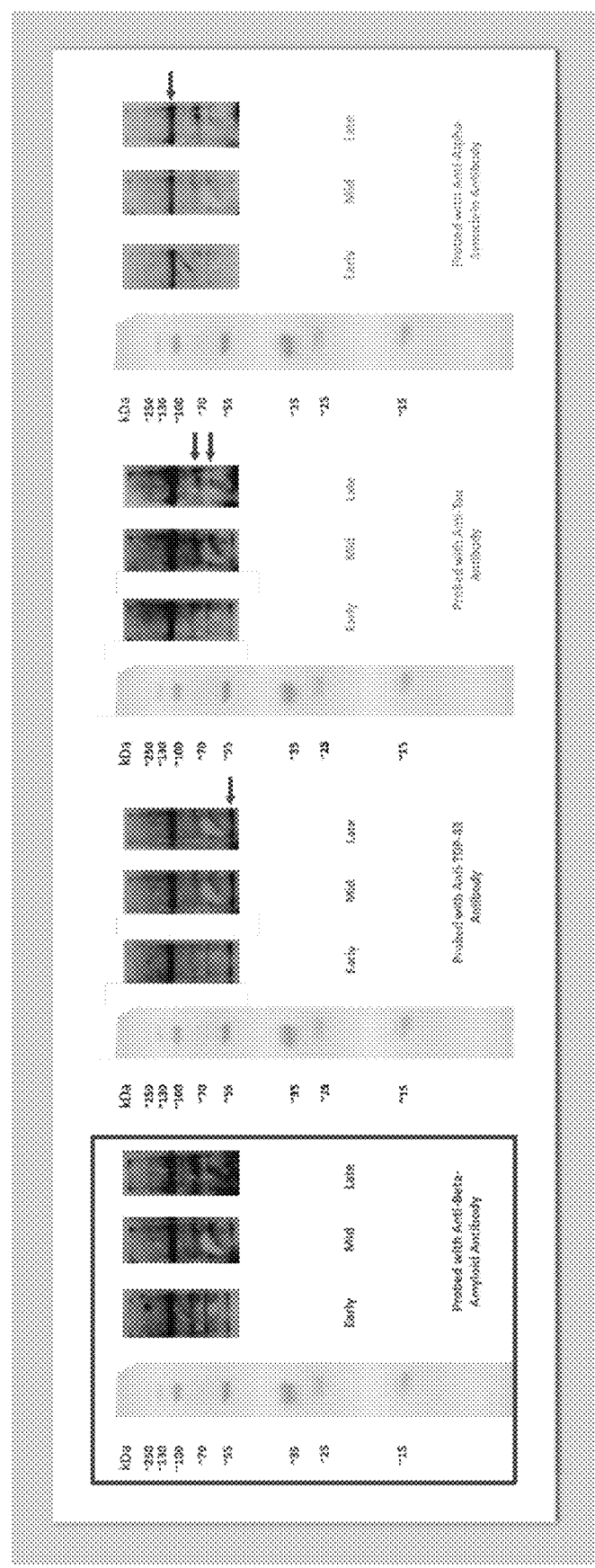
Figure 16:
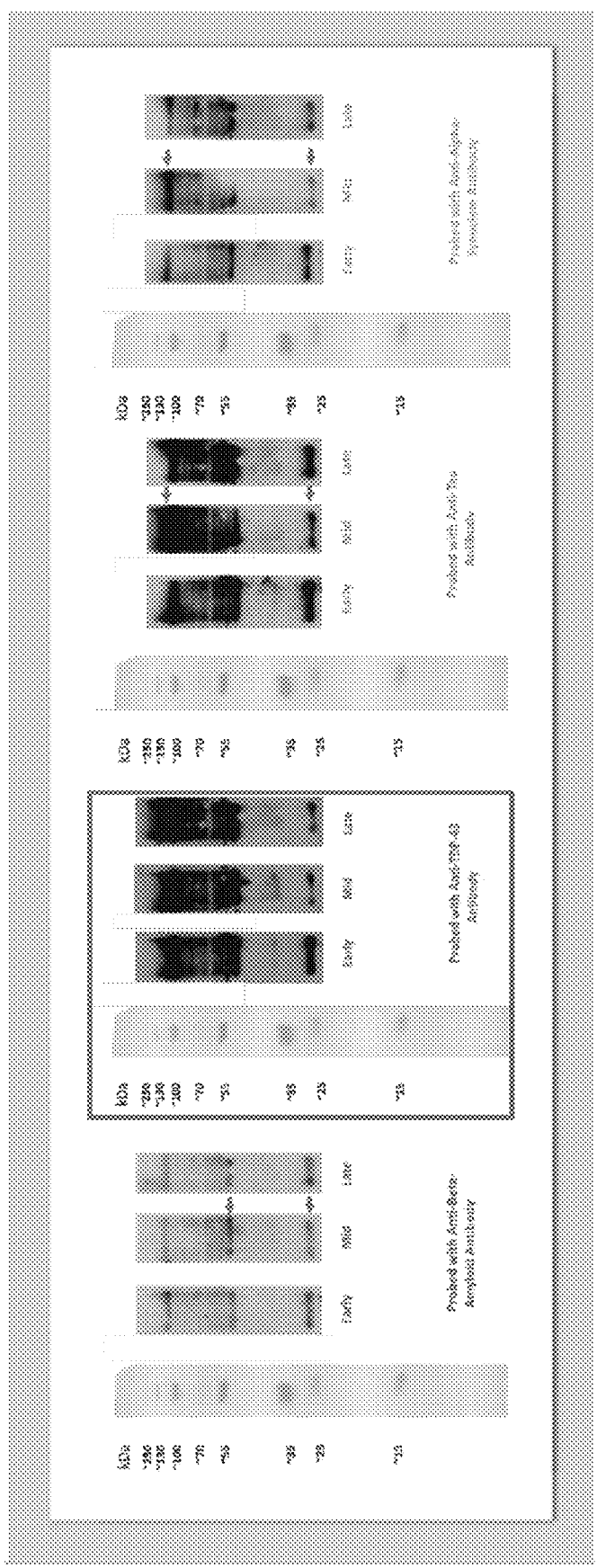
Figure 17:
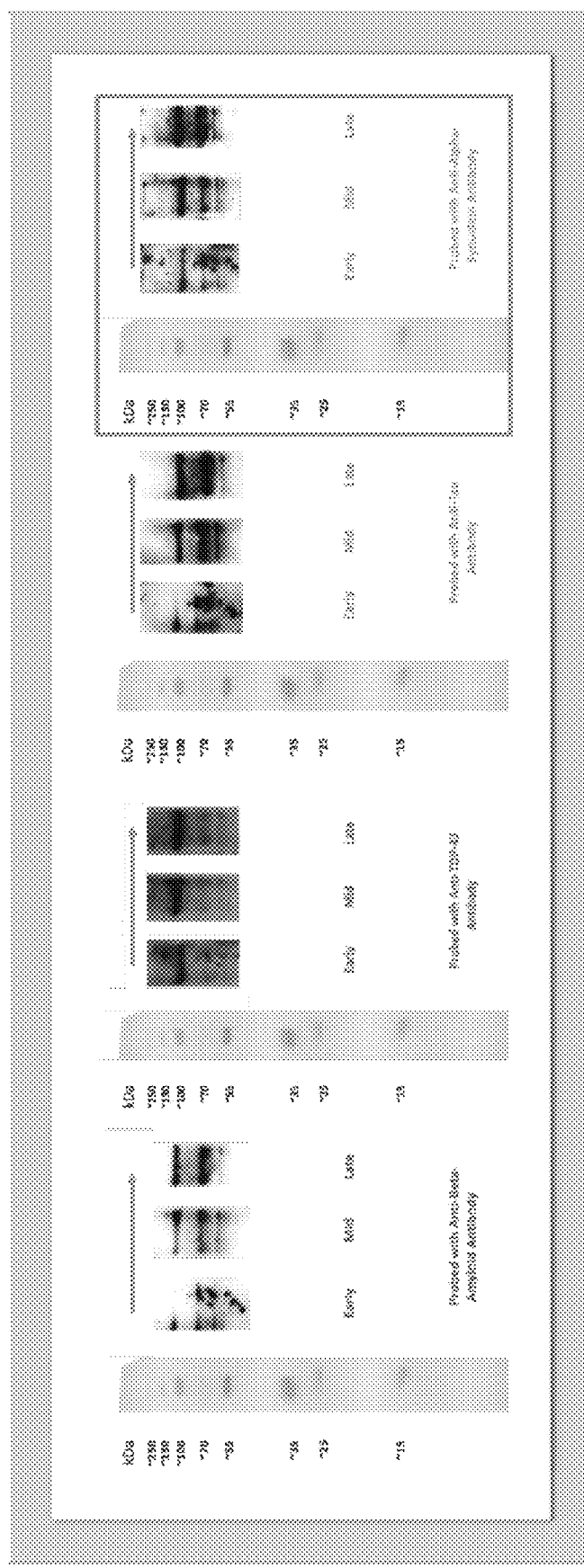
Figure 18:
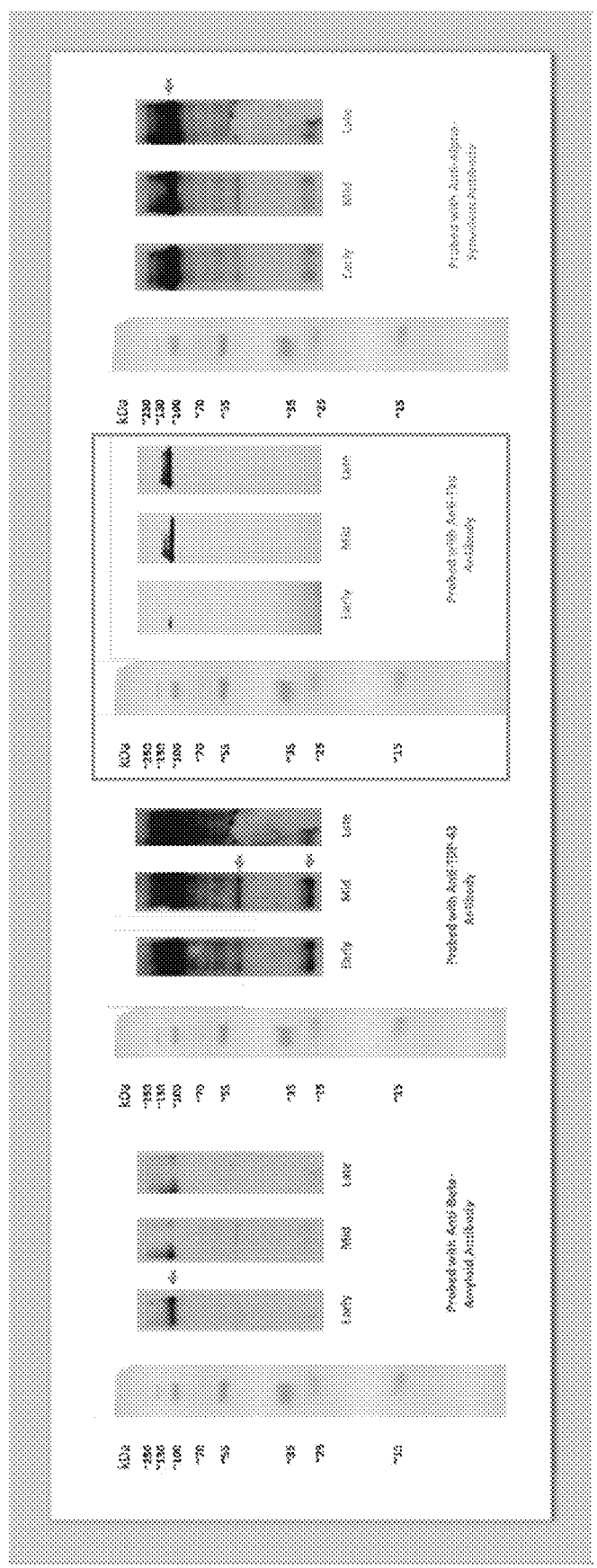
Figure 19:
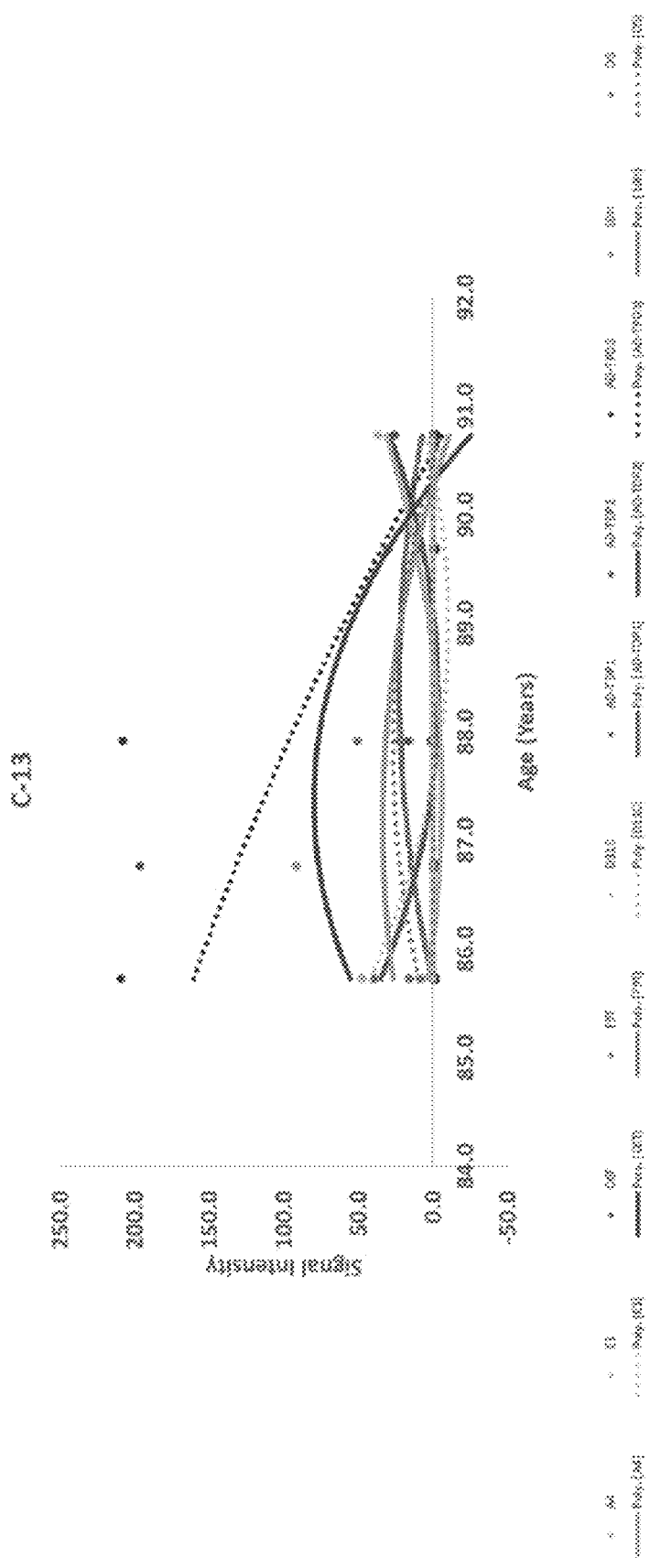

Based on these analyses, the inventors were able to identify the AD cases and some control cases with potential transpiring synucleinopathies. Here, the inventors took one of the AD cases and one of these high-reacting controls with potential synucleinopathies and analyzed the AD case with the 4 AD DARPins and the potential LBD case with the 4 PD DARPins (FIGS. 14,19). Since the cases were longitudinal, immunoprecipitation experiments were performed with three timepoints from each case. The isolated targets were examined on western blots and the proteins identified using the same 4 commercial antibodies used in the ELISAs. ADC1, the AD DARPin reactive with AP variants, produced at least 4 different bands (range of ~54 kDa to ~110 kDa) that were reactive with commercial anti-Aβ antibody (FIG. 15). The same blot re-probed with the anti-TDP-43 antibody generated strong reactivity with the highest and lowest band, with the anti-tau antibody there was strong reactivity with the highest band and little reactivity with the other three lower bands and with the anti-α-syn antibody reactivity was mostly seen with the highest molecular weight band (FIG. 15). ADC3, the AD DARPin reactive with TDP-43, generated strong reactivity with a ~25 kDa band and a large smear of reactivity starting at ~43 kDa to ~130 kDa (FIG. 16). Interestingly, the ~25 kDa band was at its highest concentration at the earliest timepoint and the intensity of this lower molecular weight band seemed to decrease over time. The same blot re-probed with the anti-Aβ antibody showed significantly less reactivity and mostly so with the bands at ~25 kDa, ~43 kDa and above ~100 kDa. With the anti-tau antibody there was strong reactivity with the ~25 kDa band and a large smear of reactivity starting at ~43 kDa to ~130 kDa, although the reactivity was less than that of TDP-43 and lastly, with the anti-α-syn antibody there was some reactivity with the ~25 kDa, ~43 kDa and above ~100 kDa bands. ADC6, the AD DARPin reactive with α-syn, produced three high molecular weight bands that seemed to increase in intensity across the timepoints (FIG. 17). Re-probing with the anti-Aβ antibody revealed significantly less reactivity with the three bands, although the intensity does seem to increase across time. With the anti-TDP-43 antibody most of the reactivity was with the highest band and again the intensity increased across time while with the anti-tau antibody the reactivity did increased across time and with all three bands. ADC7, the AD DARPin reactive with tau, produced one high molecular weight bands that seemed to increase in intensity across the timepoints (FIG. 18). Re-probing with the anti-Aβ antibody revealed strong reactivity at the earliest timepoint with decreasing intensity across time. With the anti-TDP-43 antibody there was a smear of bands and especially strong reactivity with lower molecular weight bands while with the anti-α-syn antibody the reactivity was mostly seen with the high molecular weight band.

Figure 20:
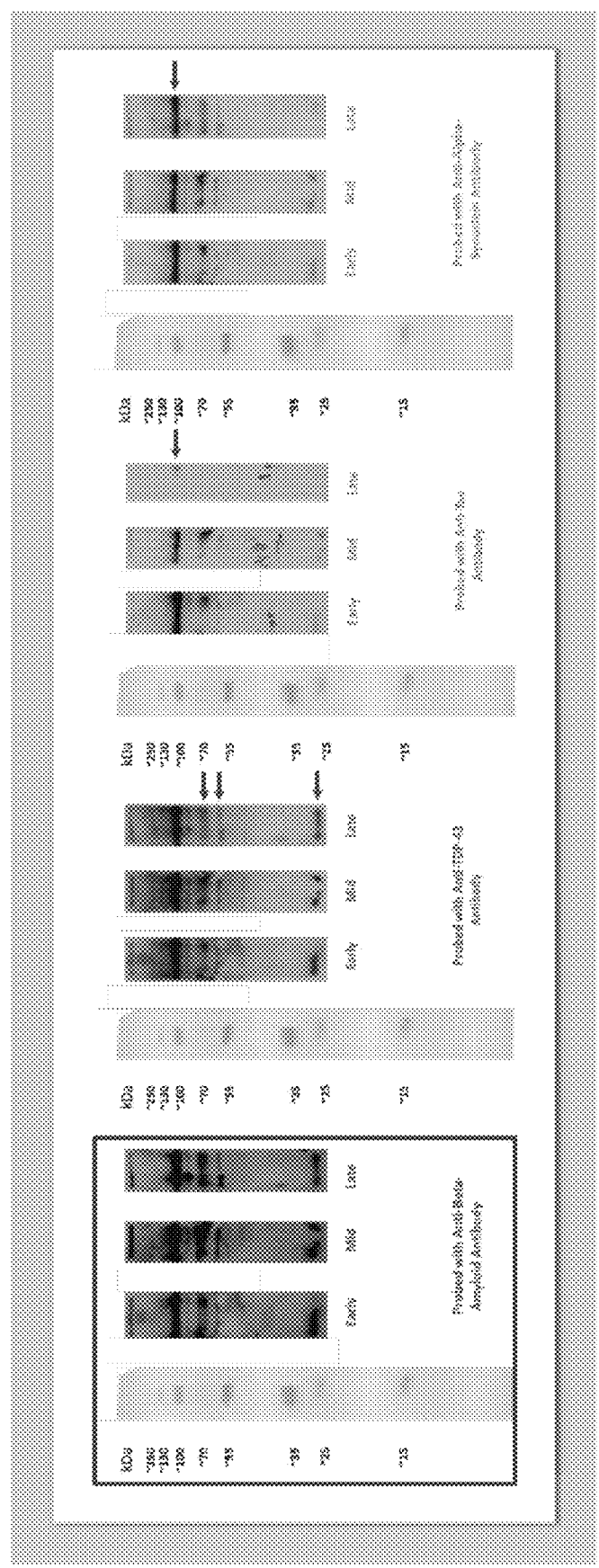
Figure 21:
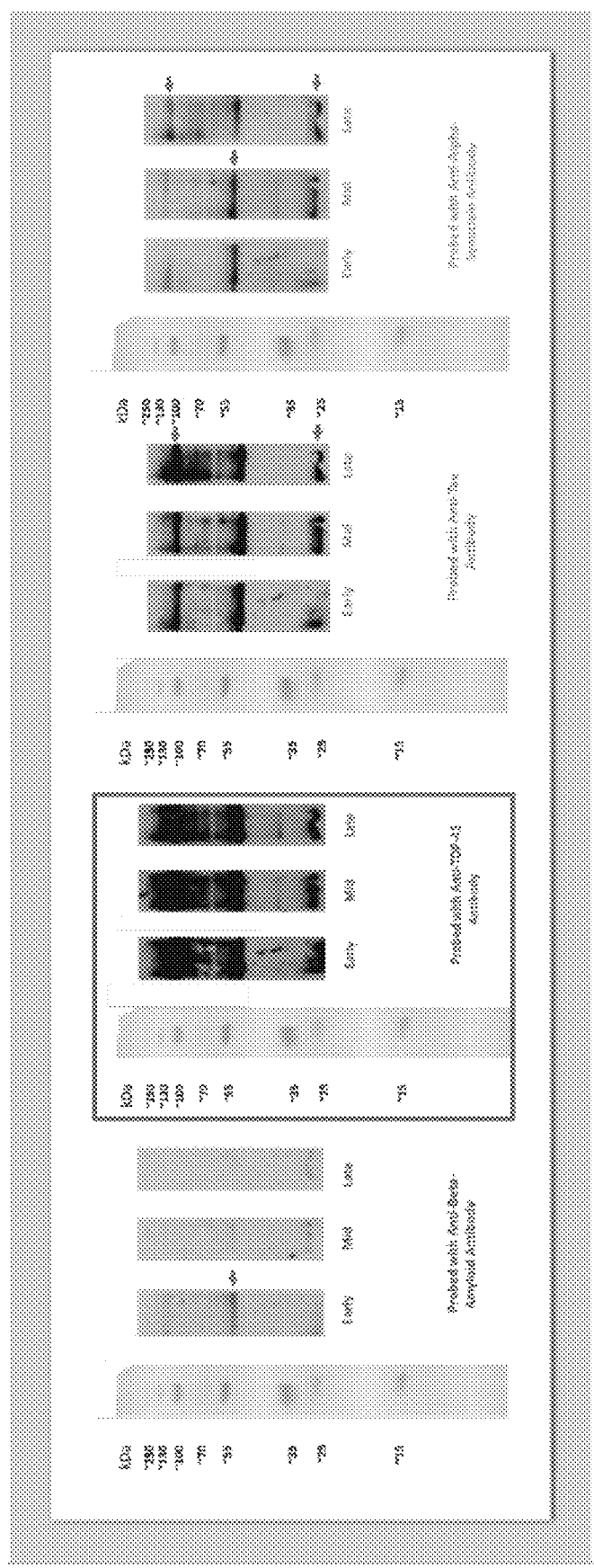
Figure 22:
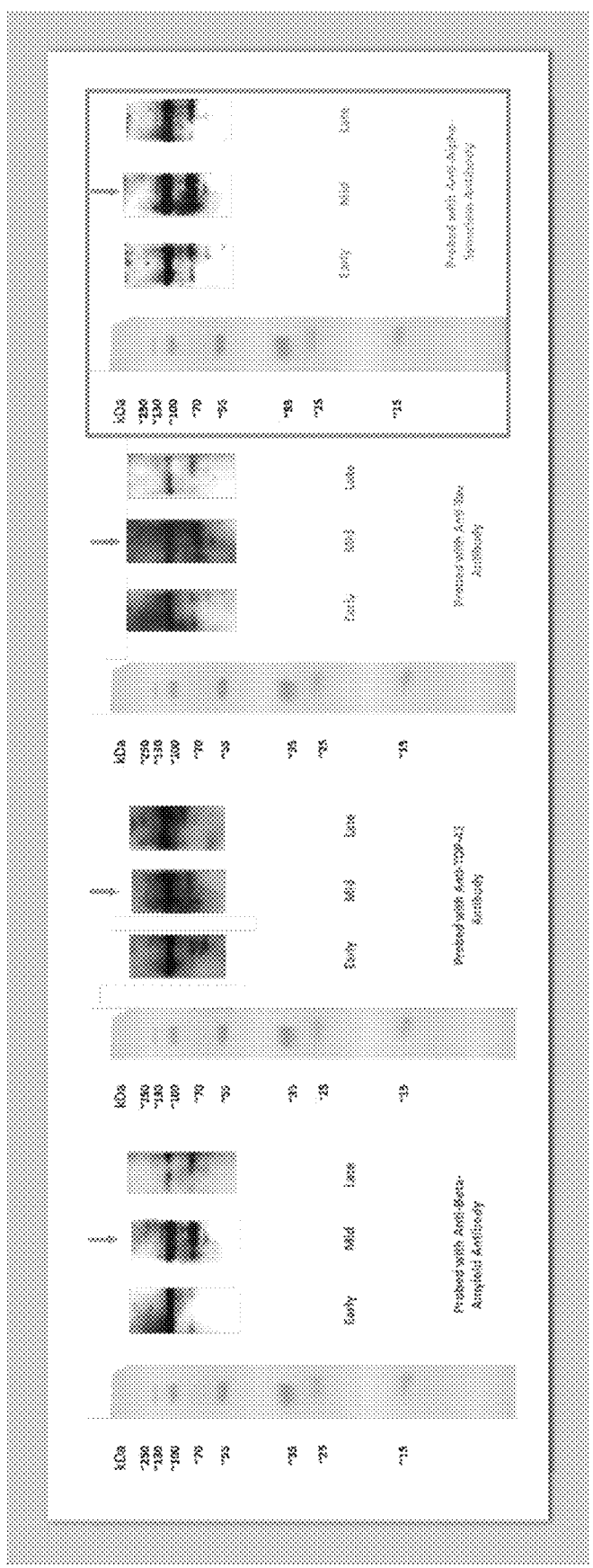
Figure 23:
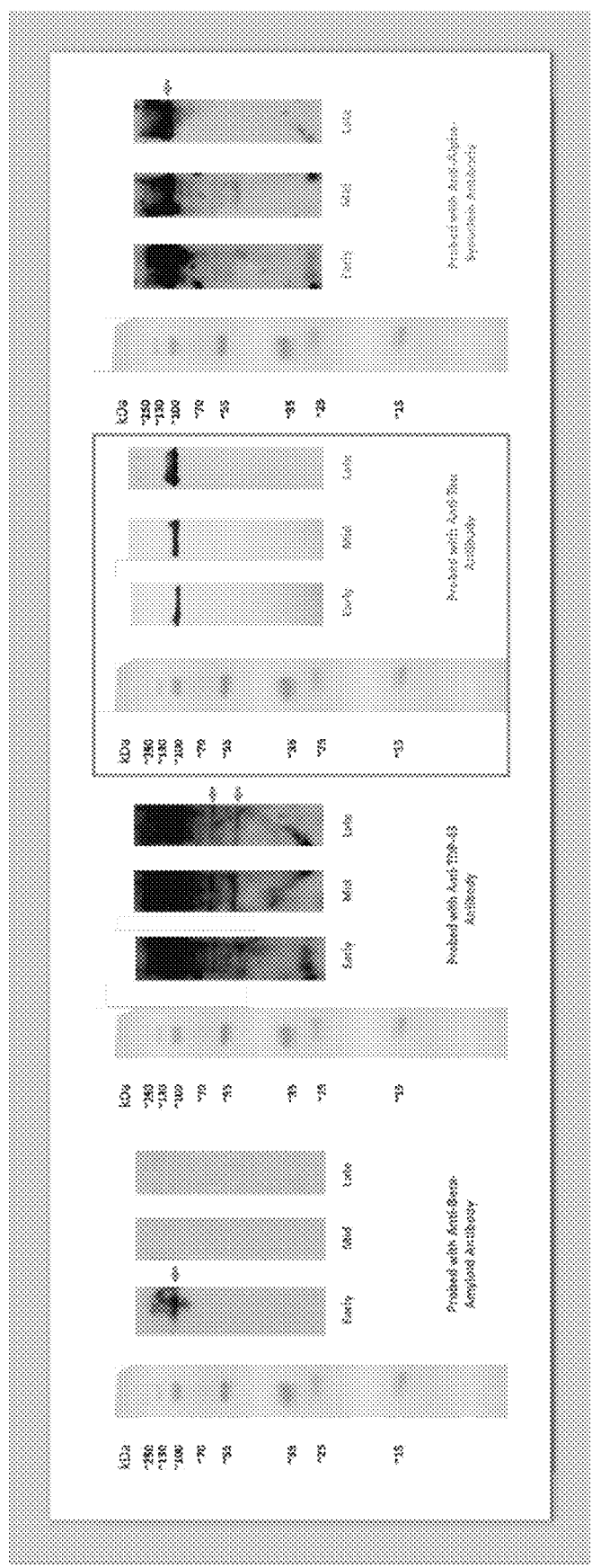
FIG. 23 illustrates that PDC1, the PD DARPin reactive with tau, produced one high molecular weight bands that seemed to increase in intensity across the timepoints.
Figure 24:
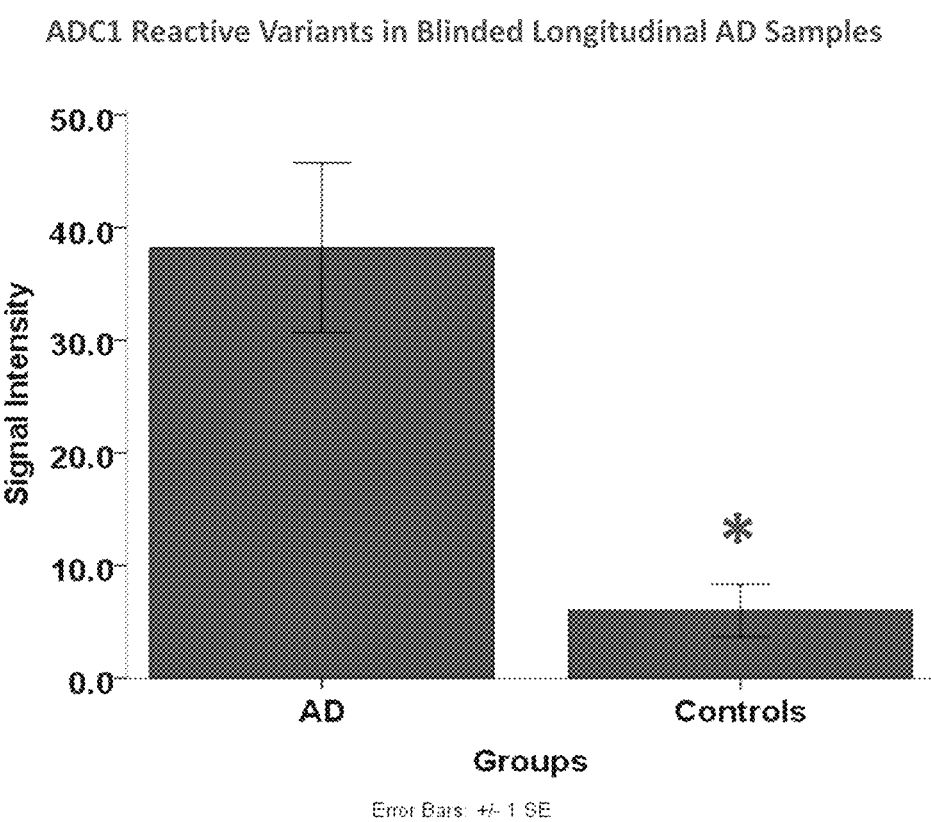
FIGS. 24-27 illustrate that ADC1, ADC3, ADC6 and ADC7 all displayed significantly higher reactivity with the AD cases compared to the controls.
Figure 25:
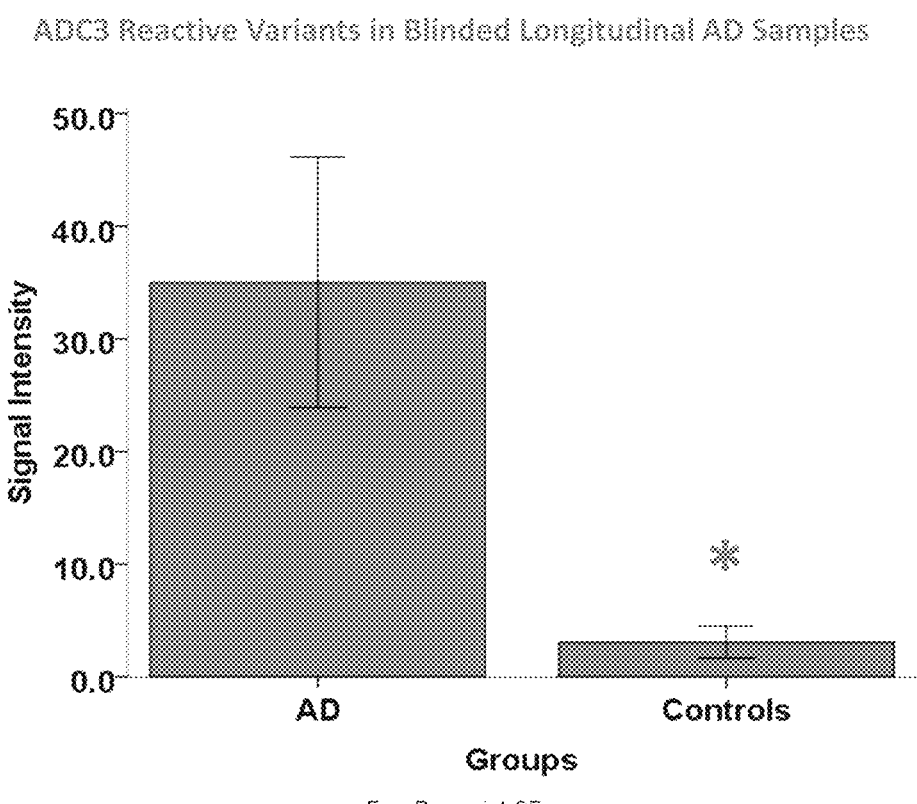
Figure 26:
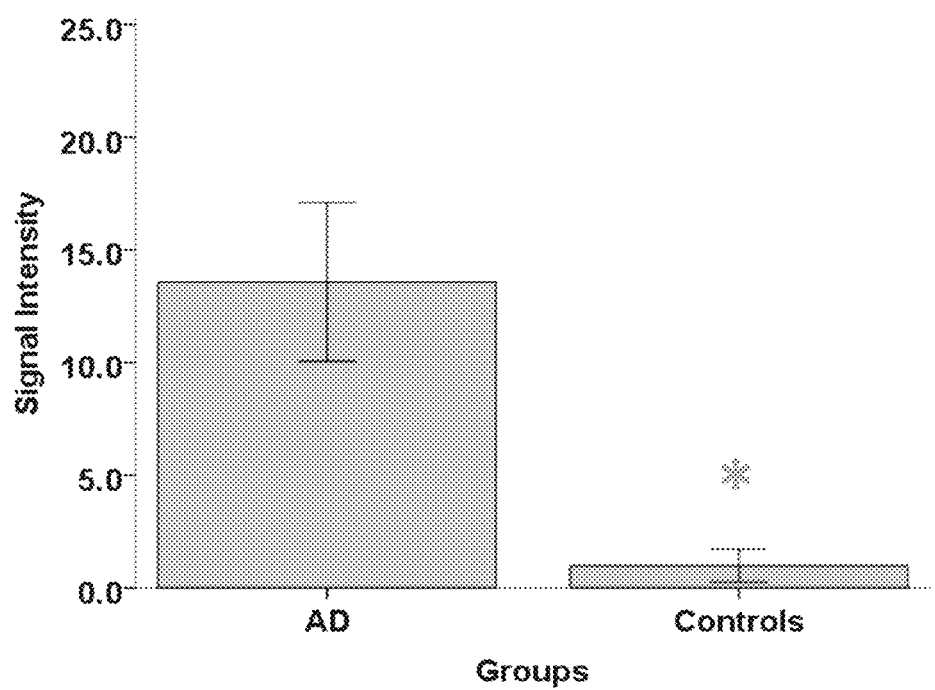
Figure 27:
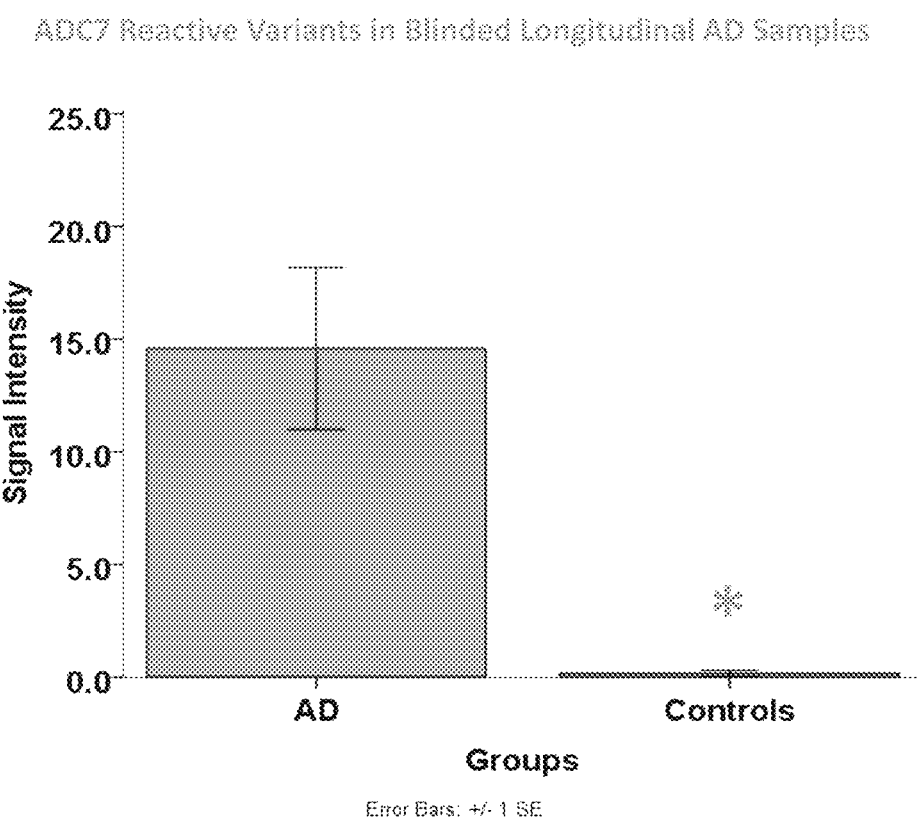
Figure 28:
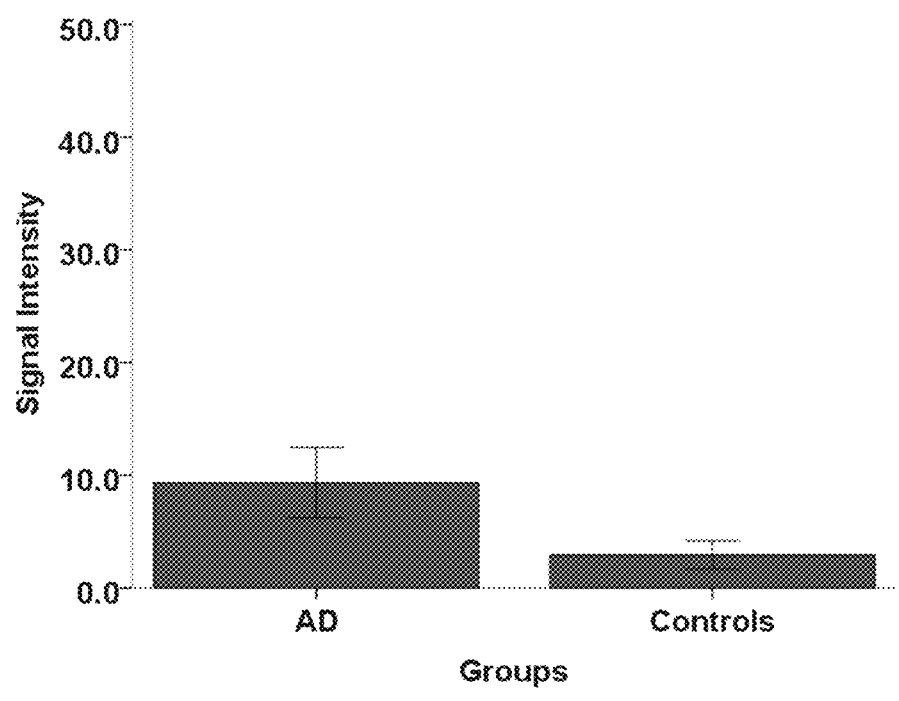
FIGS. 28-31 illustrate there was no difference in the reactivity between the AD and controls cases with the PDA6, PDA8, PDA9 and PDC1 DARPins.
Figure 29:
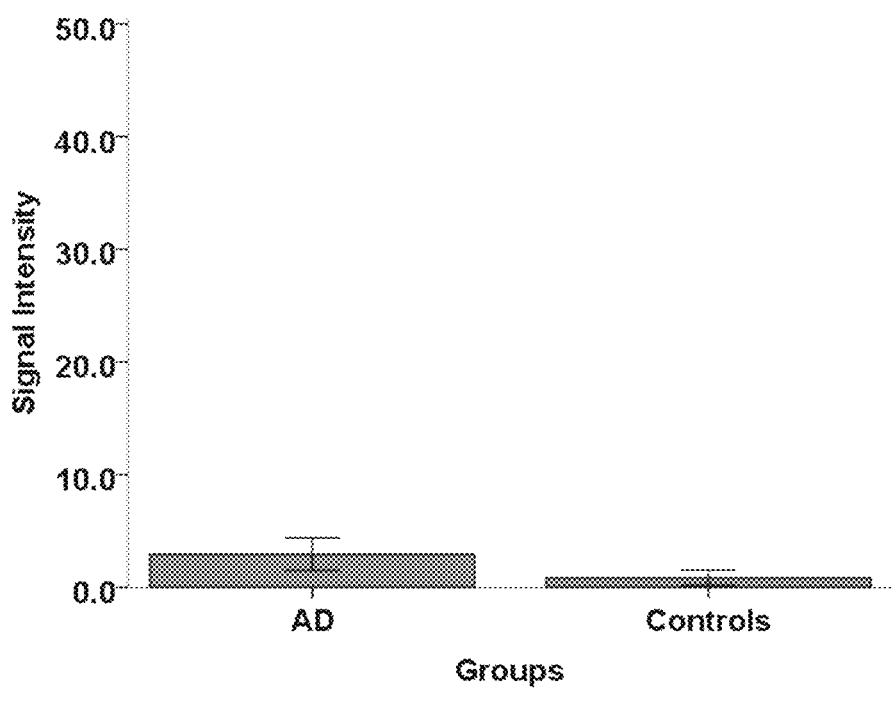
Figure 30:
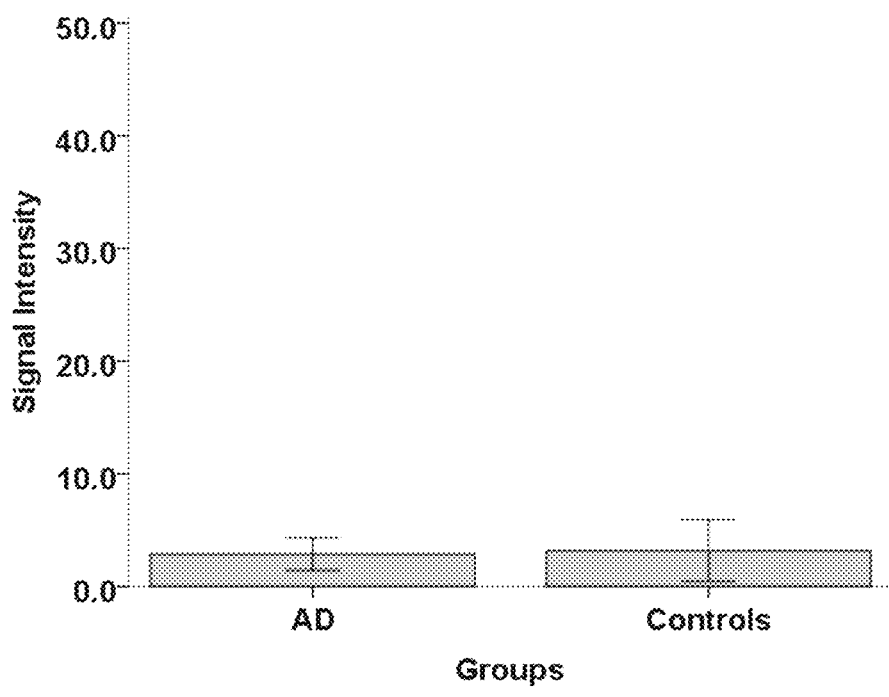
Figure 31:
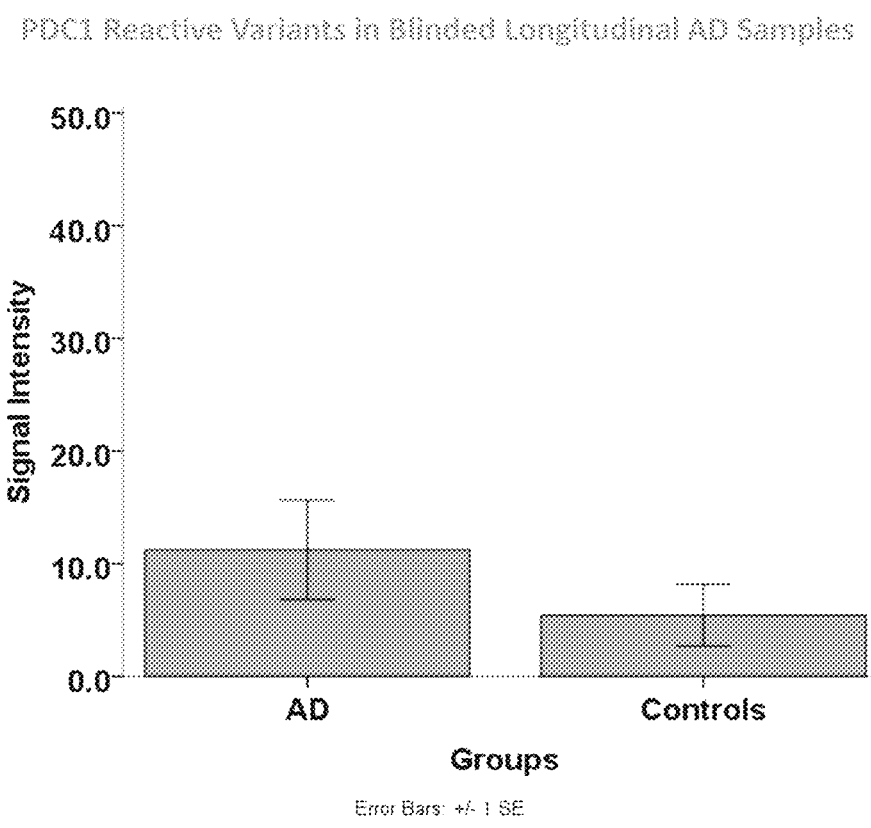

Moving onto the PD Reactive DARPins, PDA6, the PD DARPin reactive with AP variants, produced at least 4 different bands (one at ~25 kDa and three in the range of ~60 kDa to ~110 kDa) that were reactive with commercial anti-Aβ antibody (FIG. 20). The same blot re-probed with anti-TDP-43 antibody generated the strongest reactivity with the highest and lowest bands and some reactivity with the middle bands, with the anti-tau antibody there was strong reactivity with the highest band especially at the first and second timepoint and with the anti-α-syn antibody similar reactivity was mostly seen with the highest molecular weight band (FIG. 20). PDA8, the PD DARPin reactive with TDP-43, generated strong reactivity with a ~25 kDa band and a large smear of reactivity starting at ~43 kDa to ~130 kDa (FIG. 21). The same blot re-probed with the anti-Aβ antibody showed little to no reactivity, except with the ~43 kDa band at the first timepoint. With the anti-tau antibody there was strong reactivity with the ~25 kDa, ~43 kDa and ~100 kDa bands although the reactivity was less than that of TDP-43 and with the anti-α-syn antibody there was strong reactivity with the ~25 kDa and ~43 kDa bands. PDA9, the PD DARPin reactive with α-syn, produced two high molecular weight bands that seemed to be most intense at the middle timepoint (FIG. 22). Re-probing with the anti-Aβ, anti-TDP-43 or anti-tau antibodies revealed the strongest reactivity was also at the middle timepoint and interestingly the highest reactivity at the earliest timepoint was with the anti-α-syn antibody. PDC1, the PD DARPin reactive with tau, produced one high molecular weight bands that seemed to increase in intensity across the timepoints (FIG. 23). Re-probing with the anti-Aβ antibody revealed little to no reactivity, with the anti-TDP-43 antibody there was a smear of bands starting at ~55 kDa and with the anti-α-syn antibody reactivity was mostly seen with the high molecular weight band.

These results indicate that the antigens recognized by the 4 AD DARPins are different from each other and the antigens recognized by the 4 PD DARPins are also different from each other. However, the re-probing results also indicates that these protein variants have a high degree of interaction with each other which may provide valuable insight into the pathology of the different diseases. For most of the DARPins, the highest level of reactivity seen on the western blot was usually with the commercial antibody that detects the target identified by our ELISAs. It is important to note that these results are based on one AD and potentially LBD case.

Disease Selectivity of DARPins

Figure 32:
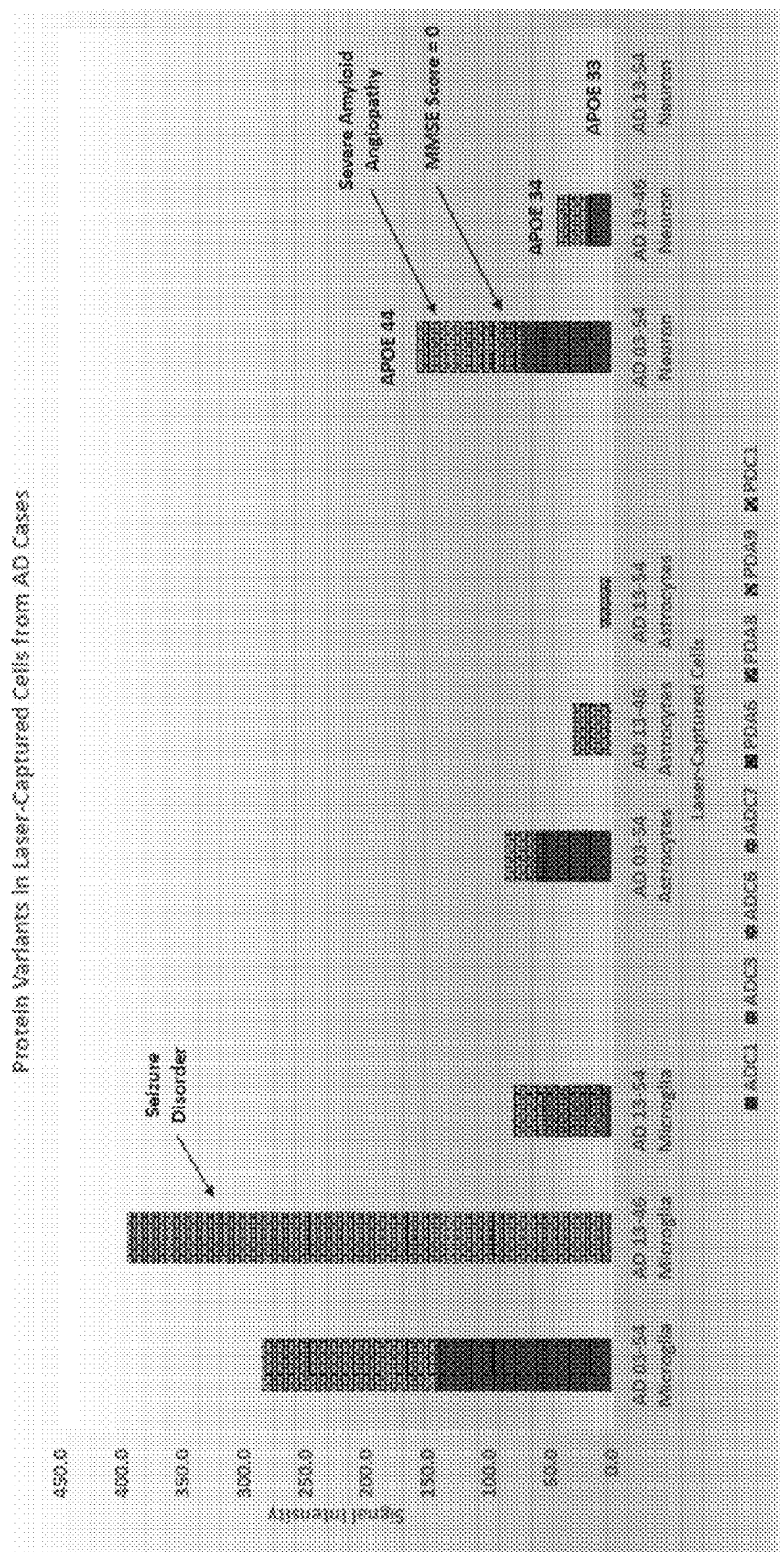
FIG. 32 illustrates the analysis of 3 AD cases with the AD DARPins (horizontal bricks with different background shades) and PD DARPins (checker pattern with different background shades) which resulted in strong reactivity with the AD DARPins and no reactivity with the PD DARPins.
Figure 33:
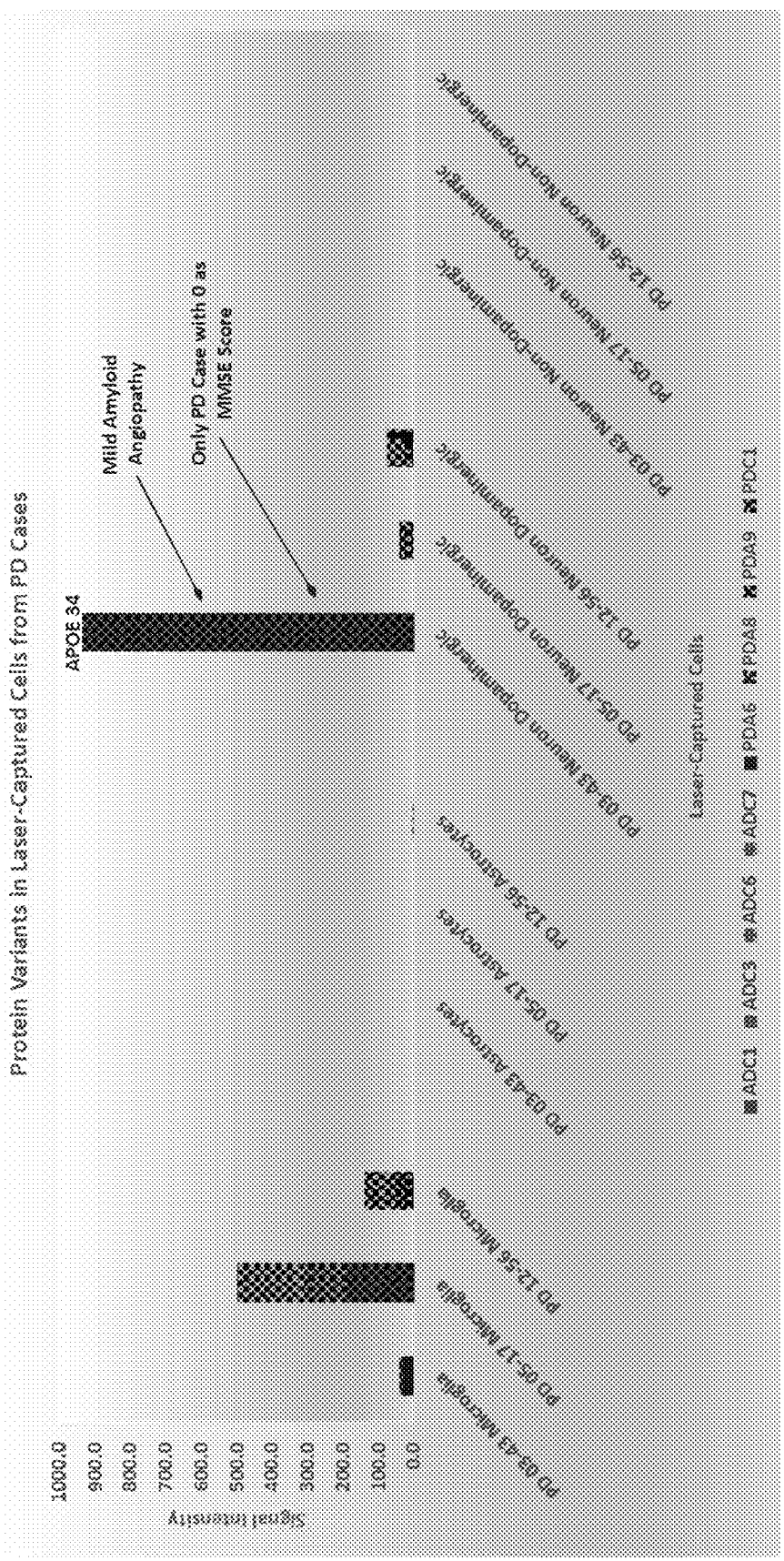
FIG. 33 illustrates analysis of the PD cases with the AD and PD DARPins resulted in strong reactivity with PD DARPins and no reactivity with the AD DARPins.
Figure 34:
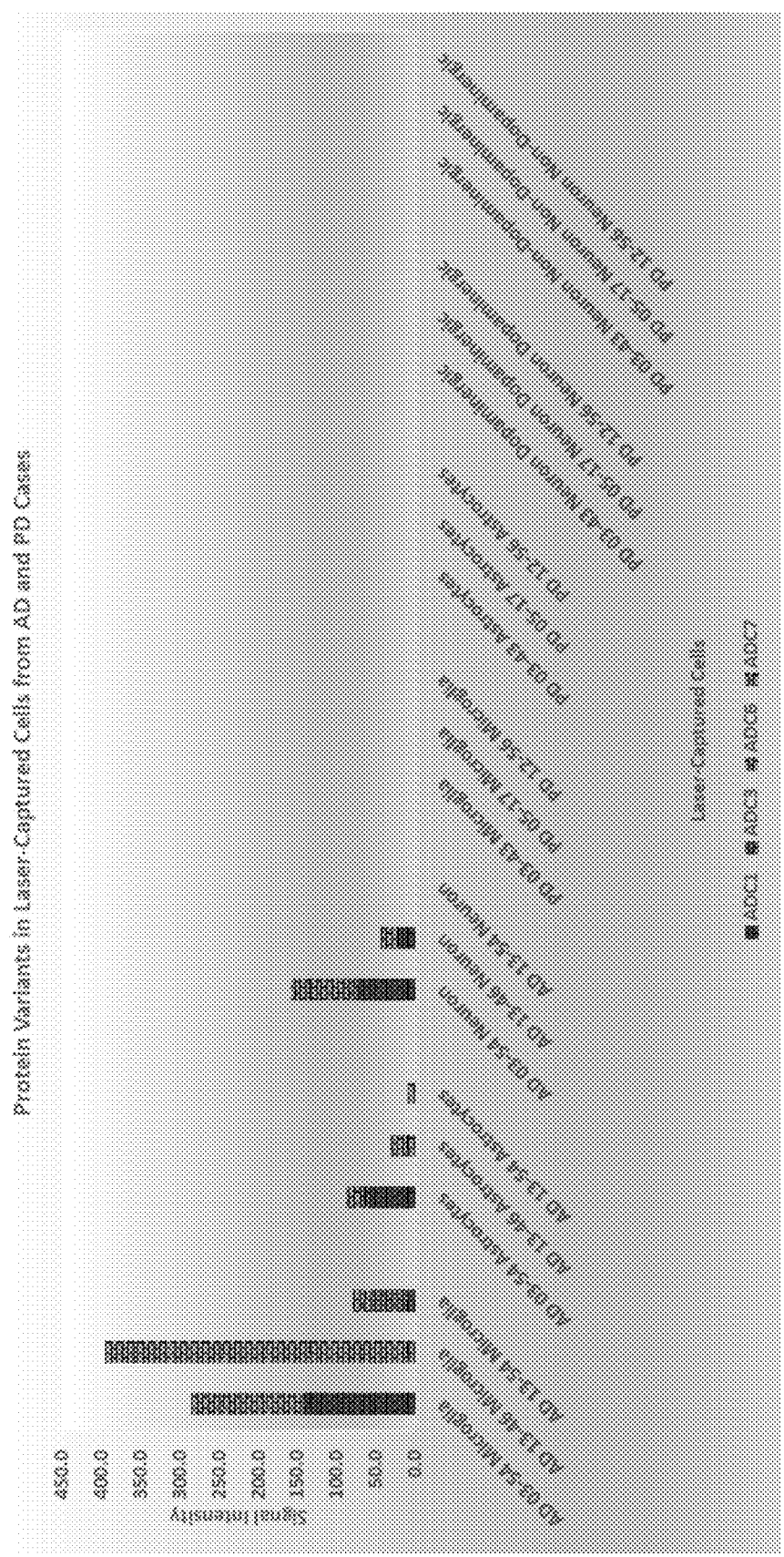
FIG. 34 illustrates the reactivity of the AD and PD cases with the AD DARPins and as is evident, the only reactivity is seen with the microglia, astrocytes and neurons from the AD cases.
Figure 35:
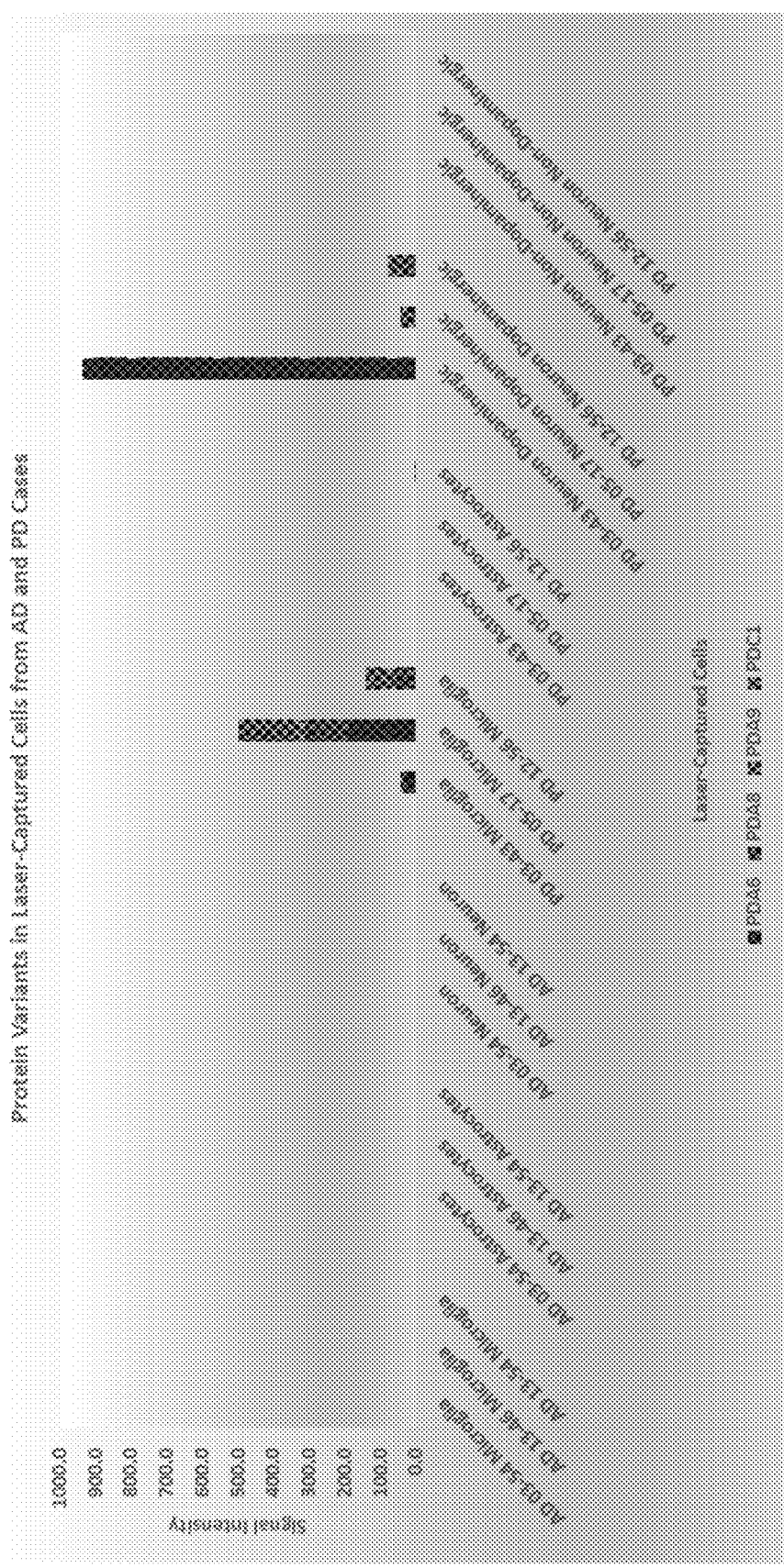
FIG. 35 shows the PD DARPins demonstrated reactivity only with the PD microglia and dopaminergic neurons, but not with any of the cell types from the AD cases.

To explore the binding specificity of the AD and PD DARPins, different cross-reactivity tests were completed. Using the 25 longitudinal AD and control cases described in table 1, all 8 DARPins were analyzed with these cases. ADC1, ADC3, ADC6 and ADC7 all displayed significantly higher reactivity with the AD cases compared to the controls (FIGS. 24-27). Incredibly, there was no difference in the reactivity between the AD and controls cases with the PDA6, PDA8, PDA9 and PDC1 DARPins (FIGS. 28-31). These results indicate that the AD DARPins are more selective for AD cases and the PD DARPins are inferior at recognizing AD cases. Microglia, astrocytes and neurons were acquired via laser-capture microdissection from 3 post-mortem pathologically confirmed AD, PD and ND human cases. Analysis of the 3 AD cases with the AD DARPins (horizontal bricks with different background shades) and PD DARPins (checker pattern with different background shades) resulted in strong reactivity with the AD DARPins and no reactivity with the PD DARPins (FIG. 32). Conversely, analysis of the PD cases with the AD and PD DARPins resulted in strong reactivity with PD DARPins and no reactivity with the AD DARPins (FIG. 33). To better illustrate this, FIG. 34 shows the reactivity of the AD and PD cases with the AD DARPins and as is evident, the only reactivity is seen with the microglia, astrocytes and neurons from the AD cases. Similarly, in FIG. 35, the PD DARPins demonstrated reactivity only with the PD microglia and dopaminergic neurons, but not with any of the cell types from the AD cases. These results further support the disease selectivity of our AD and PD DARPins, which will be very useful for more accurate disease diagnosis. This also indicates that there are Aβ, α-syn, TDP-43 and tau variants that are unique to AD and PD. Other interesting findings included Aβ's intensity levels matching the APOE genotype of the AD cases. AD case 03-54 had an APOE 44 genotype and the highest Aβ levels (whether in microglia, astrocyte or neuron), AD case 13-46 had an APOE 34 genotype and the second highest Aβ levels (neuron) and AD case 13-54 had an APOE 33 genotype and the lowest Aβ levels (FIG. 32). This pattern agrees with the literature where there seems to be a relationship between Aβ and APOE genotype. AD 03-54 also had severe amyloid angiopathy and an MMSE score of 0 which may correspond to its high level of Aβ variants. PD case 03-43 had really high Aβ levels in its dopaminergic neuron as detected by PDA6. Interestingly, this case also had an APOE 34 genotype, mild amyloid angiopathy and an MMSE score of 0.

Figure 36:
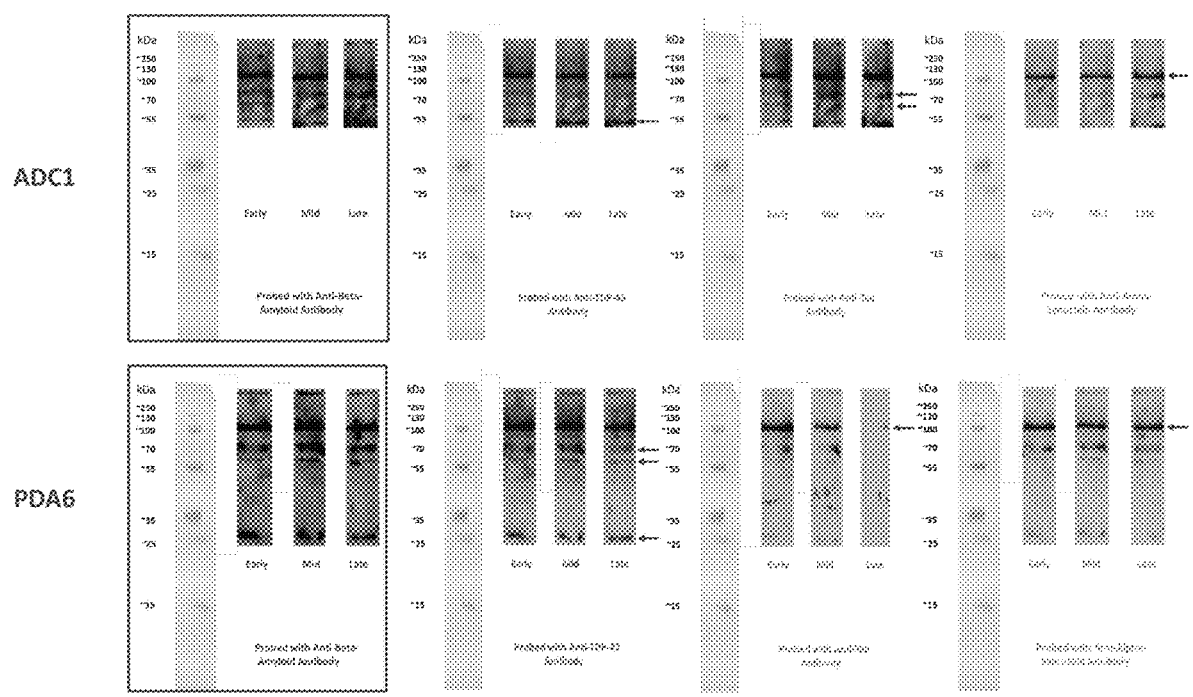
FIG. 36 illustrates starting with AP reactive DARPins ADC1 and PDA6 probing with the anti-Aβ antibody showed strong interaction with at ~25 kDa band for PDA6 compared to ADC1.
Figure 37:
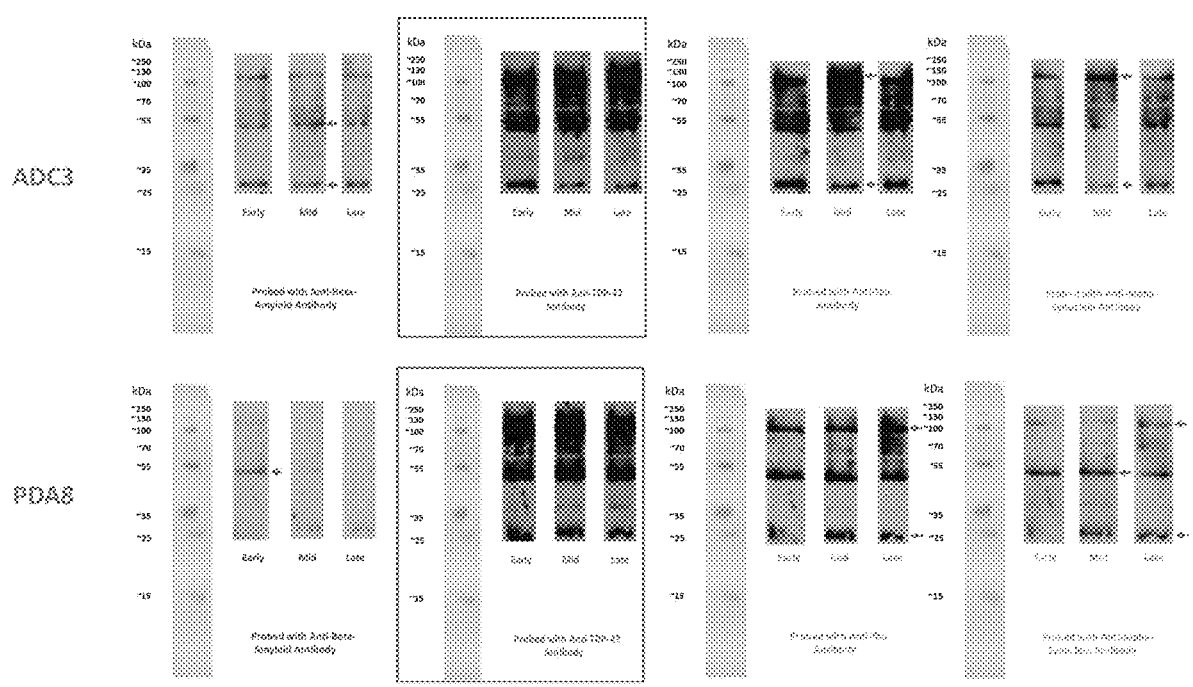
FIG. 37 illustrates probing with the anti-Aβ antibody showed some reactivity at ~25 kDa, ~43 kDa and above ~100 kDa bands for ADC3 while there was little reactivity with PDA8.
Figure 38:
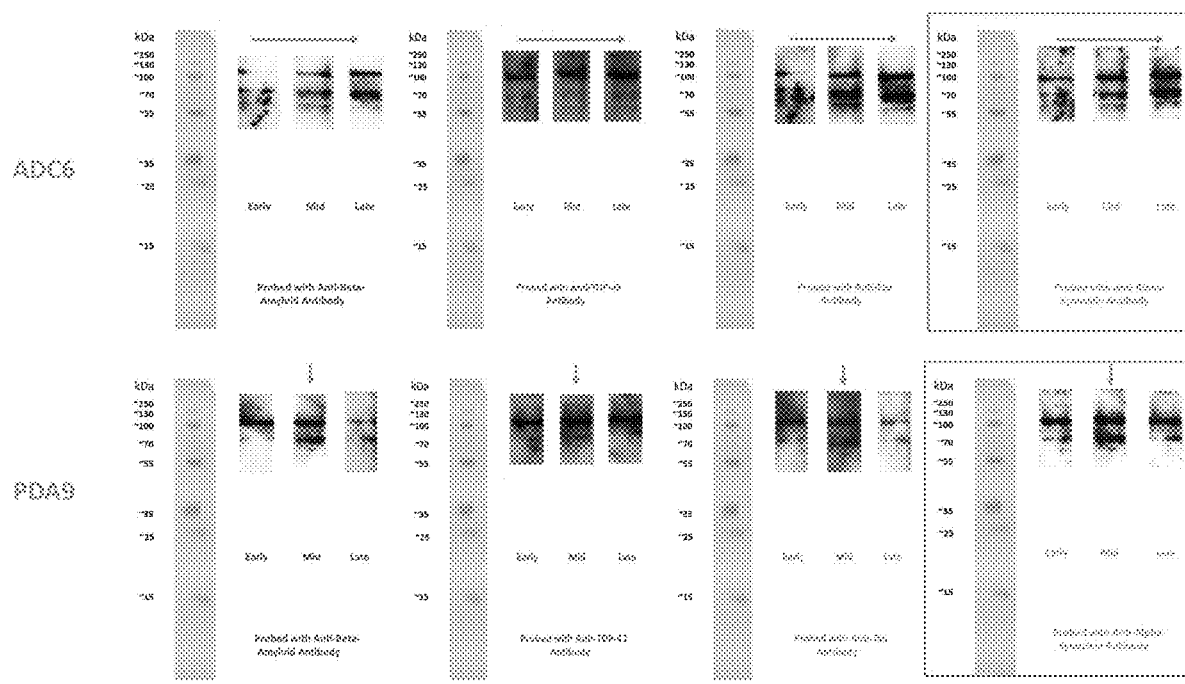
FIG. 38 illustrates the findings regarding the α-syn reactive DARPins ADC6 and PDA9, in that probing with the anti-Aβ, anti-TDP-43, anti-tau and anti-alpha-synuclein antibodies, showed differing patterns based on timepoints. For ADC6 the signal intensity seemed to increase across time, while with PDA9 the highest levels were seen at the middle timepoint.
Figure 39:
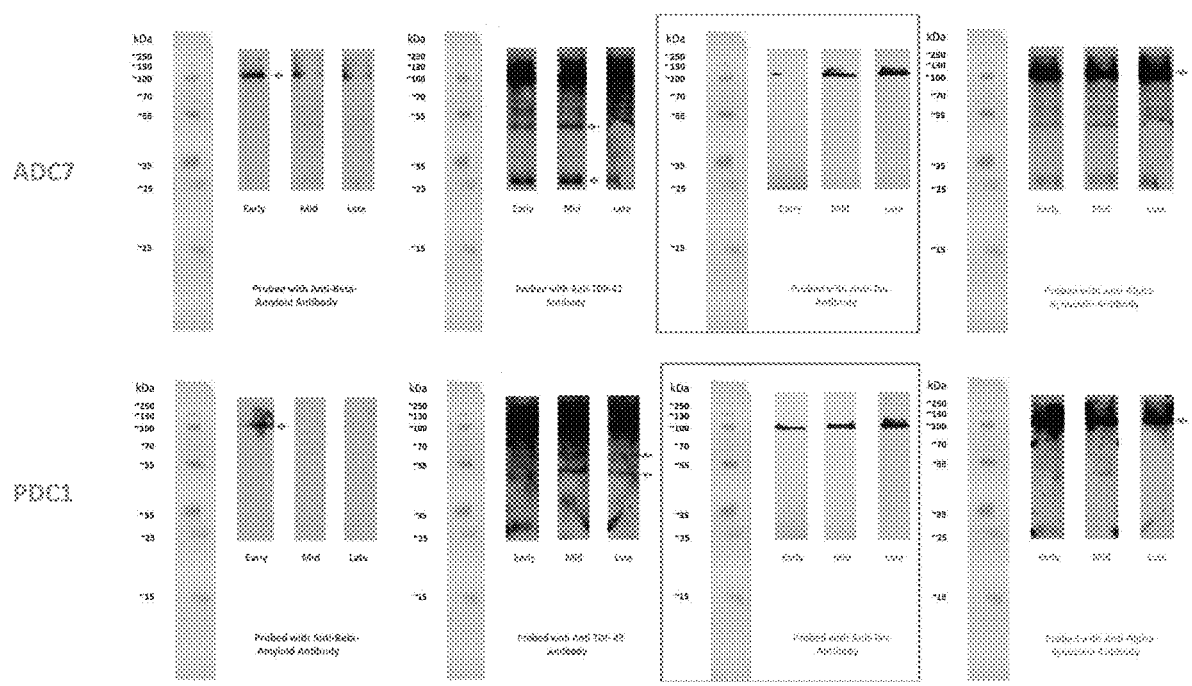
FIG. 39 illustrates the finds when the tau reactive DARPins ADC7 and PDC1 were probed with the anti-Aβ antibody, ADC7 showed some reactivity that decreased across time, while there was little to no reactivity with PDC1. There was strong reactivity with both DARPins when re-probed with the anti-TDP-43 antibody. With the anti-tau antibody, there was no reactivity at the first timepoint with ADC7, but the levels do increase across time, while with PDC1 reactivity was seen at all three timepoints. The reactivity with the α-syn antibody looked the same for both DARPins.

Comparison of the western blotting analyses of the immunoprecipitation experiments also helps to further highlight the differences between the AD and PD DARPins. Starting with Aβ reactive DARPins ADC1 and PDA6 probing with the anti-Aβ antibody showed strong interaction with a ~25 kDa band for PDA6 compared to ADC1 (FIG. 36). When re-probing with the anti-TDP-43 antibody, in addition to the high molecular weight band, ADC1 showed strong interaction with the ~54 kDa band while for PDA6 it was the ~25 kDa band. With the anti-tau antibody, for ADC1 the interaction was mostly with the higher molecular weight band at all three timepoint, while for PDA6 it was only at the first two timepoints (with decreasing reactivity). The reactivity with the α-syn antibody looked the same for both DARPins. Next, with ADC3 and PDA8, the DARPins reactive with TDP-43 variants, probing with the anti-Aβ antibody showed some reactivity at ~25 kDa, ~43 kDa and above ~100 kDa bands for ADC3 while there was little reactivity with PDA8 (FIG. 37). There was strong reactivity with the blots from both DARPins when re-probed with the anti-TDP-43 antibody, while with the anti-tau antibody there was more reactivity with ADC3 compared to PDA8. For ADC3 the reactivity with the α-syn antibody was strong at ~25 kDa, ~43 kDa and above ~100 kDa, while mostly at ~25 kDa and ~43 kDa bands for PDA8. Moving on to the α-syn reactive DARPins ADC6 and PDA9, probing with the anti-Aβ, anti-TDP-43, anti-tau and anti-alpha-synuclein antibodies, showed differing patterns based on timepoints (FIG. 38). For ADC6 the signal intensity seemed to increase across time, while with PDA9 the highest levels were seen at the middle timepoint. Lastly, when the tau reactive DARPins ADC7 and PDC1 were probed with the anti-Aβ antibody, ADC7 showed some reactivity that decreased across time, while there was little to no reactivity with PDC1 (FIG. 39). There was strong reactivity with both DARPins when re-probed with the anti-TDP-43 antibody. With the anti-tau antibody, there was no reactivity at the first timepoint with ADC7, but the levels do increase across time, while with PDC1 reactivity was seen at all three timepoints. The reactivity with the α-syn antibody looked the same for both DARPins.

Overall, the ELISA and western blotting results support the use of our AFM based biopanning process to isolate reagents reactive with biomarkers present in different diseases of interest. It also indicates the presence of distinct variants of Aβ, α-syn, TDP-43 and tau in AD versus PD. Because of the stability of DARPins this also supports linking multiple DARPins together to create a very effective therapeutic target for AD and PD.

The present disclosure is not to be limited in scope by the specific embodiments described herein. Indeed, various modifications of the disclosure in addition to those described herein will become apparent to those skilled in the art from the foregoing description and the accompanying figures. Such modifications are intended to fall within the scope of the appended claims.

What is claimed is:

1. A method of identifying a neurodegenerative disease in a biological sample, the method comprising:
    contacting a biological sample with at least one neurodegenerative disease-associated design ankyrin repeat protein (DARPin), wherein the at least one neurodegenerative disease-associated DARPin is selected from the group consisting of: ADC1 (SEQ ID NO: 5), ADC3 (SEQ ID NO: 7), ADC6 (SEQ ID NO: 9), ADC7 SEQ ID NO: 11), PDA6 (SEQ ID NO: 13), PDA8 (SEQ ID NO: 15), PDA9 (SEQ ID NO: 17), and PDC1 (SEQ ID NO: 19); and
    detecting the binding of at least one neurodegenerative disease-associated DARPin to the biological sample, wherein an increase in the binding of the at least one neurodegenerative disease-associated DARPin in the biological sample as compared to a control sample indicates the presence of the neurodegenerative disease in the biological sample.

2. The method of claim 1, wherein the neurodegenerative disease is Alzheimer's Disease (AD).

3. The method of claim 2, wherein the at least one neurodegenerative disease-associated DARPin is an AD-associated DARPin.

4. The method of claim 2, wherein the at least one AD-associated DARPin is ADC1 (SEQ ID NO: 5), ADC3 (SEQ ID NO: 7), ADC6 (SEQ ID NO: 9), and/or ADC7 (SEQ ID NO: 11).

5. The method of claim 3, wherein the biological sample is a serum sample or tissue sample.

6. The method of claim 4, wherein the biological sample is a serum sample.

7. The method of claim 6, wherein detecting the binding of the at least one neurodegenerative disease-associated DARPin comprises usage of at least one antibody specific for at least one of beta-amyloid (Aβ), Tar-DNA binding protein 43 (TDP-43), alpha-synuclein (α-syn), and/or tau.

8. The method of claim 7, wherein the method comprises using an ELISA.

9. The method of claim 1, wherein the neurodegenerative disease is Parkinson's Disease (PD).

10. The method of claim 9, wherein the at least one neurodegenerative disease-associated DARPin is a PD-associated DARPin.

11. The method of claim 10, wherein the at least one PD-associated DARPin is PDA6 (SEQ ID NO: 13), PDA8 (SEQ ID NO: 15), PDA9 (SEQ ID NO: 17), and/or PDC1 (SEQ ID NO: 19).

12. The method of claim 11, wherein the biological sample is a serum sample or tissue sample.

13. The method of claim 12, wherein the biological sample is a serum sample.

14. The method of claim 13, wherein detecting the binding of the at least one neurodegenerative disease-associated DARPin comprises usage of at least one antibody specific for at least one of beta-amyloid (Aβ), Tar-DNA binding protein 43 (TDP-43), alpha-synuclein (α-syn), and/or tau.

15. The method of claim 14, wherein the method comprises using an ELISA.

* * * * *